US012636073B2

(12) United States Patent
Yih et al.

(10) Patent No.: US 12,636,073 B2
(45) Date of Patent: May 26, 2026

(54) SOFT PALATE TREATMENT

(71) Applicant: AERIN MEDICAL INC., Sunnyvale, CA (US)

(72) Inventors: Charlton Yih, San Mateo, CA (US); Yen Hai Tieu, San Jose, CA (US); Andrew Frazier, Sunnyvale, CA (US); Scott J. Wolf, Menlo Park, CA (US); Fred Dinger, Austin, TX (US)

(73) Assignee: Aerin Medical, Inc., Mountain View, CA (US)

( * ) Notice: Subject to any disclaimer, the term of this patent is extended or adjusted under 35 U.S.C. 154(b) by 675 days.

(21) Appl. No.: 17/454,561

(22) Filed: Nov. 11, 2021

(65) Prior Publication Data

US 2022/0151689 A1 May 19, 2022

Related U.S. Application Data

(60) Provisional application No. 63/114,257, filed on Nov. 16, 2020.

(51) Int. Cl.
A61B 18/14 (2006.01)
A61B 17/00 (2006.01)
(Continued)

(52) U.S. Cl.
CPC .............................. A61B 18/1485 (2013.01); *A61B 2017/00946* (2013.01); *A61B 2017/248* (2013.01);
(Continued)

(58) Field of Classification Search
CPC ........... A61B 2018/00005; A61B 2018/00011; A61B 2018/00023; A61B 2018/1422; A61B 18/14; A61B 18/1485
See application file for complete search history.

(56) References Cited

U.S. PATENT DOCUMENTS

| 874,178 | A | 12/1907 | DeForest |
| 3,117,571 | A | 1/1964 | Fry et al. |
| | | (Continued) | |

FOREIGN PATENT DOCUMENTS

| CN | 2225227 | Y | 4/1996 |
| CN | 2621723 | | 6/2004 |
| | | (Continued) | |

OTHER PUBLICATIONS

"Non-Invasive Nasal Airway Remodeling." Aerin Medical, published Sep. 27, 2017 (Retrieved from the Internet Jan. 30, 2020). Internet URL: <https://web.archive.org/web/20170927181830/https://aerinmedical .com/> (Year: 2017).
(Continued)

*Primary Examiner* — Bradford C. Blaise
(74) *Attorney, Agent, or Firm* — Greenberg Traurig, LLP; Roman Fayerberg; Jaime Burke

(57) ABSTRACT

A method of treating a soft palate in a patient may involve advancing a tissue treatment portion of a soft palate treatment device through the patient's mouth, contacting a treatment surface of the tissue treatment portion with mucosal tissue of the soft palate, and delivering energy from the tissue treatment portion through the mucosal tissue to a target tissue in the soft palate beneath to the mucosal tissue, to change at least one property of the target tissue. The method may further involve cooling the mucosal tissue with a cooling member on the treatment surface of the tissue treatment portion and removing the tissue treatment portion from the mouth.

25 Claims, 31 Drawing Sheets

(51) Int. Cl.
　　*A61B 17/24*　　　(2006.01)
　　*A61B 18/00*　　　(2006.01)
　　*A61B 18/12*　　　(2006.01)
(52) U.S. Cl.
　　CPC .............. *A61B 2018/00017* (2013.01); *A61B 2018/00023* (2013.01); *A61B 2018/00047* (2013.01); *A61B 2018/0016* (2013.01); *A61B 2018/00327* (2013.01); *A61B 2018/00791* (2013.01); *A61B 2018/126* (2013.01); *A61B 2018/1467* (2013.01)

(56) References Cited

U.S. PATENT DOCUMENTS

| | | | |
|---|---|---|---|
| 3,538,919 A | 11/1970 | Meyer |
| 3,941,121 A | 3/1976 | Olinger et al. |
| 4,074,718 A | 2/1978 | Morrison |
| 4,271,848 A | 6/1981 | Turner et al. |
| 4,411,266 A | 10/1983 | Cosman |
| 4,887,605 A | 12/1989 | Angelsen et al. |
| 5,255,679 A | 10/1993 | Imran |
| 5,348,008 A | 9/1994 | Bornn et al. |
| 5,505,730 A | 4/1996 | Edwards |
| 5,507,725 A | 4/1996 | Savage et al. |
| 5,514,131 A | 5/1996 | Edwards et al. |
| 5,533,499 A | 7/1996 | Johnson |
| 5,542,916 A | 8/1996 | Hirsch et al. |
| 5,562,720 A | 10/1996 | Stern et al. |
| 5,575,788 A | 11/1996 | Baker et al. |
| 5,611,798 A | 3/1997 | Eggers |
| 5,624,439 A | 4/1997 | Edwards et al. |
| 5,674,191 A | 10/1997 | Edwards et al. |
| 5,697,536 A | 12/1997 | Eggers et al. |
| 5,707,349 A | 1/1998 | Edwards |
| 5,718,702 A | 2/1998 | Edwards |
| 5,728,094 A | 3/1998 | Edwards |
| 5,730,719 A | 3/1998 | Edwards |
| 5,733,280 A | 3/1998 | Avitall |
| 5,738,114 A | 4/1998 | Edwards |
| 5,743,870 A | 4/1998 | Edwards |
| 5,743,904 A | 4/1998 | Edwards |
| 5,746,224 A | 5/1998 | Edwards |
| 5,766,153 A | 6/1998 | Eggers et al. |
| 5,766,605 A | 6/1998 | Sanders et al. |
| 5,800,429 A | 9/1998 | Edwards |
| 5,807,306 A | 9/1998 | Shapland et al. |
| 5,816,095 A | 10/1998 | Nordell, II et al. |
| 5,817,049 A | 10/1998 | Edwards |
| 5,820,580 A | 10/1998 | Edwards et al. |
| 5,823,197 A | 10/1998 | Edwards |
| 5,827,277 A | 10/1998 | Edwards |
| 5,843,021 A | 12/1998 | Edwards et al. |
| 5,843,077 A | 12/1998 | Edwards |
| 5,846,235 A | 12/1998 | Pasricha et al. |
| 5,879,349 A | 3/1999 | Edwards |
| 5,891,134 A | 4/1999 | Goble et al. |
| 5,938,659 A | 8/1999 | Tu |
| 5,944,715 A | 8/1999 | Goble |
| 6,026,816 A | 2/2000 | McMillan et al. |
| 6,033,397 A | 3/2000 | Laufer et al. |
| 6,045,549 A | 4/2000 | Smethers et al. |
| 6,096,033 A | 8/2000 | Tu et al. |
| 6,102,907 A | 8/2000 | Smethers et al. |
| 6,106,520 A | 8/2000 | Laufer et al. |
| 6,109,268 A | 8/2000 | Thapliyal et al. |
| 6,126,657 A | 10/2000 | Edwards et al. |
| 6,131,579 A | 10/2000 | Thorson et al. |
| 6,139,545 A | 10/2000 | Utley et al. |
| 6,139,546 A | 10/2000 | Koenig et al. |
| 6,139,569 A | 10/2000 | Ingle et al. |
| 6,152,143 A | 11/2000 | Edwards |
| 6,165,173 A | 12/2000 | Kamdar et al. |
| 6,179,803 B1 | 1/2001 | Edwards et al. |
| 6,210,355 B1 | 4/2001 | Edwards et al. |
| 6,228,079 B1 | 5/2001 | Koenig |
| 6,231,569 B1 | 5/2001 | Bek et al. |
| 6,238,394 B1 | 5/2001 | Garito et al. |
| 6,273,886 B1 | 8/2001 | Edwards et al. |
| 6,273,907 B1 | 8/2001 | Laufer |
| 6,283,961 B1 | 9/2001 | Underwood et al. |
| 6,293,941 B1 | 9/2001 | Strul et al. |
| 6,309,386 B1 | 10/2001 | Bek |
| 6,355,032 B1 | 3/2002 | Hovda et al. |
| 6,361,531 B1 | 3/2002 | Hissong |
| 6,371,926 B1 | 4/2002 | Thorson et al. |
| 6,383,181 B1 | 5/2002 | Johnston et al. |
| 6,391,028 B1 | 5/2002 | Fanton et al. |
| 6,405,732 B1 | 6/2002 | Edwards et al. |
| 6,416,491 B1 | 7/2002 | Edwards et al. |
| 6,416,505 B1 | 7/2002 | Fleishman et al. |
| 6,425,151 B2 | 7/2002 | Barnett |
| 6,431,174 B1 | 8/2002 | Knudson et al. |
| 6,451,013 B1 | 9/2002 | Bays et al. |
| 6,502,574 B2 | 1/2003 | Stevens |
| 6,517,534 B1 | 2/2003 | McGovern et al. |
| 6,517,535 B2 | 2/2003 | Edwards |
| 6,530,924 B1 | 3/2003 | Ellman et al. |
| 6,551,310 B1 | 4/2003 | Ganz et al. |
| 6,562,036 B1 | 5/2003 | Ellman et al. |
| 6,575,969 B1 | 6/2003 | Rittman et al. |
| 6,589,235 B2 | 7/2003 | Wong et al. |
| 6,640,120 B1 | 10/2003 | Swanson et al. |
| 6,658,279 B2 | 12/2003 | Swanson et al. |
| 6,659,106 B1 | 12/2003 | Hovda et al. |
| 6,669,689 B2 | 12/2003 | Lehmann et al. |
| 6,685,648 B2 | 2/2004 | Flaherty et al. |
| 6,896,674 B1 | 5/2005 | Woloszko et al. |
| 6,911,027 B1 | 6/2005 | Edwards et al. |
| 6,978,781 B1 | 12/2005 | Jordan |
| 7,055,523 B1 | 6/2006 | Brown |
| 7,097,641 B1 | 8/2006 | Arless et al. |
| 7,114,495 B2 | 10/2006 | Lockwood, Jr. |
| 7,322,993 B2 | 1/2008 | Metzger et al. |
| 7,361,168 B2 | 4/2008 | Makower et al. |
| 7,416,550 B2 | 8/2008 | Protsenko et al. |
| 7,442,191 B2 | 10/2008 | Hovda et al. |
| 7,572,251 B1 | 8/2009 | Davison et al. |
| 7,628,789 B2 | 12/2009 | Soltesz et al. |
| 7,655,243 B2 | 2/2010 | Deem et al. |
| 7,678,069 B1 | 3/2010 | Baker et al. |
| 7,780,730 B2 | 8/2010 | Saidi |
| 7,824,394 B2 | 11/2010 | Manstein |
| 7,850,683 B2 | 12/2010 | Elkins et al. |
| 7,997,278 B2 | 8/2011 | Utley et al. |
| 8,088,122 B2 | 1/2012 | Li et al. |
| 8,114,062 B2 | 2/2012 | Muni et al. |
| 8,128,617 B2 | 3/2012 | Bencini et al. |
| 8,137,345 B2 | 3/2012 | McNall, III et al. |
| 8,317,781 B2 | 11/2012 | Owens et al. |
| 8,317,782 B1 | 11/2012 | Ellman et al. |
| 8,718,786 B2 | 5/2014 | Shalev |
| D716,325 S | 10/2014 | Brudnicki |
| 8,925,551 B2 | 1/2015 | Sanders |
| 8,936,594 B2 | 1/2015 | Wolf et al. |
| 8,939,970 B2 | 1/2015 | Stone et al. |
| 8,979,841 B2 | 3/2015 | Kunis et al. |
| 8,986,301 B2 | 3/2015 | Wolf et al. |
| 9,072,597 B2 | 7/2015 | Wolf et al. |
| 9,119,954 B2 | 9/2015 | Burdette et al. |
| 9,125,677 B2 | 9/2015 | Sobol |
| 9,179,964 B2 | 11/2015 | Wolf et al. |
| 9,179,967 B2 | 11/2015 | Wolf et al. |
| 9,237,924 B2 | 1/2016 | Wolf et al. |
| 9,247,989 B2 | 2/2016 | Truckai |
| D763,910 S | 8/2016 | Drozd |
| D765,091 S | 8/2016 | Del Lima |
| 9,415,194 B2 | 8/2016 | Wolf et al. |
| D765,718 S | 9/2016 | Vinna |
| 9,433,463 B2 | 9/2016 | Wolf et al. |
| 9,452,010 B2 | 9/2016 | Wolf et al. |
| 9,452,087 B2 | 9/2016 | Holm et al. |
| 9,486,278 B2 | 11/2016 | Wolf et al. |
| 9,498,241 B2 | 11/2016 | Leonhard et al. |
| 9,526,571 B2 | 12/2016 | Wolf et al. |

(56) References Cited

U.S. PATENT DOCUMENTS

| | | | |
|---|---|---|---|
| 9,526,652 | B2 | 12/2016 | Harrison et al. |
| D776,717 | S | 1/2017 | Asai |
| D782,657 | S | 3/2017 | Williams |
| D789,383 | S | 6/2017 | Bawazeer |
| 9,687,288 | B2 | 6/2017 | Saadat |
| 9,687,296 | B2 | 6/2017 | Wolf et al. |
| D795,898 | S | 8/2017 | Li |
| D797,756 | S | 9/2017 | Meyer |
| 9,763,723 | B2 | 9/2017 | Saadat |
| 9,763,743 | B2 | 9/2017 | Lin |
| 9,770,293 | B2 | 9/2017 | Dresher |
| 9,788,886 | B2 | 10/2017 | Wolf et al. |
| 9,801,752 | B2 | 10/2017 | Wolf et al. |
| 9,888,957 | B2 | 2/2018 | Wolf et al. |
| 9,913,682 | B2 | 3/2018 | Wolf et al. |
| 9,943,361 | B2 | 4/2018 | Wolf et al. |
| 10,028,780 | B2 | 7/2018 | Wolf et al. |
| 10,028,781 | B2 | 7/2018 | Saadat |
| D840,428 | S | 2/2019 | Narinedhat |
| D844,013 | S | 3/2019 | Peeters |
| 10,265,115 | B2 | 4/2019 | Wolf et al. |
| 10,307,200 | B2 | 6/2019 | Saadat |
| 10,335,221 | B2 | 7/2019 | Wolf et al. |
| D857,034 | S | 8/2019 | Hung |
| 10,376,300 | B2 | 8/2019 | Wolf et al. |
| D860,315 | S | 9/2019 | Chen |
| 10,398,489 | B2 | 9/2019 | Wolf et al. |
| 10,456,185 | B2 | 10/2019 | Wolf et al. |
| 10,456,186 | B1 | 10/2019 | Wolf et al. |
| 10,470,814 | B2 | 11/2019 | Wolf et al. |
| 10,485,603 | B2 | 11/2019 | Wolf et al. |
| D874,492 | S | 2/2020 | Henderson |
| D875,742 | S | 2/2020 | Kang |
| D877,171 | S | 3/2020 | Poindexter |
| 10,603,059 | B2 | 3/2020 | Dinger et al. |
| D880,694 | S | 4/2020 | Ng et al. |
| D881,904 | S | 4/2020 | Angeles et al. |
| 10,631,925 | B2 | 4/2020 | Wolf et al. |
| 10,722,282 | B2 | 7/2020 | Wolf et al. |
| D897,185 | S | 9/2020 | Perkins, Jr. et al. |
| D897,186 | S | 9/2020 | Perkins, Jr. et al. |
| 10,779,873 | B2 | 9/2020 | Wolf et al. |
| 10,806,921 | B2 | 10/2020 | Townley et al. |
| D902,412 | S | 11/2020 | Angeles et al. |
| D904,698 | S | 12/2020 | Moeller et al. |
| D904,852 | S | 12/2020 | Levand et al. |
| 10,864,035 | B2 | 12/2020 | Hester et al. |
| D906,782 | S | 1/2021 | Brinson et al. |
| D910,408 | S | 2/2021 | Lin |
| D911,140 | S | 2/2021 | Hyma et al. |
| D911,141 | S | 2/2021 | Panosian et al. |
| 10,932,853 | B2 | 3/2021 | Wolf et al. |
| 11,033,318 | B2 | 6/2021 | Wolf et al. |
| D927,687 | S | 8/2021 | Stoklund et al. |
| 11,116,566 | B2 | 9/2021 | Dinger et al. |
| 11,241,271 | B2 | 2/2022 | Wolf et al. |
| 11,304,746 | B2 | 4/2022 | Wolf et al. |
| 11,457,971 | B2 | 10/2022 | Wolf et al. |
| 11,759,222 | B2 | 9/2023 | Wolf et al. |
| 11,766,286 | B2 | 9/2023 | Wolf et al. |
| 11,771,497 | B2 | 10/2023 | Townley et al. |
| 11,801,084 | B2 | 10/2023 | Wolf et al. |
| 11,806,071 | B2 * | 11/2023 | Frazier .................. A61B 18/02 |
| 11,832,876 | B2 | 12/2023 | Wolf et al. |
| 11,883,091 | B2 | 1/2024 | Townley |
| 11,896,818 | B2 | 2/2024 | Townley |
| 11,969,200 | B2 | 4/2024 | Hester et al. |
| 12,053,227 | B2 | 8/2024 | Wolf et al. |
| 12,082,872 | B2 | 9/2024 | Townley et al. |
| 12,108,979 | B2 | 10/2024 | Townley |
| 12,336,750 | B2 | 6/2025 | Frazier et al. |
| 12,357,817 | B2 | 7/2025 | Wolf et al. |
| 12,369,963 | B1 | 7/2025 | Wolf et al. |
| 12,369,973 | B1 | 7/2025 | Wolf et al. |
| 2002/0010460 | A1 | 1/2002 | Joye et al. |
| 2002/0016588 | A1 | 2/2002 | Wong et al. |
| 2002/0035361 | A1 | 3/2002 | Houser |
| 2002/0049464 | A1 | 4/2002 | Donofrio et al. |
| 2002/0087155 | A1 | 7/2002 | Underwood et al. |
| 2002/0095152 | A1 | 7/2002 | Ciarrocca et al. |
| 2002/0120259 | A1 | 8/2002 | Lettice et al. |
| 2002/0128641 | A1 | 9/2002 | Underwood et al. |
| 2002/0156470 | A1 * | 10/2002 | Shadduck .......... A61B 18/1485 606/41 |
| 2003/0069620 | A1 | 4/2003 | Li |
| 2003/0139789 | A1 | 7/2003 | Tvinnereim et al. |
| 2003/0144659 | A1 | 7/2003 | Edwards |
| 2003/0208194 | A1 | 11/2003 | Hovda et al. |
| 2003/0208250 | A1 | 11/2003 | Edwards et al. |
| 2003/0225403 | A1 | 12/2003 | Woloszko et al. |
| 2004/0030334 | A1 | 2/2004 | Quick et al. |
| 2004/0049180 | A1 | 3/2004 | Sharps |
| 2004/0193238 | A1 | 9/2004 | Mosher et al. |
| 2004/0210214 | A1 | 10/2004 | Knowlton |
| 2004/0215235 | A1 | 10/2004 | Jackson et al. |
| 2004/0220644 | A1 | 11/2004 | Shalev et al. |
| 2004/0230188 | A1 | 11/2004 | Cioanta et al. |
| 2005/0020901 | A1 | 1/2005 | Belson |
| 2005/0119643 | A1 | 6/2005 | Sobol et al. |
| 2005/0171522 | A1 | 8/2005 | Christopherson |
| 2005/0171574 | A1 | 8/2005 | Rubinsky et al. |
| 2005/0222565 | A1 | 10/2005 | Manstein |
| 2005/0234439 | A1 | 10/2005 | Underwood |
| 2005/0234443 | A1 | 10/2005 | Rioux et al. |
| 2005/0240147 | A1 | 10/2005 | Makower et al. |
| 2005/0283148 | A1 | 12/2005 | Janssen et al. |
| 2005/0288655 | A1 | 12/2005 | Root et al. |
| 2005/0288665 | A1 | 12/2005 | Woloszko et al. |
| 2006/0004323 | A1 | 1/2006 | Chang et al. |
| 2006/0009758 | A1 | 1/2006 | Edwards et al. |
| 2006/0064086 | A1 | 3/2006 | Odom |
| 2006/0095066 | A1 | 5/2006 | Chang et al. |
| 2006/0190022 | A1 | 8/2006 | Beyer et al. |
| 2006/0195169 | A1 | 8/2006 | Gross et al. |
| 2006/0235377 | A1 | 10/2006 | Earley |
| 2006/0253117 | A1 | 11/2006 | Hovda et al. |
| 2006/0265031 | A1 | 11/2006 | Skwarek et al. |
| 2006/0276817 | A1 | 12/2006 | Vassallo et al. |
| 2006/0276861 | A1 | 12/2006 | Lin |
| 2006/0287677 | A1 | 12/2006 | Shalev et al. |
| 2007/0043350 | A1 | 2/2007 | Soltesz et al. |
| 2007/0049999 | A1 | 3/2007 | Esch et al. |
| 2007/0066944 | A1 | 3/2007 | Nyte |
| 2007/0073282 | A1 | 3/2007 | McGarrigan et al. |
| 2007/0083193 | A1 | 4/2007 | Werneth et al. |
| 2007/0093710 | A1 | 4/2007 | Maschke |
| 2007/0179495 | A1 | 8/2007 | Mitchell et al. |
| 2007/0219600 | A1 | 9/2007 | Gertner et al. |
| 2007/0244529 | A1 | 10/2007 | Choi et al. |
| 2007/0287994 | A1 | 12/2007 | Patel |
| 2008/0000477 | A1 | 1/2008 | Huster et al. |
| 2008/0004613 | A1 | 1/2008 | Barbut et al. |
| 2008/0021369 | A1 | 1/2008 | Deem et al. |
| 2008/0027423 | A1 | 1/2008 | Choi et al. |
| 2008/0027480 | A1 | 1/2008 | van der Burg et al. |
| 2008/0027520 | A1 | 1/2008 | Choi et al. |
| 2008/0082090 | A1 | 4/2008 | Manstein |
| 2008/0125626 | A1 | 5/2008 | Chang et al. |
| 2008/0154237 | A1 | 6/2008 | Chang et al. |
| 2008/0154343 | A1 | 6/2008 | Li et al. |
| 2008/0183251 | A1 | 7/2008 | Azar et al. |
| 2008/0255642 | A1 | 10/2008 | Zarins et al. |
| 2008/0312644 | A1 | 12/2008 | Fourkas et al. |
| 2009/0018485 | A1 | 1/2009 | Krespi et al. |
| 2009/0124958 | A1 | 5/2009 | Li |
| 2009/0143821 | A1 | 6/2009 | Stupak |
| 2009/0163890 | A1 | 6/2009 | Clifford et al. |
| 2009/0192505 | A1 | 7/2009 | Askew et al. |
| 2009/0292358 | A1 | 11/2009 | Saidi |
| 2009/0299355 | A1 | 12/2009 | Bencini et al. |
| 2010/0049188 | A1 | 2/2010 | Nelson et al. |
| 2010/0144996 | A1 | 6/2010 | Kennedy et al. |
| 2010/0152730 | A1 | 6/2010 | Makower et al. |
| 2010/0160906 | A1 | 6/2010 | Jarrard |

(56) References Cited

U.S. PATENT DOCUMENTS

| | | |
|---|---|---|
| 2010/0174283 A1 | 7/2010 | McNall |
| 2010/0204560 A1 | 8/2010 | Salahieh et al. |
| 2010/0241112 A1 | 9/2010 | Watson |
| 2010/0260703 A1 | 10/2010 | Yankelson et al. |
| 2010/0262133 A1 | 10/2010 | Hoey et al. |
| 2011/0009737 A1 | 1/2011 | Manstein |
| 2011/0118726 A1 | 5/2011 | De La Rama et al. |
| 2011/0125149 A1 | 5/2011 | El-Galley et al. |
| 2011/0130689 A1 | 6/2011 | Cohen et al. |
| 2011/0180064 A1 | 7/2011 | Tanaka et al. |
| 2011/0218464 A1 | 9/2011 | Iger et al. |
| 2011/0282268 A1 | 11/2011 | Baker et al. |
| 2011/0288477 A1 | 11/2011 | Ressemann et al. |
| 2011/0301587 A1 | 12/2011 | Deem et al. |
| 2012/0029512 A1 | 2/2012 | Willard et al. |
| 2012/0039954 A1 | 2/2012 | Cupit et al. |
| 2012/0059255 A1 | 3/2012 | Paul et al. |
| 2012/0078377 A1 | 3/2012 | Gonzales et al. |
| 2012/0123411 A1 | 5/2012 | Ibrahim et al. |
| 2012/0179154 A1 | 7/2012 | Goldberg et al. |
| 2012/0197361 A1* | 8/2012 | Gonzales .................. A61F 7/12 607/105 |
| 2012/0209257 A1 | 8/2012 | Van Der Weide et al. |
| 2012/0265188 A1 | 10/2012 | Buchbinder et al. |
| 2012/0271294 A1 | 10/2012 | Barthe et al. |
| 2012/0298105 A1 | 11/2012 | Osorio |
| 2012/0310233 A1 | 12/2012 | Dimmer et al. |
| 2012/0316473 A1 | 12/2012 | Bonutti et al. |
| 2012/0316557 A1 | 12/2012 | Sartor et al. |
| 2012/0323227 A1 | 12/2012 | Wolf et al. |
| 2012/0323232 A1 | 12/2012 | Wolf et al. |
| 2013/0085546 A1* | 4/2013 | Bolea .................. A61N 1/3601 607/42 |
| 2013/0116679 A1 | 5/2013 | Van der Weide et al. |
| 2013/0158536 A1 | 6/2013 | Bloom |
| 2013/0165990 A1 | 6/2013 | Mathur et al. |
| 2013/0218158 A1 | 8/2013 | Danek et al. |
| 2013/0281997 A1 | 10/2013 | Davie |
| 2014/0088463 A1 | 3/2014 | Wolf et al. |
| 2014/0114233 A1 | 4/2014 | Deem et al. |
| 2014/0243793 A1 | 8/2014 | Morriss et al. |
| 2014/0316396 A1 | 10/2014 | Wolf et al. |
| 2015/0112328 A1 | 4/2015 | Willard et al. |
| 2015/0141982 A1 | 5/2015 | Lee |
| 2015/0148791 A1 | 5/2015 | Birdsall et al. |
| 2015/0164571 A1 | 6/2015 | Saadat |
| 2015/0202003 A1 | 7/2015 | Wolf et al. |
| 2016/0045277 A1 | 2/2016 | Lin et al. |
| 2016/0058336 A1 | 3/2016 | Blahnik et al. |
| 2016/0121112 A1 | 5/2016 | Azar |
| 2016/0274661 A1 | 9/2016 | Maeda |
| 2016/0287315 A1 | 10/2016 | Wolf et al. |
| 2016/0317803 A1 | 11/2016 | Sama |
| 2016/0331459 A1 | 11/2016 | Townley |
| 2016/0354136 A1 | 12/2016 | Saadat |
| 2017/0105793 A1 | 4/2017 | Cao |
| 2017/0224987 A1 | 8/2017 | Kent et al. |
| 2017/0231651 A1 | 8/2017 | Dinger et al. |
| 2017/0252089 A1 | 9/2017 | Hester |
| 2017/0252100 A1 | 9/2017 | Wolf et al. |
| 2017/0357419 A1 | 12/2017 | Raymann |
| 2017/0360495 A1 | 12/2017 | Wolf et al. |
| 2018/0000535 A1 | 1/2018 | Wolf et al. |
| 2018/0103940 A1 | 4/2018 | Shin et al. |
| 2018/0177542 A1 | 6/2018 | Wolf et al. |
| 2018/0177546 A1 | 6/2018 | Dinger et al. |
| 2018/0185085 A1 | 7/2018 | Wolf et al. |
| 2018/0228533 A1 | 8/2018 | Wolf et al. |
| 2018/0228551 A1 | 8/2018 | Moe |
| 2018/0263678 A1 | 9/2018 | Saadat |
| 2018/0317997 A1 | 11/2018 | Dinger et al. |
| 2018/0333195 A1 | 11/2018 | Greep et al. |
| 2018/0344378 A1 | 12/2018 | Wolf et al. |
| 2019/0076185 A1 | 3/2019 | Dinger et al. |
| 2019/0151005 A1 | 5/2019 | Wolf et al. |
| 2019/0175242 A1 | 6/2019 | Wolf et al. |
| 2019/0201069 A1 | 7/2019 | Wolf et al. |
| 2019/0231409 A1 | 8/2019 | Wolf et al. |
| 2019/0282289 A1 | 9/2019 | Wolf et al. |
| 2019/0290352 A1* | 9/2019 | Viswanadha ............ A61N 1/06 |
| 2019/0336196 A1 | 11/2019 | Wolf et al. |
| 2019/0343577 A1 | 11/2019 | Wolf et al. |
| 2019/0357927 A1 | 11/2019 | Palushi |
| 2020/0100829 A1 | 4/2020 | Wolf et al. |
| 2020/0129223 A1 | 4/2020 | Angeles et al. |
| 2020/0170699 A1 | 6/2020 | Wolf et al. |
| 2020/0205884 A1 | 7/2020 | Wolf et al. |
| 2020/0268439 A1 | 8/2020 | Frazier et al. |
| 2020/0375648 A1 | 12/2020 | Wolf et al. |
| 2020/0405383 A1 | 12/2020 | Townley |
| 2021/0169566 A1 | 6/2021 | Townley |
| 2021/0236815 A1 | 8/2021 | Waldstreicher et al. |
| 2021/0275241 A1 | 9/2021 | Fahey |
| 2021/0315638 A1 | 10/2021 | Townley et al. |
| 2022/0022951 A1 | 1/2022 | Townley |
| 2022/0071802 A1* | 3/2022 | Christopherson ...... A61B 18/02 |
| 2022/0079656 A1 | 3/2022 | Townley |
| 2022/0104862 A1 | 4/2022 | Townley et al. |
| 2022/0104866 A1 | 4/2022 | Townley et al. |
| 2022/0104869 A1 | 4/2022 | Townley et al. |
| 2022/0104870 A1 | 4/2022 | Townley et al. |
| 2022/0142699 A1 | 5/2022 | Wolf et al. |
| 2022/0257272 A1 | 8/2022 | Wolf et al. |
| 2022/0361941 A1 | 11/2022 | Townley |
| 2023/0062359 A1 | 3/2023 | Wolf et al. |
| 2023/0277236 A1 | 9/2023 | Townley et al. |
| 2023/0293222 A1 | 9/2023 | Wolf et al. |
| 2023/0372003 A1 | 11/2023 | Townley |
| 2023/0372004 A1 | 11/2023 | Townley |
| 2024/0024016 A1 | 1/2024 | Wolf et al. |
| 2024/0050143 A1 | 2/2024 | Wolf et al. |
| 2024/0050148 A1 | 2/2024 | Wolf et al. |
| 2024/0122641 A1 | 4/2024 | Frazier et al. |
| 2024/0315755 A1 | 9/2024 | Wolf et al. |
| 2024/0366286 A1 | 11/2024 | Wolf et al. |
| 2024/0423692 A1 | 12/2024 | Hester et al. |
| 2024/0423704 A1 | 12/2024 | Wolf |
| 2025/0009419 A1 | 1/2025 | Frazier et al. |

FOREIGN PATENT DOCUMENTS

| | | |
|---|---|---|
| CN | 101325919 | 12/2008 |
| CN | 101883606 | 11/2010 |
| CN | 103055417 | 4/2013 |
| DE | 102007006467 | 3/2008 |
| WO | 1999007299 | 2/1999 |
| WO | 1999030655 A1 | 6/1999 |
| WO | 2001043653 | 6/2001 |
| WO | 2003024349 | 3/2003 |
| WO | 2007037895 | 4/2007 |
| WO | 2007134005 | 11/2007 |
| WO | 2009048580 | 4/2009 |
| WO | 2010077980 | 7/2010 |
| WO | 2010077980 A1 | 7/2010 |
| WO | 2012174161 | 12/2012 |
| WO | 2013028998 A2 | 2/2013 |
| WO | 2014022436 A1 | 2/2014 |
| WO | 2015047863 | 4/2015 |
| WO | 2015048806 | 4/2015 |
| WO | 2015153696 | 10/2015 |
| WO | 2016183337 A2 | 11/2016 |

OTHER PUBLICATIONS

Dorville, Fabien. "Progress Bar." Behance, published May 3, 2013 (Retrieved from the Internet Jan. 30, 2020). Internet URL: <https://www .behance.net/gallery/8490779/Progress-bar> (Year: 2013).

Nesmiyanov, Nikita. "12 Open Source/Commercial Control Panels for Virtual Machines (VM's) Management." TecMint, published Jul. 28, 2016 (Retrieved from the Internet Feb. 19, 2020). Internet URL: <https://www.tecmint.com/opensource-commercial-control-panels-manage-virtual-machines/> (Year: 2016).

(56)        References Cited

OTHER PUBLICATIONS

Arora et al., "Cryodestruction of Vidian Nerve Branches," Indian J. Otolaryngology, vol. 32, No. 3, Sep. 1980, pp. 80-82.

Back et al., "Submucosal Bipolar Radiofrequency Thermal Ablation of Inferior Turbinates: A Long-Tenn Follow-up with Subjective and Objective Assessment," Laryngoscope, vol. 112, No. 10, Oct. 2002, pp. 1806-1812.

Banhiran et al., "Quality of life in patients with chronic rhinitis after radiofrequency inferior turbinate reduction," J. Med Assoc Thai, vol. 93, No. 8, 2010, pp. 950-957.

Bronzino, Medical Devices and Systems, The Biomedical Engineering Handbook (3rd ed. 2006), Chapter 63, Electrosurgical Devices, pp. 63-1-63-9.

Chen et al., "Preliminary study on radiofrequency thermocoagulation of the posterior inferior nerve, anterior ethmoidal nerve, and inferior turbinate under nasal endoscopy for the treatment of perennial allergic rhinitis," China Journal of Endoscopy, vol. 11, No. 3, Mar. 2005, pp. 239-240 and p. 243 (English Translation).

Chen et al., "Radiofrequency treatment of nasal posterior-under nerve, ethmoidal nerve and infraturbinal for perennial allergic rhinitis under nasal endoscope," China Journal of Endoscopy, vol. 11, No. 3, Mar. 2005, pp. 239-240 and p. 243 (English Translation).

Coste et al., "Radiofrequency is a Safe and Effective Treatment of Turbinate Hypertrophy," Laryngoscope, vol. 111, No. 5, May 2001, pp. 894-899.

Fang et al., "Nasal Endoscopy Combined with Multiple Radiofrequency for Perennial Allergic Rhinitis," J. First Mil Med Univ, vol. 25, No. 7, 2005, pp. 876-877 (English Translation).

Haemmerich, "Biophysics of Radiofrequency Ablation," Critical Reviews in Biomedical Engineering, vol. 38, No. 1, 2010, pp. 53-63.

Haikou, "Diagnostic Criteria and Efficacy Evaluation Criteria of Allergic Rhinitis," Otorhinolaryngol, vol. 33, No. 3, Jun. 1998, pp. 134-135.

Hong et al., "Radiofrequency Ablation: Mechanism of Action and Devices," J. Vasc. Interv. Radiol., vol. 21, No. 8S, 2010, pp. S179-S186.

Hytonen et al., "Radiofrequency Thermal Ablation for Patients with Nasal Symptoms: A Systematic Review of Effectiveness and Complications," Eur. Arch. Otorhinolaryngol, vol. 266, 2009, pp. 1257-1266.

Ilgner et al., "Feasibility of coblation versus laser resection in recurrent nasal polyps," Proc. of SPIE, vol. 5686, Apr. 25, 2005, pp. 322-327.

Kong et al., "Low-temperature plasma ablation of inferior turbinate for the treatment of perennial allergic rhinitis", J Clin. Otorhinolaryngol., vol. 19, No. 5, Mar. 2005, pp. 214-215 (English Translation).

Kong et al., "Clinical Observation on Radiofrequency Ablation Treatment in Perennial Allergic Rhinitis," J Clin. Otorhinolaryngol., vol. 19, No. 5, Mar. 2005, pp. 214-215 (English Translation).

Konno, "Historical, Pathophysiological, and Therapeutic Aspects of Vidian Neurectomy," Curr. Allergy Asthma Rep., vol. 10, 2010, pp. 105-112.

Koyyalagunta et al., Radiofrequency and Cryoablation for Cancer Pain, Techniques in Regional Anesthesia & Pain Management, vol. 14, No. 1, Jan. 2010, pp. 3-9.

Lee et al., "Surgical Management of Turbinate Hypertrophy in the Office: Three Mucosal Sparing Techniques," Operative Techniques in Ottolaryngology—Head and Neck Surgery, vol. 12, No. 2, Jun. 2001, pp. 107-111.

Levine, "Lasers in Endonasal Surgery," Otolaryngolog. Clinics of N. Am, June, vol. 30, No. 3, Jun. 1, 1997, pp. 451-455.

Liang et al., "Radiofrequency Treatment of Ethmoidal Nerve with Allergic Rhinitis Under Nasal Endoscopy," J. Clint Otorhinolaryngol., vol. 13, No. 8, Aug. 1999, pp. 341-342 (English Translation).

Philippson, "Principles of Electrical Resistance of Living Tissue," Bull. Cl. Sci. Acad. R. Belg., Ser. 5, vol. 7, No. 7, Jul. 1921, pp. 387-403.

Sackenheim, "Radio Frequency Ablation the Key to Cancer Treatment," J. Diagnostic Medical Sonography, vol. 19, No. 2, 2003, pp. 88-92.

Windsor et al., "Sphenopalatine Ganglion Blockage: A Review and Proposed Modification of the Transnasal Technique," Pain Physician, vol. 7, 2004, pp. 283-286.

Wolf, "How a Serial Entrepreneur Identifies and Evaluates Product Ideas and Brings Them to Market," Mastering Medical Device, Episode Transcript, 21 pages, Dec. 12, 2023 https://www.masteringmedicaldevice.com/episodes/wolf.

Buckley et al., "High-resolution spatial mapping of shear properties in cartilage," J Biomech., Mar. 3, 2010;43 (4):796-800, Epub Nov. 5, 2009.

Buckley et al., "Mapping the depth dependence of shear properties in articular cartilage," J Biomech., 41 (11):2430-2437, Epub Jul. 10, 2008.

Cole, "Biophysics of nasal airflow: a review," Am J Rhinol., 14(4):245-249, Jul.-Aug. 2000.

Cole, "The four components of the nasal valve," Am J Rhinol., 17(2):107-110, Mar.-Apr. 2003.

Fang et al., "Nasal Endoscopic Surgery Combined with Multisite Radiofrequency Technology for Treating Perennial Allergic Rhinitis," J First Mil Med Univ, vol. 25 No. 7, pp. 876-877, 2005.

Griffin et al., "Effects of enzymatic treatments on the depth-dependent viscoelastic shear properties of articular cartilage," J Orthop Res., 32(12):1652-1657, Epub Sep. 5, 2014.

Kjaergaard et al., "Relation of nasal air flow to nasal cavity dimensions," Arch Otolaryngol Head Neck Surg., 135 (6):565-570, Jun. 2009.

Liu et al., "Impact of radiofrequency thermocoagulation of bilateral vidian and anterior ethmoidal nerve cluster regions on nasal mucociliary transport function in perennial allergic rhinitis and vasomotor rhinitis," China Journal of Endoscopy, vol. 14, No. 11, 12 pages, Nov. 2008.

Silverberg et al., "Structure-function relations and rigidity percolation in the shear properties of articular cartilage," Biophys J., 107(7):1721-1730, Oct. 7, 2014.

Stewart et al., "Development and validation of the Nasal Obstruction Symptom Evaluation (NOSE) scale," Otolaryngol Head Neck Surg., 130(2):157-163, Feb. 2004.

Stupak, "A Perspective on the Nasal Valve," Dept. of Otorhinolaryngology, Albert Einstein College of Medicine, Nov. 6, 2009.

Stupak, "Endonasal repositioning of the upper lateral cartilage and the internal nasal valve," Ann Otol Rhinol Laryngol., 120(2):88-94, Feb. 2011.

International Search Report and Written Opinion for PCT/US2012/042316, mailed Aug. 24, 2012, 15 pages.

International Search Report and Written Opinion for PCT/US2014/054726, mailed Dec. 23, 2014, 5 pages.

International Search Report and Written Opinion for PCT/US2015/023742, mailed Jun. 29, 2015, 5 pages.

Singapore Search Report for Application Serial No. 201309238-2, mailed Apr. 17, 2014, 27 pages.

Supplementary European Search Report for Application No. 15772528, mailed Sep. 26, 2017, 7 pages.

Search Report in European Application No. 18204723.3 dated Feb. 18, 2019, 8 pages.

Extended European Search Report for Application No. 19199126.4, mailed Dec. 9, 2019, 6 pages.

Extended European Search Report for App. No. 19159707.9, mailed Nov. 9, 2019, 7 pages.

Extended European Search Report for App. No. 21172995.9, dated Jul. 9, 2021, 8 pages.

Extended European Search Report for App. No. 23177809.3, mailed Sep. 25, 2023.

* cited by examiner

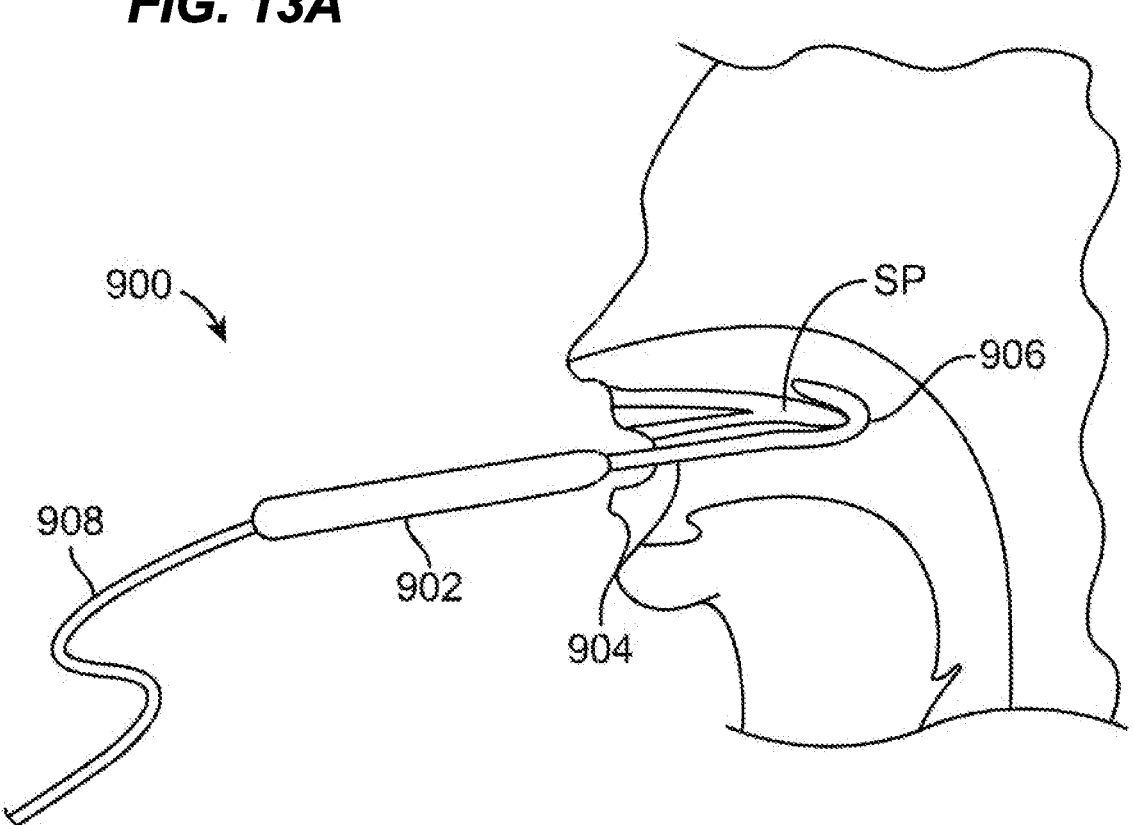
FIG. 13A
FIG. 13B
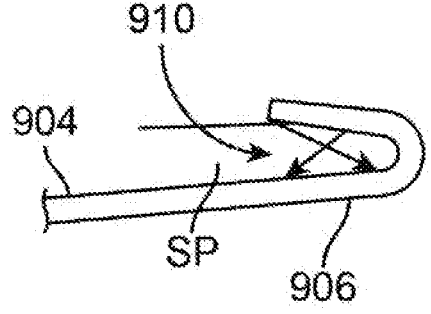

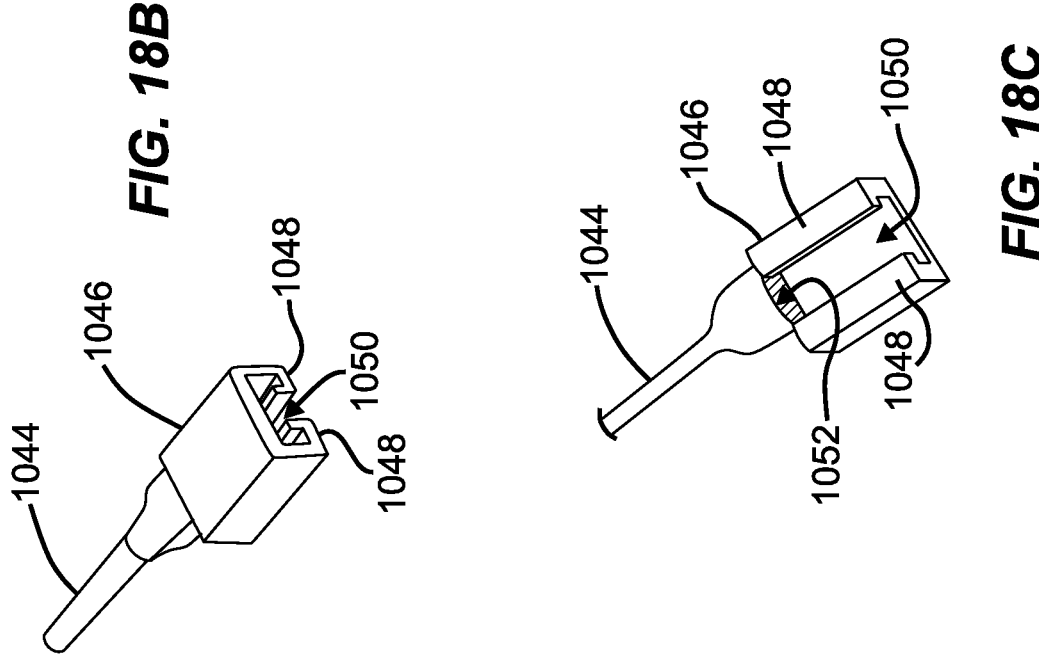
*FIG. 18B*
*FIG. 18C*
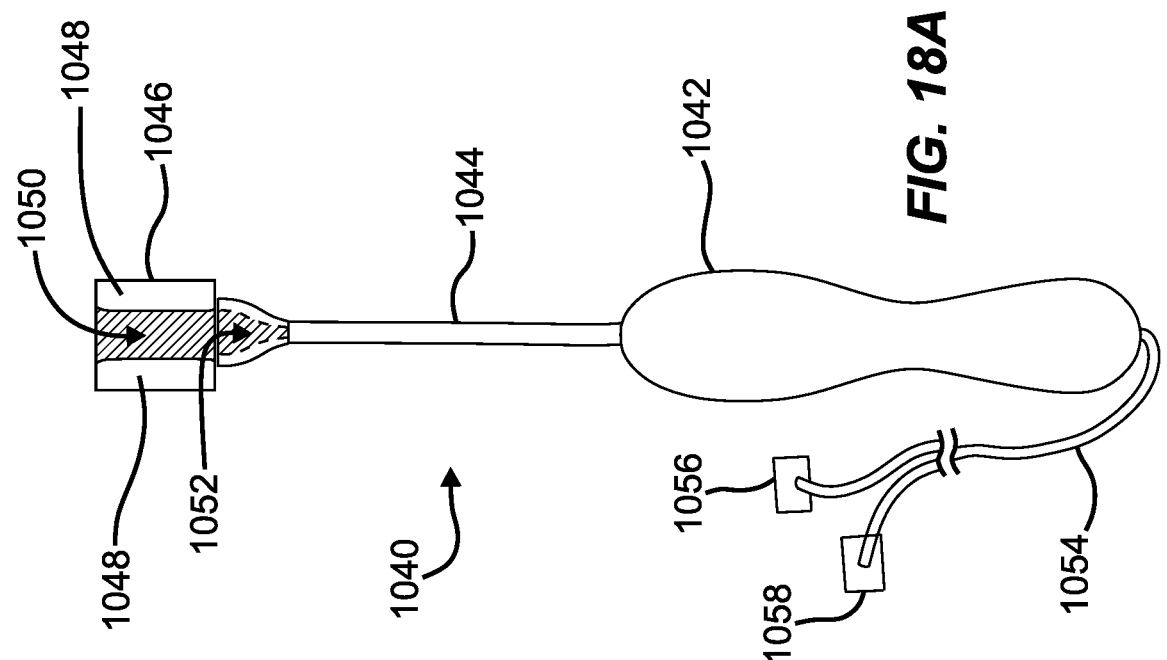
*FIG. 18A*

SOFT PALATE TREATMENT

TECHNICAL FIELD

This application relates generally to the field of medical devices and treatments. In particular, the application relates to systems, devices and methods for treating nasal airway tissue and/or nasopharyngeal soft tissue, including soft palate and possibly other parts of the mouth, to treat snoring and/or sleep apnea or to improve nose breathing.

BACKGROUND

Snoring and sleep apnea are extremely prevalent and significant health issues in the United States and other parts of the world. Sleep apnea is defined as the cessation of breathing during sleep. Obstructive sleep apnea (OSA) is the most common form of sleep apnea, and it is often linked to obesity, which is becoming an ever more prevalent health condition. OSA occurs when the tissues in the back of the throat repetitively collapse during sleep, producing snoring and complete airway blockage. This blockage creates pauses in breathing that occur repeatedly every night. In severe cases, these pauses in breathing can occur as frequently as every thirty seconds—i.e., many times each night. Alarmingly, the pauses can last up to a full minute.

The repetitive pauses in breathing during sleep in an OSA sufferer are accompanied by a reduction in blood oxygen levels and are followed by an arousal response. This response includes a release of substances into the bloodstream, which promotes elevation of blood pressure, inflammation, insulin resistance, and a disruption of the brain wave sleep pattern. The consequences of untreated sleep apnea include poor quality sleep, excessive daytime fatigue and sleepiness, irritability, hard-to-control high blood pressure and diabetes, heart disease and stroke. Moreover, untreated sleep apnea may be responsible for job impairment and motor vehicle crashes.

Snoring, which is typically a less serious and severe condition than sleep apnea, still has significant effects on people who suffer from it and their loved ones. Snoring can affect a person's sleep and of course can also disrupt the sleep of a spouse, sibling or others who are sleeping nearby.

Many different methods and devices have been developed and tested for treating sleep apnea and snoring, but no perfect solution has yet been discovered. Some treatments for sleep apnea involve major, invasive surgery, for example to remove portions of the tongue and/or throat or to place mechanical slings or other implants in the tongue, in an effort to prevent the tongue from falling back in the mouth during sleep. Some patients wear continuous positive airway pressure (CPAP) masks for sleeping, but those devices are obtrusive, loud and uncomfortable, making sleeping difficult and leading to poor patient compliance. Less invasive techniques, such as wearing an adhesive nasal strip to bed each night, are usually less effective or do not work at all, since many OSA patients are either already mouth breathers or convert to mouth breathing when a nasal blockage is addressed.

In addition to sleep apnea and snoring, simply breathing through the nose is difficult for many people. Difficulty nose breathing may be caused by a number of factors, including a deviated nasal septum, inflamed or enlarged nasal turbinates, nasal valve collapse and/or other issues. A number of devices and methods have been developed to address nasal airway breathing, but improvements would still be desirable.

Therefore, it would be highly advantageous to have improved systems, devices and methods for treating sleep apnea and snoring, as well as for improving nasal breathing. Ideally, these improved systems, devices and methods would be relatively less invasive than most of the surgical techniques used currently or tried in the past, while still working effectively for many patients. Also ideally, the improved techniques would not involve implants. The present disclosure will address at least some of these objectives.

BRIEF SUMMARY

Embodiments of the present application are directed to devices, systems and methods for treating soft tissue in the nose and/or nasopharynx, such as the soft palate and possibly other areas of the mouth and/or throat, to treat sleep apnea and/or snoring or improve nasal breathing. Various embodiments may be used to reshape, remodel, strengthen, stiffen, shrink and/or otherwise change properties of tissues of the soft palate (or other soft tissue), including but not limited to skin, muscle, mucosa, submucosa, cartilage, fat, blood vessels and nerves. For example, treatments may include tissue shrinkage, fat reduction, scar formation, muscle stiffening, collagen production/stimulation, etc. Treatment of the soft palate may prevent collapse and/or vibration of the soft palate during nighttime breathing and thus prevent or at least reduce OSA and/or snoring.

According to one aspect of the present disclosure, a method of treating a soft palate in a patient to treat sleep apnea, snoring or both may involve advancing a treatment element of a treatment device through the patient's mouth, contacting a treatment surface of the treatment element with the soft palate, delivering energy to the soft palate via one or more energy delivery members on the treatment surface, and removing the treatment element from the mouth. In some embodiments, the energy delivery members are two rows of bipolar, radiofrequency electrode pairs protruding from the treatment surface, and delivering the energy involves delivering radiofrequency energy between the two rows of electrode pairs, to reshape, remodel, strengthen and/or change a property of the soft palate.

In some embodiments, the method may also involve applying force against the soft palate with the treatment surface to at least temporarily deform tissue of the soft palate. Some embodiments may also involve forming an incision in mucosal tissue of the soft palate, in which case the energy may be delivered to submucosal tissue. The type of delivered energy may be radiofrequency (monopolar or bipolar), microwave, ultrasound, heat, cryogenic energy (energy removal) or the like. The method may also involve repositioning the treatment element to a new location on the soft palate and repeating the delivering step, before removing the treatment element from the mouth. This may be repeated as many times as desired, to cover a given area of the soft palate.

Optionally, some embodiments may also include injecting a substance into the soft palate before applying energy to the tissue. For example the substance may be an agent that increases conductivity of the tissue or enhances softening, stiffening or other tissue changes. Such an injection may be performed using conventional techniques and device, such as a syringe, or alternatively a treatment device may include a built-in injection device.

In another aspect of the disclosure, a device for treating a soft palate in a patient to treat sleep apnea, snoring or both may include a handle, a shaft, a treatment element, and a connector for connecting the handle with a power source.

The shaft may include a distal end with a neck, and the treatment element may extend from the neck and may be angled relative to a longitudinal axis of the shaft. The treatment element may include a treatment surface and at least one energy delivery member on the treatment surface. In some embodiments, the energy delivery member comprises two rows of bipolar, radiofrequency electrode pairs protruding from the treatment surface. The electrodes may be triangular in shape, for example. In some embodiments, the treatment surface has a convex shape for creating a concave deformity in the soft palate. In some embodiments, the device may have multiple shafts and multiple treatment elements, where each of the treatment elements is located on one of the multiple shafts.

In another aspect of the present disclosure, a method of treating a soft palate in a patient may involve advancing a tissue treatment portion of a soft palate treatment device through the patient's mouth, contacting a treatment surface of the tissue treatment portion with mucosal tissue of the soft palate, and delivering energy from the tissue treatment portion through the mucosal tissue to a target tissue in the soft palate beneath to the mucosal tissue, to change at least one property of the target tissue. The method may further involve cooling the mucosal tissue with a cooling member on the treatment surface of the tissue treatment portion and removing the tissue treatment portion from the mouth. In some embodiments, the change in the at least one property of the target tissue results in a reduction of at least one of snoring or sleep apnea in the patient.

In some embodiments, the tissue treatment portion includes two rows of bipolar, radiofrequency electrode pairs on the treatment surface, and delivering the energy involves delivering radiofrequency energy between the two rows of electrode pairs. The method may optionally further involve applying force against the soft palate with the treatment surface while delivering the energy, to deform tissue of the soft palate. In such embodiments, changing the at least one property of the target tissue may involve reshaping the target tissue. In various embodiments, changing the at least one property of the target tissue may involve at least one of reshaping, remodeling, stiffening, strengthening, tightening, shortening, thickening or ablating the target tissue.

According to various embodiments, the delivered energy may be radiofrequency, microwave, ultrasound, heat or cryogenic energy. Optionally, the method may further involve repositioning the tissue treatment portion to a new location on the soft palate and delivering energy to the target tissue again, to form a treatment pattern in the target tissue. In some embodiments, cooling the mucosal tissue involves applying a suction force with the cooling member to suction air through the cooling member. In alternative embodiments, cooling the mucosal tissue involves circulating a cooling fluid through the cooling member.

Optionally, the method may further involve measuring a temperature of the mucosal tissue with a temperature sensing member on the treatment surface of the tissue treatment portion. In various embodiments, the target tissue may be one or more of muscle, cartilage, tendon, ligament, connective tissue, nerve or blood vessel. In one embodiment, the tissue treatment portion is hook-shaped, and contacting the treatment surface involves contacting a superior surface and an inferior surface of the soft palate. Optionally, the method may further include bending a malleable shaft of the soft palate treatment device before advancing the tissue treatment portion. The method may also further involve applying force to the mucosal tissue with the tissue treatment portion to cause the tissue treatment portion to flex at at least one flex point along the tissue treatment portion.

In another aspect of the present disclosure, a device for treating a soft palate in a patient may include a handle, a shaft having a proximal end attached to the handle and a distal end, an elongate treatment element extending from the distal end of the handle, and a connector for connecting the handle with a power source. The elongate treatment element may include a treatment surface, at least two energy delivery members on the treatment surface, and a cooling member on the treatment surface between the at least two energy delivery members.

In some embodiments, the distal end of the shaft has a neck that is angled relative to a longitudinal axis of the shaft, and the elongate treatment element is attached to the neck. In some embodiments, the at least two energy delivery members are two elongate bipolar radiofrequency electrodes. Alternatively, the at least two energy delivery members may be two parallel rows of multiple bipolar radiofrequency electrodes. In some embodiments, each of the radiofrequency electrodes is a protruding, non-penetrating electrode. In some embodiments, the treatment surface has a convex shape for creating a concave deformity in the soft palate.

In some embodiments, the cooling member may include at least one suction port for suctioning air through the cooling member to cool mucosal tissue in contact with the cooling member. In alternative embodiments, the cooling member may include a channel for circulating cooling fluid through the cooling member to cool mucosal tissue in contact with the cooling member. In some embodiments, the elongate treatment element has a hook shape, and the treatment surface is configured to contact a superior surface and an inferior surface of the soft palate. In some embodiments, the shaft is malleable. Optionally, the device may include at least one flex member on a top surface of the elongate treatment element. Also optionally, the device may include a temperature sensing member on the elongate treatment element, for sensing a temperature of mucosal tissue in contact with the treatment surface.

These and other aspects and embodiments are described further below, in relation to the attached drawing figures.

BRIEF DESCRIPTION OF DRAWINGS

FIG. 13A is a side, cross-sectional view of a human head and a side view of a soft palate tissue treatment device, illustrating a method for using the device, according to one embodiment;

FIG. 13B is a close-up view of a distal portion of the device of FIG. 13A and the soft palate;

FIG. 18A is a bottom view of a soft palate treatment device with cooling capabilities, according to one embodiment;

FIGS. 18B and 18C are top perspective and bottom perspective views, respectively, of a distal portion of the soft palate treatment device of FIG. 18A;

DETAILED DESCRIPTION

Figure 1:
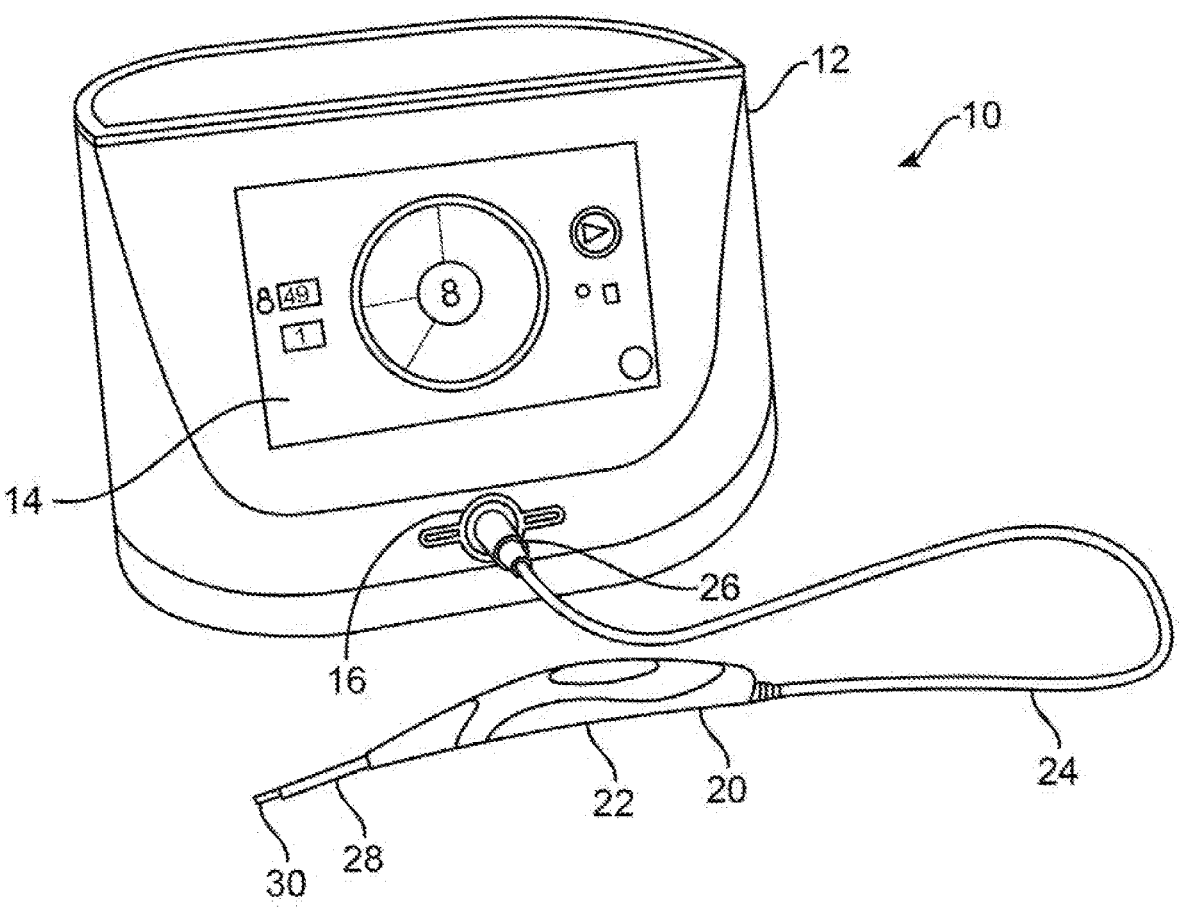
FIG. 1 is a perspective view of the VivAer® Nasal Airway Remodeling System (Aerin Medical Inc., www.aerinmedical.com), which in some embodiments may be used or adapted for use in treating soft palate tissues.

The assignee of the present application has developed a number of devices, systems and methods for delivering energy to tissues in the nasal passages to treat nasal valve insufficiency, chronic nasal congestion, post nasal drip, chronic cough, rhinitis, and other breathing abnormalities and disorders of the nasal passages. The systems generally include an energy delivery and control console (or "box") and a hand piece (or "stylus") for delivering the therapy to the nasal tissue. The hand piece typically includes a handle, a shaft, and a treatment delivery element at or near the end of the shaft for delivering the energy to the tissues. One general type of embodiment includes one handle, one shaft and one treatment element for advancing through a nostril. Another general type of embodiment includes a clamp-like configuration, with two handles, two shafts and two treatment elements, where tissue is clamped between the two tissue elements, which are either advanced through both nostrils or through one nostril and outside of the nose. Various embodiments may include a clamp with only one active element on one side, alternating and/or intermittent top/bottom electrodes dispersed across the treatment elements, etc. In some embodiments, the method of treatment involves applying force to a tissue to be treated with the treatment element, in some cases to deform the tissue, and applying energy to the tissue with the treatment element. When the treatment is stopped and the treatment element is removed, the target tissue is reformed and/or changed in some other way (ablated, shrunken, stiffened, reduced, etc.) and retains at least some of that change after the treatment is complete. In one embodiment, the treatment element delivers radiofrequency (RF) energy (bipolar or monopolar, in different embodiments) from multiple electrodes on the treatment element, although many other energy modalities and treatment element configurations are possible.

Patents describing various embodiments of these tissue treatment devices, systems and methods include U.S. Pat. Nos. 8,936,594; 8,986,301; 9,072,597; 9,179,964; 9,179, 967; 9,237,924; 9,415,194; 9,433,463; 9,433,463; 9,452, 010; 9,486,278; 9,526,571; 9,687,296; 9,788,886; 9,801, 752; 9,888,957; 9,913,682; 9,943,361; 10,028,780; 10,265, 115; 10,335,221; 10,376,300; 10,398,489; 10,456,185; 10,456,186; 10,470,814; 10,485,603; 10,603,059; 10,631, 925; 10,722,282; 10,779,873; 10,864,035; 10,932,853; 11,033,318; 11,116,566; D880,694; D881,904; and D902, 412. All of these patents, referred to herein as "the Incorporated Patents," are hereby incorporated by reference herein in their entireties. Any of the embodiments described in the Incorporated Patents may be used or adapted for use in treating the soft palate and/or other mouth or throat structures to treat OSA and/or snoring. The many embodiments of methods, devices and systems described in the Incorporated Patents will not be repeated in this application, but any embodiments described in those patents may be used or adapted for use in performing the methods described herein for treating OSA and/or snoring.

Any of the device and method embodiments below may be used for treating soft palate tissue to help ameliorate or in some cases eliminate snoring, sleep apnea or both. In some embodiments, the devices and methods may be used to treat one or more tissues other than the soft palate, such as but not limited to tissue of the hard palate, tongue (tongue base, etc.), uvula, pharynx, throat, and nasal cavity. Any one or more of these tissues may be treated in addition to or as an alternative to treating soft palate, in various embodiments. Treatment devices and methods may be directed at shrinking, stiffening, ablating, reducing volume of, contracting and/or otherwise changing one or more properties of tissue of the soft palate and/or other structures. Tissues that may be treated include, but are not limited to, skin, muscle, mucosa, submucosa, cartilage, fat, blood vessels and nerves. In some embodiments, treatment tissue may also include bone, such as when thin bone underlying mucosa is altered. Additionally, any of the embodiments herein may be used, or adapted for use, in treating nasal airway tissues to improve nasal breathing or address any other issues within the nasal cavity. Therefore, although the following description is focused primarily on treatment of the soft palate, this is but one example of a target treatment structure, and any embodiment described herein may be used or adapted for use in treating any other suitable structure(s) or tissue(s), such as but not limited to those listed above. For the sake of brevity, this application will not repeat for each embodiment the list of all treatable tissues, anatomical regions and conditions, but any embodiment described herein may be used or adapted for use in the ways discussed immediately above and is not limited to soft palate treatment.

Referring now to FIG. 1, a perspective view of the VivAer® Nasal Airway Remodeling System 10 (or "treatment system 10"), patented by the assignee of the present application, is illustrated. (See www.aerinmedical.com.) Treatment system 10 includes a console 12 (or "energy source") and a stylus 20 (or "treatment device," "treatment member" or the like). Similarly, the various embodiments of the soft palate treatment system described below also include a console and stylus. Furthermore, in some embodiments, treatment system 10 may be used (or adapted for use) to treat soft palate tissue. For example, in some embodiments, stylus 20 of FIG. 1 may be used to treat soft palate tissue, while in alternative embodiments, a different stylus, designed specifically for treating soft palate tissue, may be used with console 12. In the illustrated embodiment, treatment system 10 is designed to deliver bipolar radiofrequency (RF) energy, but in alternative embodiments, system 10 may be designed to deliver monopolar RF, ultrasound, microwave, laser, heat, electrical, chemical, pharmaceutical and/or any other type of energy or combination of energy modalities. Alternative embodiments may be designed to remove energy, via cryogenic therapy or other cooling techniques. Console 12 generally includes a housing with a display 14, an outlet 16 for plugging in stylus 20, and a power cord (not shown) for connecting with a power source (e.g., a wall outlet). A detailed description of the console 12 may be found in U.S. patent application Ser. No. 16/668, 678, filed Oct. 30, 2019 (Pub. No. 2020/0129223), which is hereby incorporated by reference and included as one of the Incorporated References.

Stylus 20 generally includes a handle 22, a cable 24, an adapter 26, a shaft 28 and a treatment element 30. Details of various embodiments of stylus 20 will be described below and are further described in the Incorporated Patents. To adapt treatment system 10 for use in the soft palate, one or more of a number of different alterations may be made to system 10. For example, shaft 28 could be made longer, could be made malleable for angle adjustment, or could be pre-formed with an angle or bend. Treatment element 30 could be made longer and/or wider, could be made to have a different overall shape and/or could be angled relative to shaft 28. Treatment algorithms designed into console 12 may be configured especially for soft palate treatment. These and/or other changes may be made to system 10, to enhance its ability to treat soft palate tissue, according to various alternative embodiments.

Figure 2:
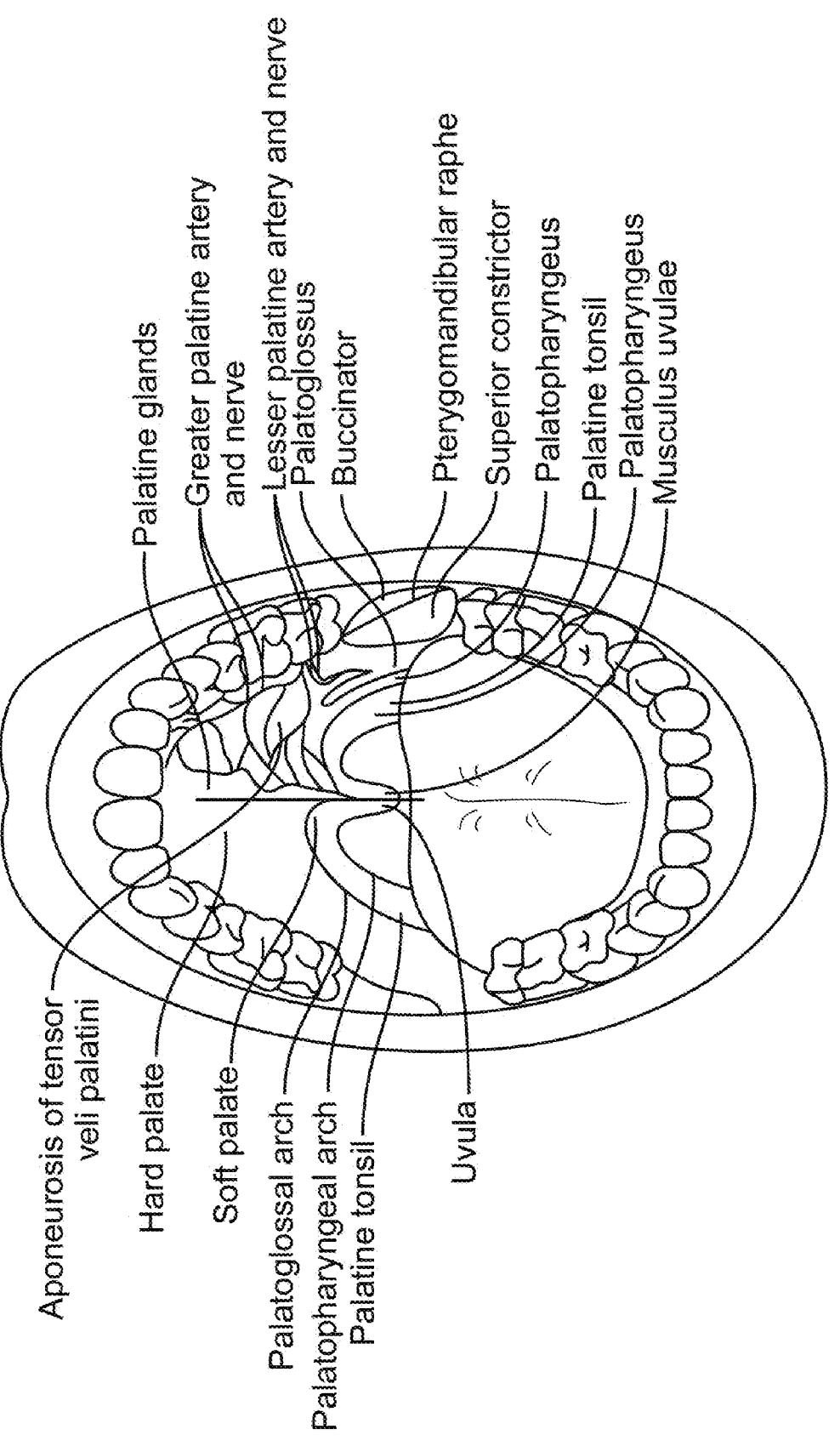
FIG. 2 is a front view of an open mouth, with mucosal tissue along one side of the hard palate and the soft palate removed, to show various structures of the hard and soft palate.
Figure 3:
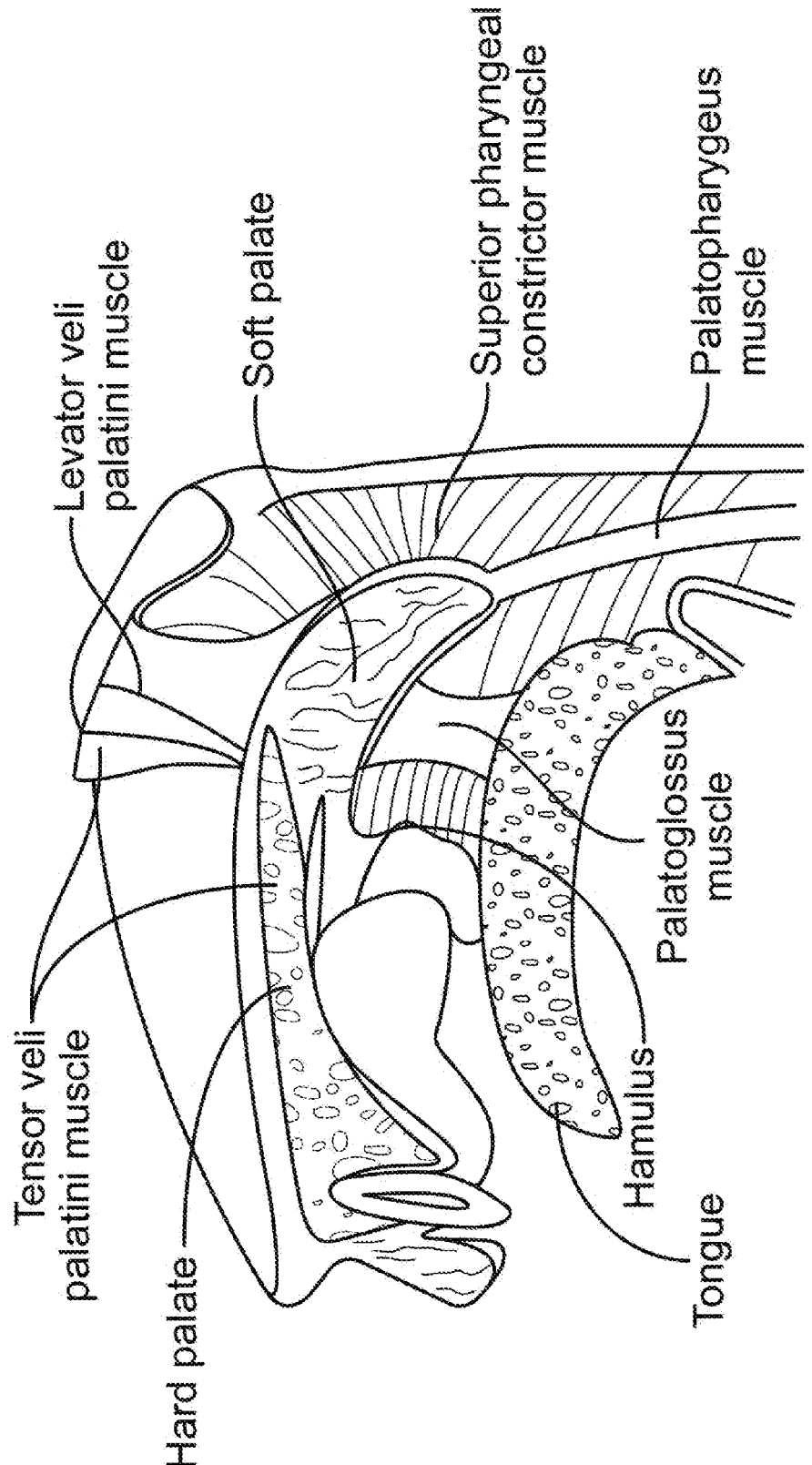
FIG. 3 is a side, cross-sectional view of a portion of a mouth, showing the various muscles that make up the soft palate.

Referring now to FIGS. 2 and 3, two anatomical drawings of the soft palate are provided. FIG. 2 is a front view of an open mouth. FIG. 3 is a lateral, cross-sectional view of a portion of an oral cavity, illustrating the soft palate. As can be seen in both figures, the hard palate extends from the top teeth posteriorly and medially, toward the back of the mouth. The soft palate extends in a posterior direction from the hard palate. As best seen in FIG. 2, the uvula extends from the middle of the posterior edge of the soft palate, and the tonsils are located near the lateral edges of the soft palate on both sides. The soft palate is made up of five muscles, covered in mucosal tissue, which play important roles in swallowing and breathing. As best seen in FIG. 3, the five muscles of the soft palate are the tensor veli palatini, the palatoglossus, the palatopharyngeus, the levator veli palatini, and the *musculus* uvulae (FIG. 2). These muscles work together to suspend and move the soft palate as needed, to facilitate breathing, swallowing and sneezing.

In some patients with sleep apnea, the palatopharyngeus muscle tends to collapse into the airway. One treatment that has been described for sleep apnea is a surgical procedure, in which the surgeon cuts each of the two palatopharyngeus muscles at the bottom, pulls them up and forward, and stitches them to the upper lateral edges of the pharynx. This acts like a sling for the soft palate. Although this surgery may work well in some patients, it requires general anesthesia and involves an invasive surgical procedure with painful post-surgical recovery.

Methods and devices described below for treating the soft palate may work by stiffening, strengthening, tightening, shortening, ablating and/or otherwise changing any property or properties of one or more of the tissues (muscle, mucosa, cartilage, fat, nerve, etc.) that make up the soft palate. In some embodiments, for example, energy may be directed at one or more of the muscles that make up the soft palate, to change one or more properties of the muscle and thus treat the soft palate in a way that ameliorates sleep apnea and/or snoring. For example, in various embodiments, the palatopharyngeus muscles may be tightened, stiffened, shortened and/or strengthened, to mimic the surgical procedure described immediately above. In other embodiments, an energy delivery procedure may be directed at the levator veli palatini muscle, instead of the palatopharyngeus. Different muscles or groups of muscles may be treated, according to different embodiments. In yet other embodiments, alternative or additional types of tissues may be targeted, such as nerve or mucosa.

According to various embodiments, some of which are described further below, a treatment of the soft palate may involve delivery of energy to tissue, removal of energy from tissue (e.g., cryotherapy or other cooling techniques), and/or application of pressure to tissue. In embodiments where energy is delivered, the form of energy may be any suitable form, such as but not limited to radiofrequency (RF), heat, electrical, ultrasound, microwave, laser, chemical or the like. In embodiments where energy is removed, any form of cryotherapy or other cooling technique may be used. In addition to energy delivery, some embodiments involve applying pressure to tissue with the treatment element of the treatment device. In many embodiments, the same treatment element used for delivering (or removing) energy will be used for applying pressure. Alternatively, separate components of a device may deliver energy and apply pressure. The pressure applying treatment element may have a shape designed to confer a corresponding shape to the tissue being treated. For example, in some embodiments the tissue treatment surface of the treatment element may have a convex shape, which gives a target tissue a concave shape when pressed against it. Using a shaped treatment element to temporarily change a shape of a target tissue and then delivering energy to (or removing energy from) the target tissue while in the changed shape, may cause a permanent reshaping of the tissue after the treatment is completed. In alternative embodiments, however, little or no pressure may be applied, and energy delivery (or removal) may work by itself on the target tissue(s) to achieve the desired result. These techniques and variations thereon are described further below.

Referring now to FIGS. 4A-4G, further details of one embodiment of a treatment device 550 (or "stylus") will now be described. Further detail may also be found in the Incorporated Patents. Treatment device 550 may be compatible for use with console 12 of FIG. 1 or any other suitable console device. Treatment device 550 may include a handle 560, a shaft 558, and a treatment element 552 that is attached to (or simply a distal portion of) a distal tip 556 of device 550. Treatment element 552 may be provided on an enlarged distal tip 556 of elongate shaft 558, and as in the embodiment illustrated, may have a convex shape configured to press against and create a concavity in the soft palate tissue, such as cartilage and mucosa. Treatment element 552 may include two rows of protruding RF electrodes 554 and a thermocouple 555 (best seen in FIGS. 4D and 4G). In this embodiment, electrodes 554 are shown as needle electrodes, but in alternative embodiments, electrodes 554 may be protruding but not piercing, for example semicircular bumps, bumps having other shapes such as rectangular or triangular, ridges having any suitable shape and/or pattern, or the like. Other embodiments may include non-protruding electrodes that are flat and/or flush with the tissue contact surface of the treatment element 552. Thus, in various embodiments, electrodes 554 may deliver energy directly to mucosal tissue, to one or more tissues underlying the mucosal tissue, or both. The underlying tissue may be cartilage, nerve, muscle, blood vessel, fat, any combination thereof, or any other suitable tissue.

Handle 560 may include an input control, such as a power button 562, on its front side, which may be used to activate and deactivate treatment element 522. Power button 562 may be positioned in a recess of the handle to allow for finger stability when activating and deactivating the electrode. In other embodiments, the input control may be alternatively or additionally provided in the form of a switch, dial or foot pedal.

Treatment device 550 may either include a generator or be connected to a remote generator. Treatment device 550 may include a flexible wire or cable 564 that connects to an adaptor 566 that is configured to be plugged into a remote generator (not shown). Adaptor 566 may allow transmission of treatment energy between a remote generator and treatment device 550. Adaptor 566 may also allow transmission of any sensor signals between treatment device 550 and a generator or control unit. Treatment device 550 may be provided in a system or kit, including a console (or "generator," "remote generator" or the like (as illustrated in FIG. 1)). The system or kit (with or without the remote generator) may also include a grounding device and/or a cooling device. In some embodiments, the kit includes a positioning element (e.g., a "cottle" device) configured to help a user locate the optimal treatment area.

In various embodiments, shaft 558 has a diameter of about 0.2 inch to about 0.5 inch and a length of about 1.5 inches to about 6 inches. In some embodiments, the shaft and/or handle is made of a polymer, such as polycarbonate or PEEK. In other embodiments, the shaft is made of stainless steel or other metals. The metals may be coated with an external and/or internal insulating coating (e.g., polyester, polyolefin, etc.). Handle 560 may be made of the same material as shaft 558, in some embodiments. In some embodiments, the shaft 558 is rigid. This may allow a user of treatment device 550 increased control over the deformation of soft palate tissue. In other embodiments, shaft 558 may be flexible or malleable. A malleable shaft 588 allows a user to adjust an angle of distal tip 556 by bending shaft 558. In some embodiments, the tip-to-shaft angle may be adjustable by way of a locking hinge or other similar mechanism. In some embodiments, distal tip 556 may be flexible or pre-curved along its length, so that it better conforms to the tissue of the soft palate. Deformability may also be provided by the geometry of the device, in addition to materials. For instance, laser cutting slots into distal tip 556 and/or the shaft 558 may allow the remaining sections of metal to plastically deform.

Figure 4A:
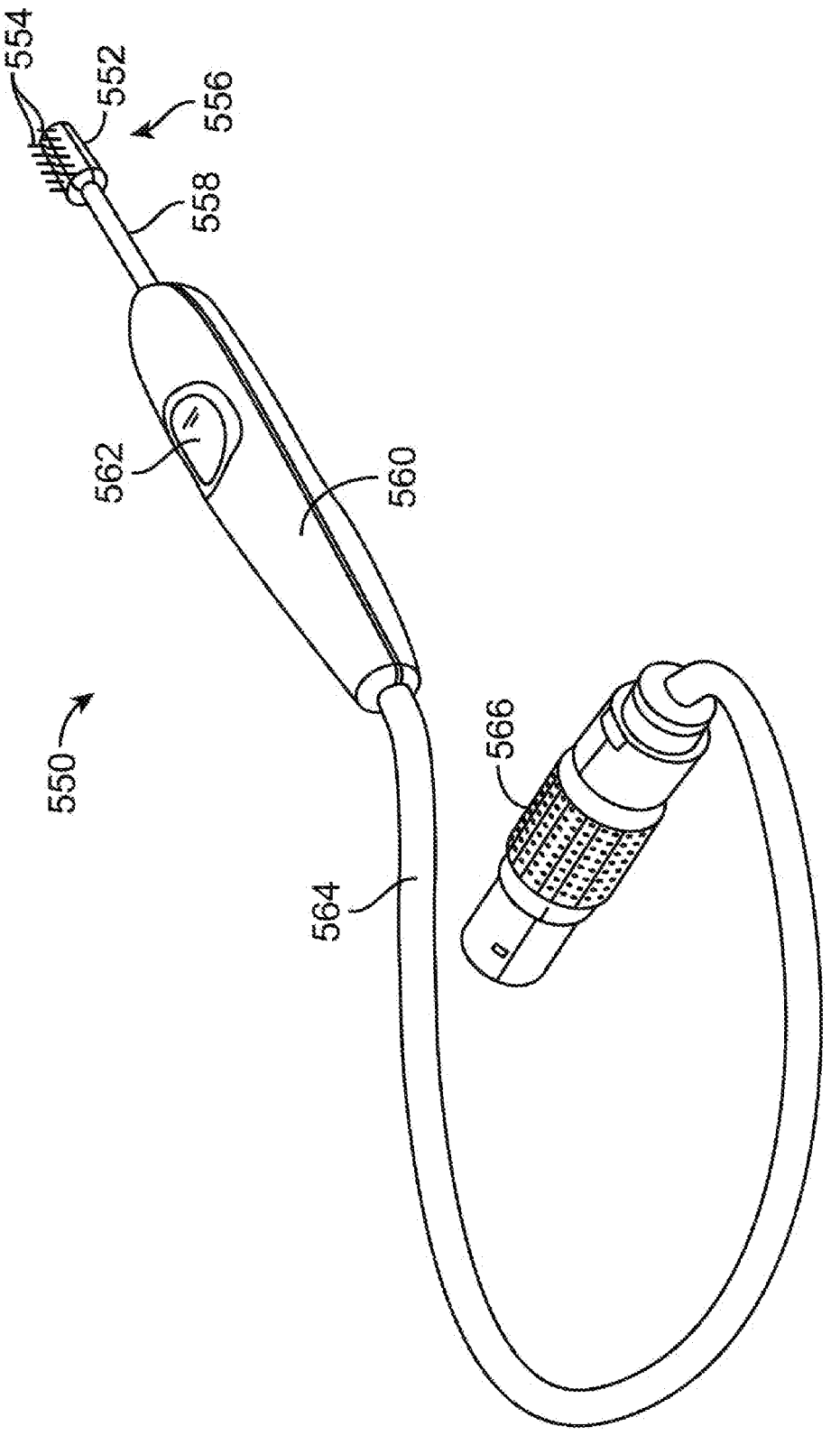
FIGS. 4A-4G are various views of a device for applying energy to the soft palate for treating OSA and/or snoring, according to one embodiment.
Figures 4B, 4C:
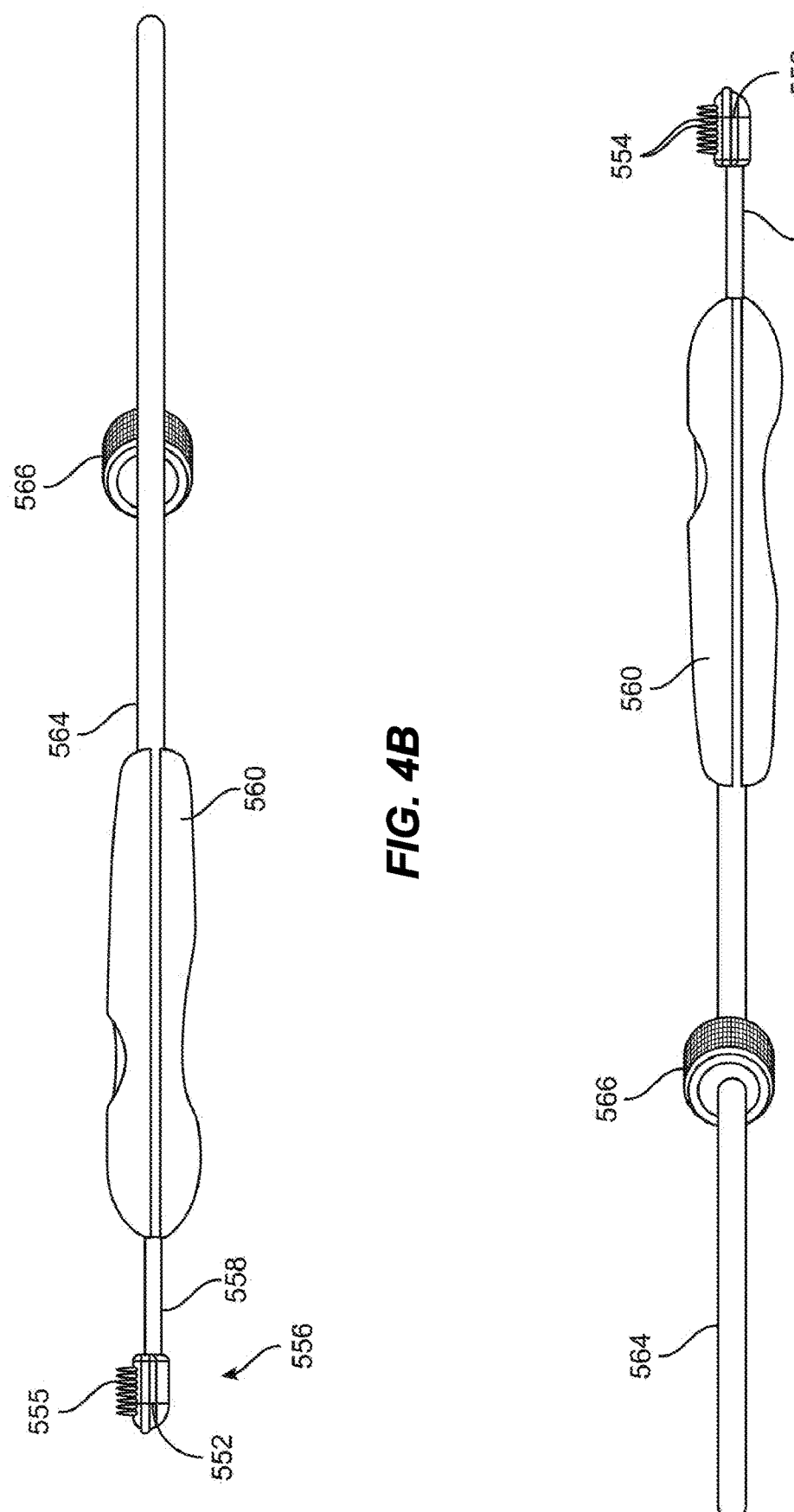
Figure 4D:
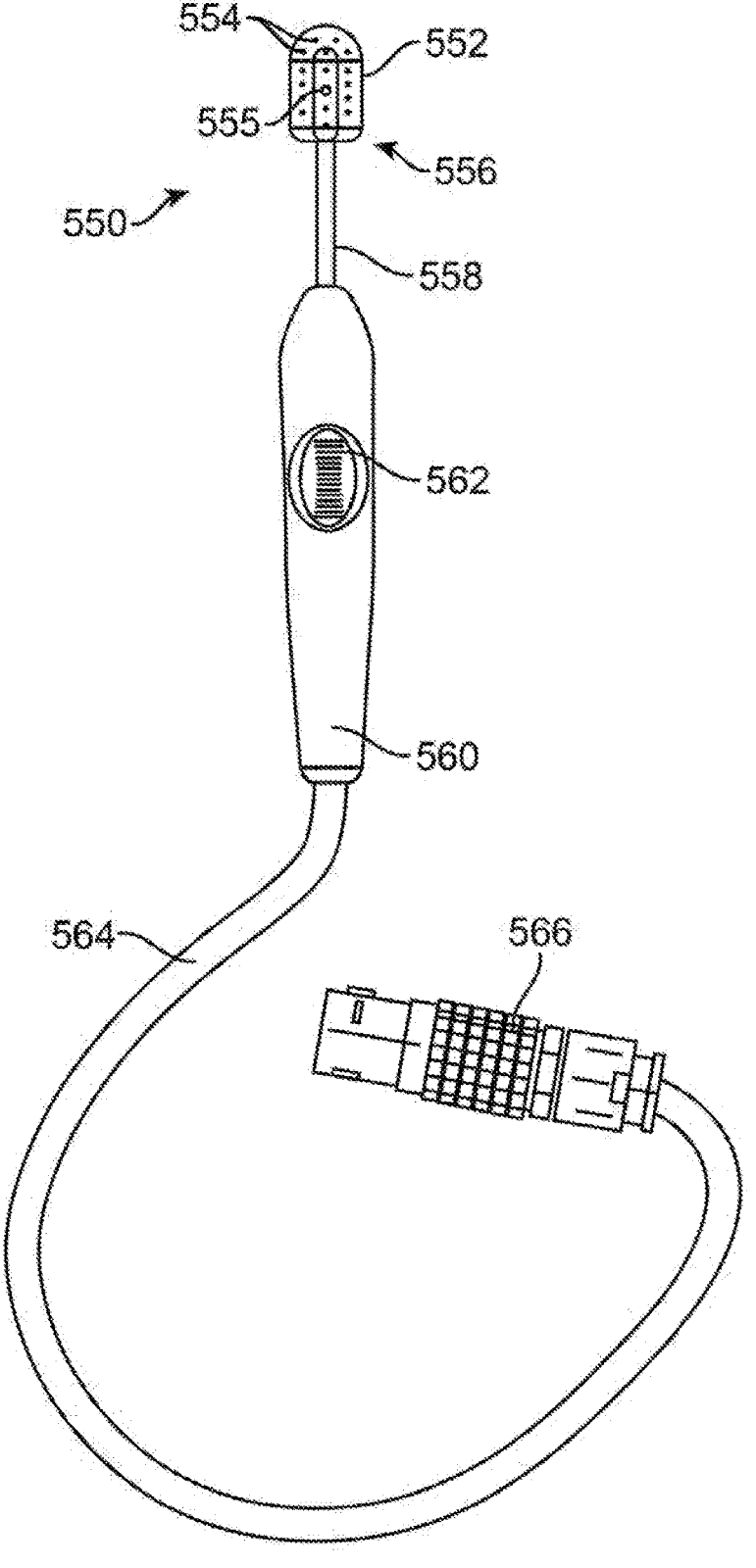
Figure 4E:
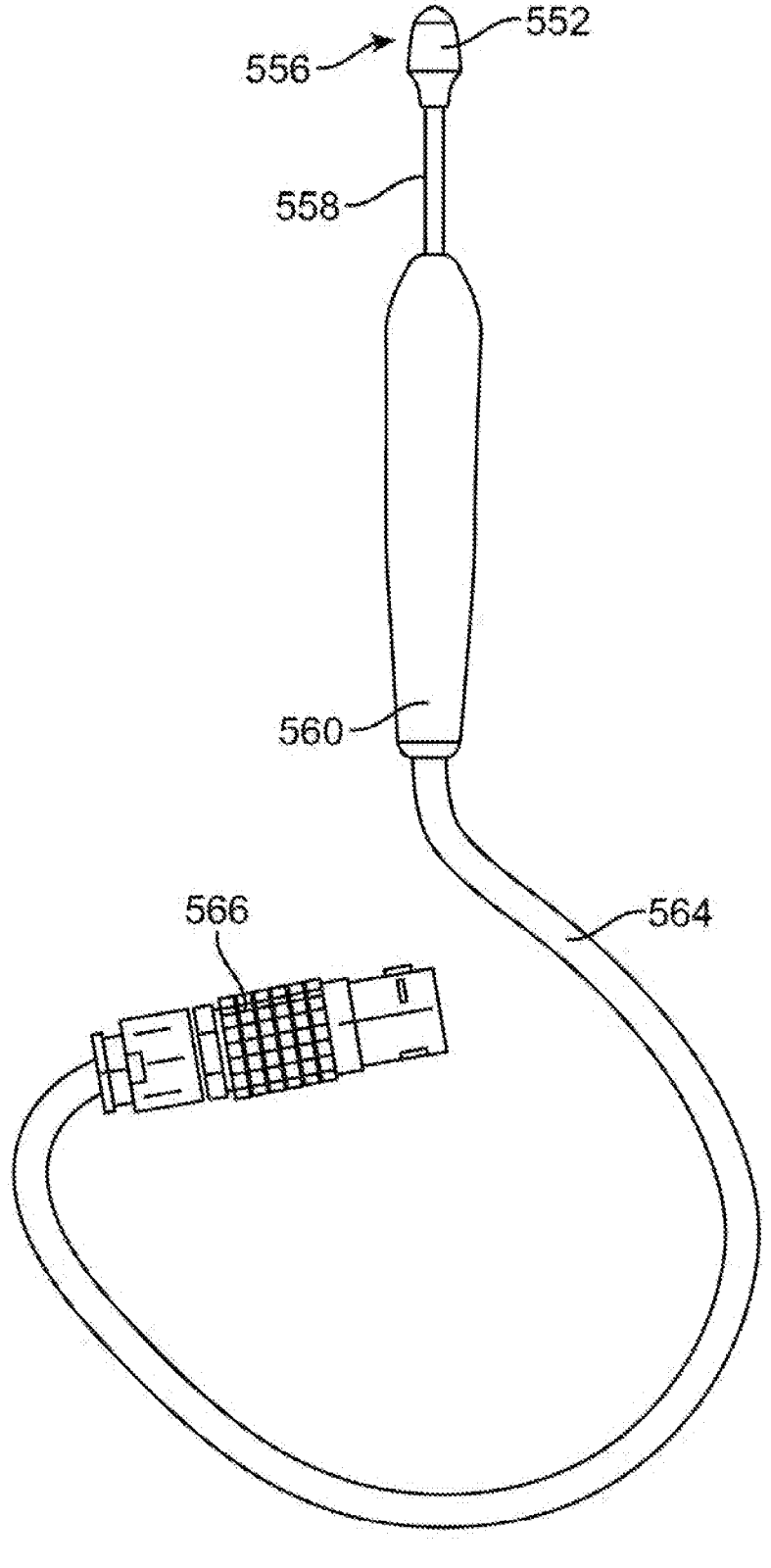
Figure 4F:
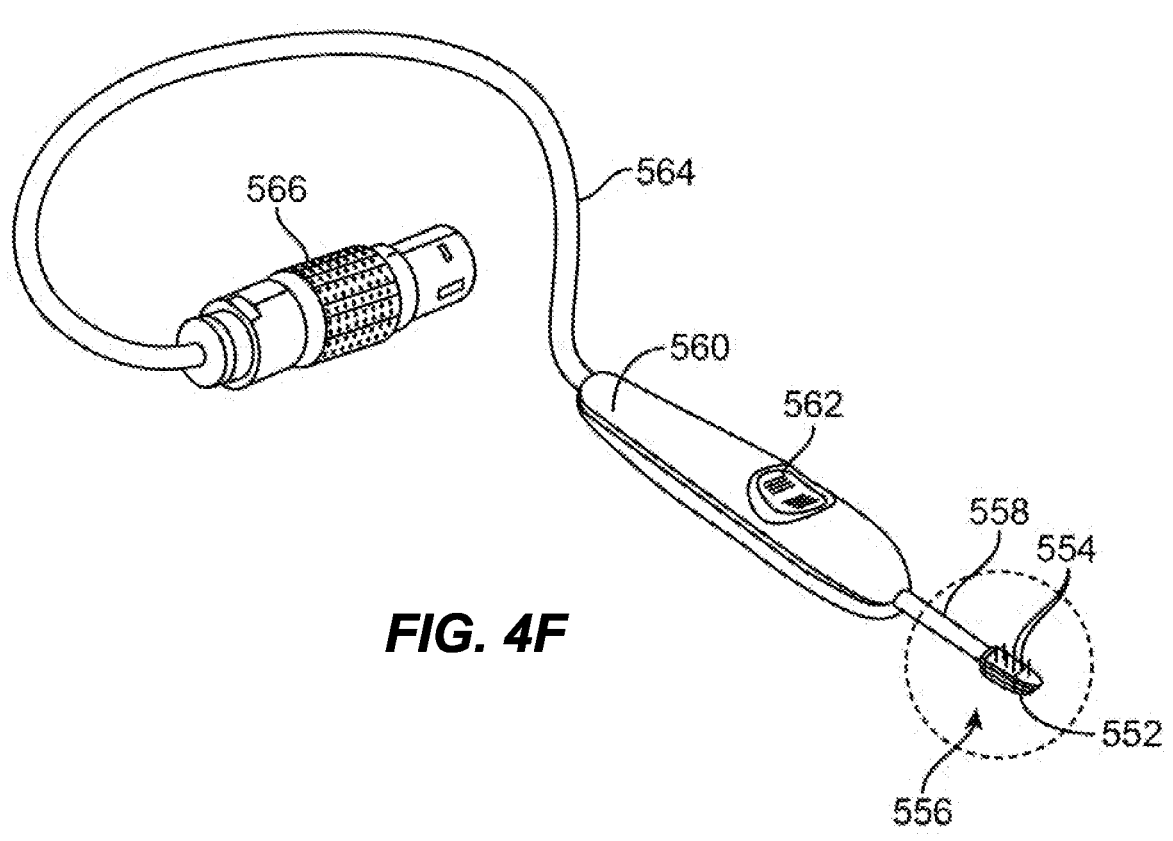

FIGS. 4B and 4C depict side views of treatment device 550. FIGS. 4D and 4E depict front and back views, respectively, of treatment device 550. As shown in FIGS. 4D and 4E, handle 560 generally comprises a rounded elongate shape. Other shapes are also possible. For example handle 560 may have a rectangular or square-shaped cross section. In some embodiments, a circumference (or width or cross-sectional area) of handle 560 may increase distally along the length of handle 560.

Figure 4G:
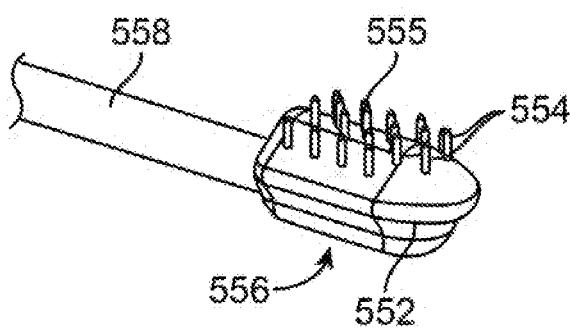

FIG. 4G depicts a larger view of distal tip 556 of device 550. As shown best in FIG. 4G, treatment element 552 comprises a generally elongate shape. The front (or "tissue contact surface") of treatment element 552 comprises a shallow curved surface, providing a convex shape configured to deform the soft palate tissue and create a concavity therein. In alternative embodiments, the front of treatment element 552 may have a concave shape or a flat shape. The shape of the front surface of treatment element 552 may be selected to conform to the soft palate tissue. The back surface of treatment element 552 comprises a shallow curved surface along most of its length. As best seen in FIGS. 4B and 4C, the back surface narrows distally along the length of the element 552, from approximately the distal end of the needle electrodes to the distal tip of the treatment element 552. This shape may maximize visualization of the area to be treated, while, at the same time, providing sufficient rigidity for treatment. Other shapes are also possible. For example, treatment element 552 may have a generally spherical or cylindrical shape. In some embodiments, treatment element 552 comprises an angular shape (e.g., triangular, conical), which may allow for close conformation to the tissue structures.

Treatment element 552 may include a monopolar or bipolar array of RF needles 554. In bipolar embodiments, RF energy is delivered between pairs of needles 554. In monopolar embodiments, RF energy is delivered between needles 554 and a remote grounding pad (not shown). In some embodiments, electrode needle pairs 554 are arranged horizontally across treatment element 552. In some embodiments, electrode needle pairs 554 are arranged vertically across treatment element 552, or along the direction of shaft 558 and handle 560. Other configurations are also possible. For example, needle pairs 554 may be arranged diagonally across treatment element 552. According to alternative embodiments, treatment element 552 may be placed either internally, with needle pairs 554 positioned transmucosally, or externally, with needle pairs 554 positioned transdermally. Distal tip 556 of treatment device 550 may also function as a mold or molding element. In various embodiments, RF energy may be selectively delivered between certain sets of needles to optimize the treatment effect.

Treatment element 552 of the treatment device 550 further comprises a pin-shaped thermocouple 555, extending up from a middle portion of the front surface of treatment element 552. Thermocouple 555 may include an insulating bushing. In some embodiments, different heat sensors (e.g., thermistors) may be used. In some embodiments, thermocouple 555 may be configured to measure a temperature of the surface or subsurface of tissue being treated and/or adjacent tissue. A pin shape having a sharp point may allow the structure to penetrate musocal tissue to obtain temperature readings from below the tissue surface. Thermocouple 555 can also be configured to measure a temperature of treatment element 552. The temperature measurements taken by thermocouple 555 can be routed as feedback signals to a control unit, and the control unit can use the temperature measurements to adjust the intensity of energy being delivered through electrodes 554. In some embodiments, thermocouple 555 or other sensing devices may be used to measure multiple tissue and device parameters. For example, multiple thermocouples 555 or thermistors may be used to measure a temperature at different locations along treatment element 552. In some embodiments, one of the sensors may be configured to penetrate deeper into the tissue to take a measurement of a more interior section of tissue. For example, treatment device 550 may have multiple sensors configured to measure a temperature at the mucosa, the cartilage, and/or treatment element 552. As described above, in some embodiments, the sensors described herein (such as thermocouple 555) are configured to take a measurement of a parameter. For example, tissue impedance can be measured through the electrodes or one or more separate sensors. These measurements can be used to adjust the intensity and/or duration of energy being delivered through the treatment element. This type of feedback may be useful from both an efficacy and a safety perspective.

In various embodiments, treatment element 552 may have any suitable size and shape. For example, in some embodiments, treatment element 552 may have a width of about 0.2 inch to about 1 inch and a length of about 0.4 inch to about 3 inches. Treatment element 552 can, in some embodiments, comprise a ceramic material (e.g., zirconium, alumina, silicon glass). Such ceramics may advantageously possess high dielectric strength and high temperature resistance. In some embodiments, treatment element 522 may include polyimides or polyamides, which may advantageously possess good dielectric strength and elasticity and be easy to manufacture. In some embodiments, treatment element 552 may include thermoplastic polymers. Thermoplastic polymers may advantageously provide good dielectric strength and high elasticity. In some embodiments, treatment element 552 may include thermoset polymers, which may advantageously provide good dielectric strength and good elasticity. In some embodiments, treatment element 552 may include glass or ceramic infused polymers. Such polymers may advantageously provide good strength, elasticity, and dielectric strength.

In some embodiments, electrodes 554 have a diameter of about 0.15 inch to about 0.25 inch and a length of about 0.2 inch to about 0.5 inch. In some embodiments, electrodes 554 may be made of steel (e.g., stainless, carbon, alloy). Steel may advantageously provide high strength while being low in cost and minimally reactive. In some embodiments, electrodes 554 or other energy delivery elements described herein comprise materials such as platinum, gold, or silver. Such materials may advantageously provide high conductivity while being minimally reactive. In some embodiments, electrodes 554 or other energy delivery elements described herein may include titanium, which may advantageously possess a high strength to weight ratio and be highly biocompatible. In some embodiments, electrodes 554 or other energy delivery elements described herein may include nickel titanium alloys. These alloys may advantageously provide high elasticity and be biocompatible. Other similar materials are also possible.

Energy applied to the tissue to be treated using any combination of the embodiments described in this application may be controlled by a variety of methods. In some embodiments, temperature or a combination of temperature and time may be used to control the amount of energy applied to the tissue. Tissue is particularly sensitive to temperature, so providing just enough energy to reach the target tissue may provide a specific tissue effect, while minimizing damage resulting from energy causing excessive temperature readings. For example, a maximum temperature may be used to control the energy. In some embodiments, time at a specified maximum temperature may be used to control the energy. In some embodiments, thermocouples, such as those described above, are provided to monitor the temperature at the electrode and provide feedback to a control unit. In some embodiments, tissue impedance may be used to control the energy. Impedance of tissue changes as it is affected by energy delivery. By determining the impedance reached when a tissue effect has been achieved, a maximum tissue impedance can be used to control energy applied.

In the embodiments described herein, energy may be produced and controlled via a generator that is either integrated into the electrode hand piece or is part of a separate device, such as a console, which delivers energy and in some cases control signals to the hand piece via a cable or other connection. In some embodiments, the generator is an RF energy source configured to communicate RF energy to the treatment element. For example, the generator may comprise a 460 KHz sinusoid wave generator. In some embodiments, the generator is configured to run between about 1 and 100 watts. In some embodiments, the generator is configured to run between about 5 watts and about 75 watts. In some embodiments, the generator is configured to run between about 10 watts and about 50 watts. In some embodiments, the RF energy source may be the same as or similar to the console described in U.S. patent application Ser. No. 16/668, 678 and U.S. Pat. Nos. D880,694 and D881,904, which were previously incorporated by reference.

In some embodiments, the energy delivery element comprises a monopolar electrode. Monopolar electrodes are used in conjunction with a grounding pad. The grounding pad may be a rectangular, flat, metal pad. Other shapes are also possible. The grounding pad may comprise wires configured to electrically connect the grounding pad to an energy source (e.g., an RF energy source). In alternative embodiments, any other suitable form of energy may be substituted for, or combined with, RF energy, such as but not limited to any energy in the electromagnetic spectrum, ultrasound, microwave, laser light, heat, steam, chemical energy, mechanical energy, or the removal of energy, such as cryotherapy devices.

In some embodiments, the treatment/energy delivery element, such as the electrodes described above, may be flat. Other shapes are also possible. For example, the energy delivery element can be curved or comprise a complex shape. For example, a curved shape may be used to place pressure on and thus deform the tissue to be treated. The energy delivery element may comprise needles or microneedles. The needles or microneedles may be partially insulated. Such needles or microneedles may be configured to deliver energy or heat to specific tissues, while avoiding tissues that should not receive energy delivery.

In some embodiments, the non-electrode portion of treatment element 552 may include an insulating material, such as a ceramic material (e.g., zirconium, alumina, silicon glass). In some embodiments, treatment elements 552 may include an insulating material interposed between multiple electrodes 554 or electrode sections. These insulating sections may provide an inert portion of the treatment element that does not deliver energy to the tissue. Such ceramics may advantageously possess high dielectric strength and high temperature resistance. In some embodiments, the insulators described herein comprise polyimides or polyamides, which may advantageously possess good dielectric strength and elasticity and be easy to manufacture. In some embodiments, the insulators described herein comprise thermoplastic polymers. Thermoplastic polymers may advantageously provide good dielectric strength and high elasticity. In some embodiments, the insulators described herein comprise thermoset polymers, which may advantageously provide good dielectric strength and good elasticity. In some embodiments, the insulators described herein comprise glass or ceramic infused polymers. Such polymers may advantageously provide good strength, elasticity, and dielectric strength. In some embodiments, one or more clear materials may be used to make the treatment element 552, to allow at least some visualization of tissue through treatment element 552.

In some embodiments, handle 560 and/or shaft 558 may be made of the same material(s) as those described with respect to the insulators. In some embodiments, handle 560 and/or shaft 558 may be made of a metal, such as stainless steel. In other embodiments, handle 560 and/or shaft 558 may be made of a polymer, such as polycarbonate. Other metals and polymers may alternatively be used.

In some embodiments, device 550 may be used in conjunction with a positioning element that can be used to aid in positioning of the device. The positioning element may be integrated into the device itself or can be separate. The positioning element may be used to help the user determine a desired placement of treatment element 552 to achieve a desired treatment result. In some embodiments, a positioning element is configured to be inserted and manipulated within the mouth until the patient reports a desired improvement in breathing. Device 550 may then be used to treat, while the positioning element is holding the mouth in the desired configuration. In some embodiments, molds may be used for this purpose. In some embodiments, a positioning element may be one or more measurement marks on shaft 558, indicating depth of insertion of shaft 558 into the mouth. For example, a physician may insert this element into the mouth to manipulate the tissue to find the depth of treatment at which the soft palate is contacted. The positioning element may alternatively or additionally include marks on shaft 558 indicating angle of insertion. The physician may use the marks to guide insertion of treatment element 552 to a desired location on the soft palate.

Any of the embodiments of devices described herein may be configured to heat specific tissue while maintaining lower temperatures in other adjacent tissue. The soft palate is an example of a tissue complex that includes adjacent tissues that may benefit from being maintained at different temperatures. Other examples include skin, which includes epidermis, dermis, and subcutaneous fat, and tonsils, which include mucosa, glandular tissue, and vessels. Treatment of other tissue complexes is also possible. For example, in some embodiments, the internal structures of the soft palate, below the mucosa, may be heated, while maintaining a lower temperature in the mucosal lining of the soft palate. Limiting unwanted heating of non-target tissues may allow trauma and pain to be reduced, may reduce scarring, may preserve tissue function, and may also decrease healing time. Combinations of heat transfer and/or heat isolation may allow directed treatment of specific tissue, such as cartilage, while excluding another tissue, such as mucosa, without surgical dissection.

Figure 5:
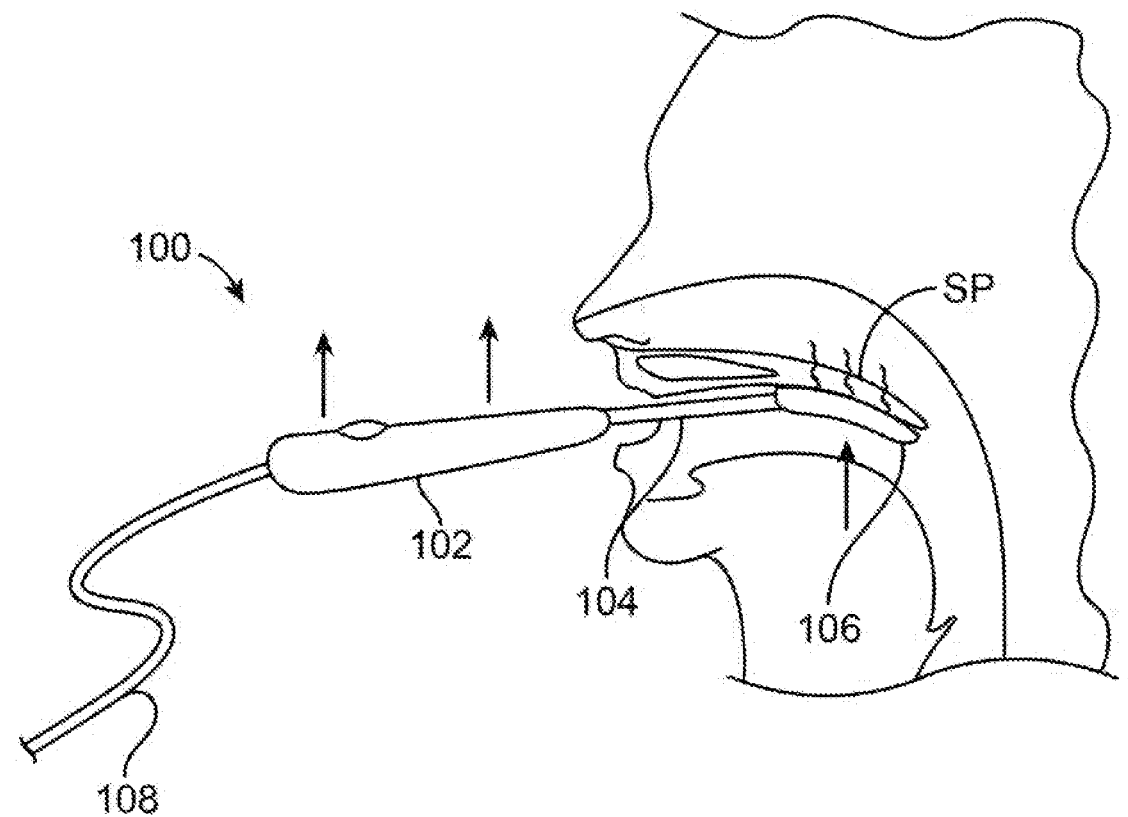
FIG. 5 is a side/cross-sectional view of a patient's head and a side view of a device being applied to the soft palate to treat OSA and/or snoring, according to one embodiment.

Referring now to FIG. 5, one embodiment of a method for treating soft palate SP tissue is illustrated. In the embodiment shown, a soft palate tissue treatment device 100 includes a handle 102, a shaft 104, a treatment element 106 and a cord 108, which is attached to a console (not illustrated). In use, treatment element 106 is advanced into the patient's mouth, and an upper surface (or "treatment surface") of treatment element 106 is contacted with the mucosal surface (or "mucosa") of the soft palate. In some embodiments, the physician or physician's assistant may apply upwardly directed force (solid-tipped arrows) to treatment element 106, by pulling up on handle 102, thus deforming a portion of the soft palate SP. While holding the soft palate in the deformed configuration, energy (wavy lines) may be delivered to the tissue via multiple RF electrodes or other energy delivery devices on the upwardly facing treatment surface of treatment element 106. Force and energy may be applied in any suitable amount and for any suitable length of time, according to treatment goals, patient anatomy, treatment protocols and/or the like. In some embodiments, device 100 may be removed from the patient's mouth after one area of the soft palate is treated. Alternatively, after a first treatment, treatment element 106 may be moved to a second area of treatment, and another treatment may be delivered. This may be repeated as many times as desired, to cover a desired treatment area.

As mentioned above, the treatment may be used to change the shape, strength, stiffness and/or any other property of any soft palate tissue, such as but not limited to muscle, mucosa, nerve, blood vessel, cartilage, fat and collagen. In embodiments where the shape of the soft palate is changed during the treatment, at least some of this change in shape will be retained after the treatment. In addition to treating the soft palate, some treatment method embodiments may also include treating other nearby tissues of the mouth, throat, tongue, etc. Also, the upper, treatment surface portion of treatment element 106 may include any suitable energy delivery device and may have any suitable shape for addressing the soft palate. For example, treatment element 106 may deliver energy in the form of bipolar RF, monopolar RF, ultrasound, cryotherapy (energy removal), heat, chemical, microwave, laser or any other suitable type of energy, and it may include any number of energy delivery members. The shape of the treatment surface may be convex, concave or flat and may have any shape, such as ovoid, rectangular, triangular, asymmetric, etc.

Figure 6:
FIG. 6 is a perspective view of a device for applying energy to the soft palate for treating OSA and/or snoring, according to an alternative embodiment.
Figure 6:
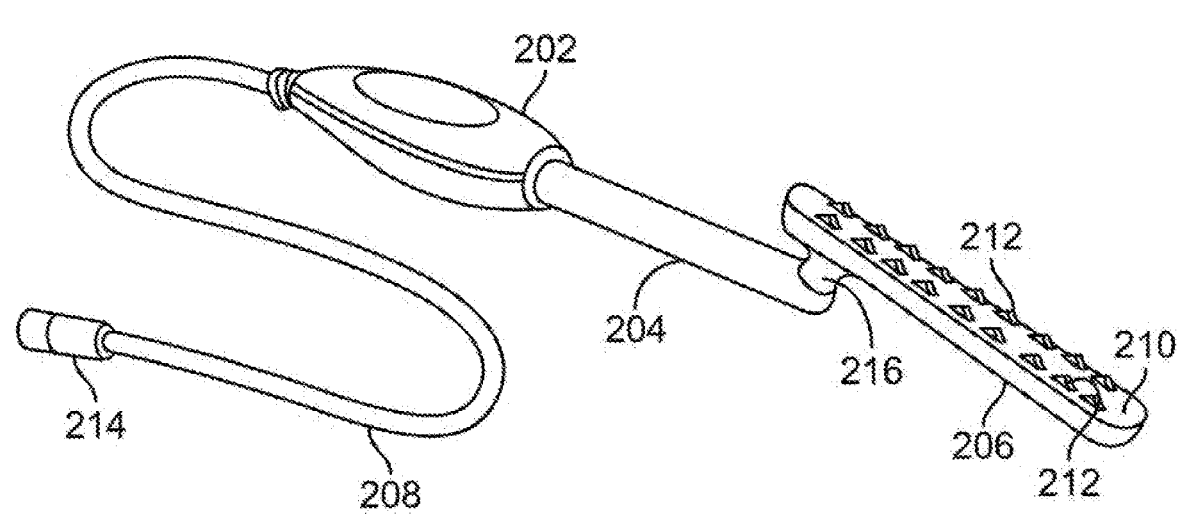

Referring to FIG. 6, an alternative embodiment of a soft palate treatment device 200 may include a handle 202, a shaft 204, an elongate treatment element 206, a power/energy delivery cable 208, and an adapter 214 for connecting with a console or other power/energy source (not shown). In this embodiment, shaft 204 may include an angled neck 216, so that treatment element 206 is angled slightly, relative to the longitudinal axis of shaft 204. Alternatively, treatment element 206 may be parallel with shaft 204, coaxial with shaft 204, or have any other position relative to shaft 204. Treatment element 206 may include an upper treatment surface 210 and multiple RF electrodes 212 arrayed along surface 210 in two parallel rows. In this embodiment, surface 210 is relatively long and straight, with curved ends, and electrodes 212 are shaped as triangular protrusions from surface 210, are aligned in two rows, and are bipolar RF electrodes 212. As mentioned above, in alternative embodiments, treatment element 206, treatment surface 210 and electrodes 212 may have any other suitable shapes, numbers and configurations, and in alternative embodiments, alternative energy delivery members may be used. Handle 202 may either be rigidly or flexibly attached to shaft 204, thus potentially allowing for relative movement between these two components in some embodiments. In some embodiments, shaft 204 is malleable, to allow the physician to bend the shaft 204 to a desired angle. In some embodiments, electrodes 212 may be moveable, relative to treatment element 206, for example in and out of surface 210 or along surface 210.

As illustrated in this embodiment, treatment surface 210 is relatively long and flat. This shape may be ideal for treating soft palate (and possibly other tissue in the mouth or throat) to treat OSA and/or snoring. On the other hand, treatment surface 210 may have a convex shape or other shape in alternative embodiments, to help deform soft palate tissue into a desired configuration. Whatever the shape of surface 210, electrodes 212 are used to apply RF energy to the target tissue, to cause heating and eventual shrinking, stiffening, reshaping and/or other property changes of the soft palate. In many cases, the target tissue may be a submucosal tissue (or tissues)—e.g., any tissue(s) below mucosal lining of the soft palate. The resulting treatment effect may include volume reduction, tissue stiffening (higher modulus) and/or stiffening by way of more optimal structure (e.g., arched tissue with a higher second moment of inertia, better bending stiffness, etc.). Radiofrequency energy may be controlled via temperature feedback, such as a thermocouple and RF power controller, and/or may be controlled to impart a specific total energy. Device 200 may also be used with minimal built-in control and applied by the physician under visualization until the intended effect on the target tissue has been achieved. In alternative embodiments, alternate energy sources may include cryogenic surface cooling, combinations of cooling and heating technologies, cauterizing agents, ultrasound or the like.

Figure 7:
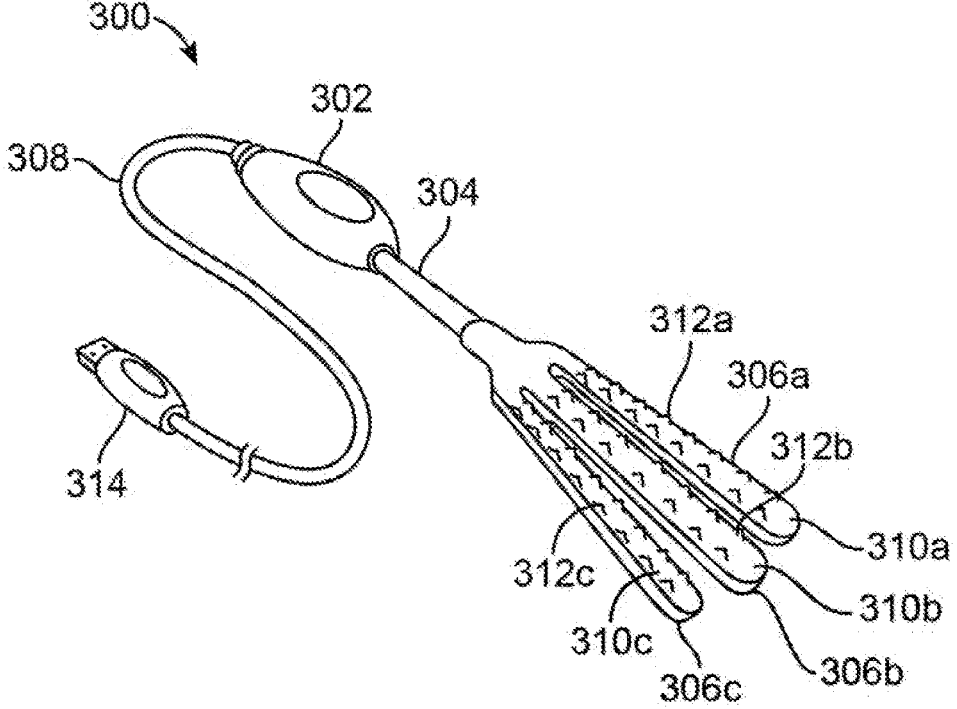
FIG. 7 is a perspective view of a device for applying energy to the soft palate for treating OSA and/or snoring, according to another alternative embodiment.

With reference now to FIG. 7, another alternative embodiment of a soft palate treatment device 300 may include a handle 302, a shaft 304, three treatment elements 306a-c, a power/energy delivery cable 308, and an adapter 314 for connecting with a power/energy source. In this embodiment, shaft 304 is on the same vertical plane as treatment elements 306a-c. Treatment elements 306a-c include upper treatment surfaces 310a-c and multiple RF electrodes 312a-c arrayed along surfaces 310a-c in two parallel rows. This configuration and number of treatment elements 306a-c may be ideal for addressing a larger area of the soft palate in one treatment. Alternative embodiments may include any suitable number, shape, size and configuration of treatment elements and electrodes. For example, either the treatment elements or the electrodes may be formed in cross-cross overlapping configurations, in one or T-shapes, or in any other geometric shape that might facilitate accessing and treating soft palate tissue. In one embodiment, for example, the treatment element (or elements) may be shaped to make a treated-tissue pattern in the soft palate that reduces vibrations. This reduced vibratory effect in the soft palate may help reduce snoring and/or reduce OSA. Again, any suitable pattern, shape, combination of shapes, sizes or the like may be used in a given embodiment.

As mentioned above, any of the embodiments described in the Incorporated Patents may be used (or adapted for use) to treat the soft palate for addressing OSA and/or snoring. Similarly, any features described in the Incorporated Patents may be incorporated into the device designs described herein.

Figure 8:
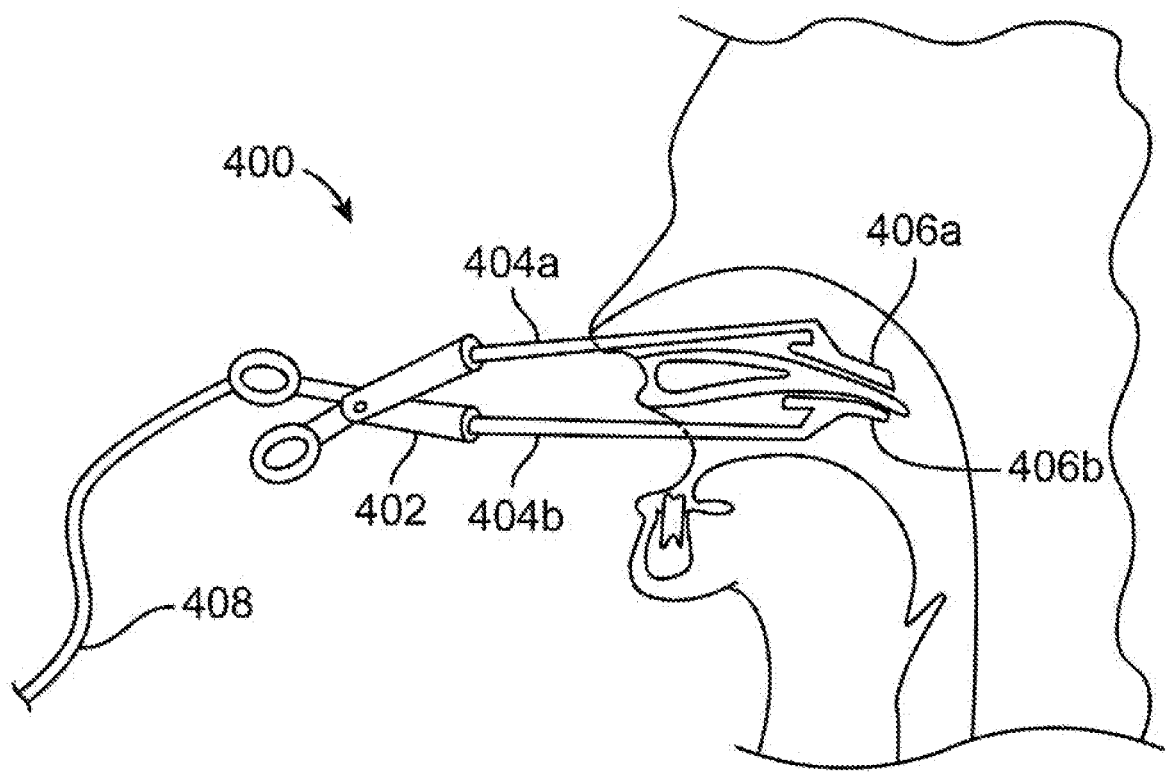
FIG. 8 is a side/cross-sectional view of a patient's head and a side view of a device being applied to the soft palate to treat OSA and/or snoring, according to another alternative embodiment.

Referring now to FIG. 8, in another alternative embodiment, a soft palate treatment device 400 may include a handle 402 that acts like a clamp or scissors handle, two shafts 404a-b extending from handle 402, two tissue treatment elements 406a-b (one at the end of each shaft 404a-b), and a power/energy cable 408. This embodiment of device 400 is similar to the clamp-type devices described in the Incorporated Patents, although it may be sized and/or shaped differently, to address the soft palate. In this embodiment, one shaft 404a is configured to extend through a nostril, so that its corresponding treatment element 406a contacts an upper surface of the soft palate, and the other shaft 404b is configured to extend through the mouth, so that its corresponding treatment element 406b contacts a lower surface of the soft palate. Treatment elements 406a-b can then be used to clamp the soft palate tissue between them and, in some embodiments, to alter the shape of the tissue. Energy may then be delivered from both treatment elements 406a-b or alternatively from one treatment element 406a or 406b, across the tissue to the other element 406b or 406a. In some embodiments, shafts 404a-b and treatment elements 406a-b may be exactly or almost exactly the same, in terms of diameter, length and shape. Alternatively, one shaft 404a-b and/or one treatment element 406a-b may be smaller, for fitting through a nostril, and the other may be larger, for fitting through the mouth.

Again, any of the features described in the Incorporated Patents may be incorporated into device 400, according to various embodiments. Although no incisions have been described above, in some embodiments, the treatment method may involve forming a small incision in the mucosa of the soft palate and advancing the treatment element through the incision to contact and treat tissue underlying the mucosa. Such embodiments are described more fully in some of the Incorporated Patents.

Figure 9:
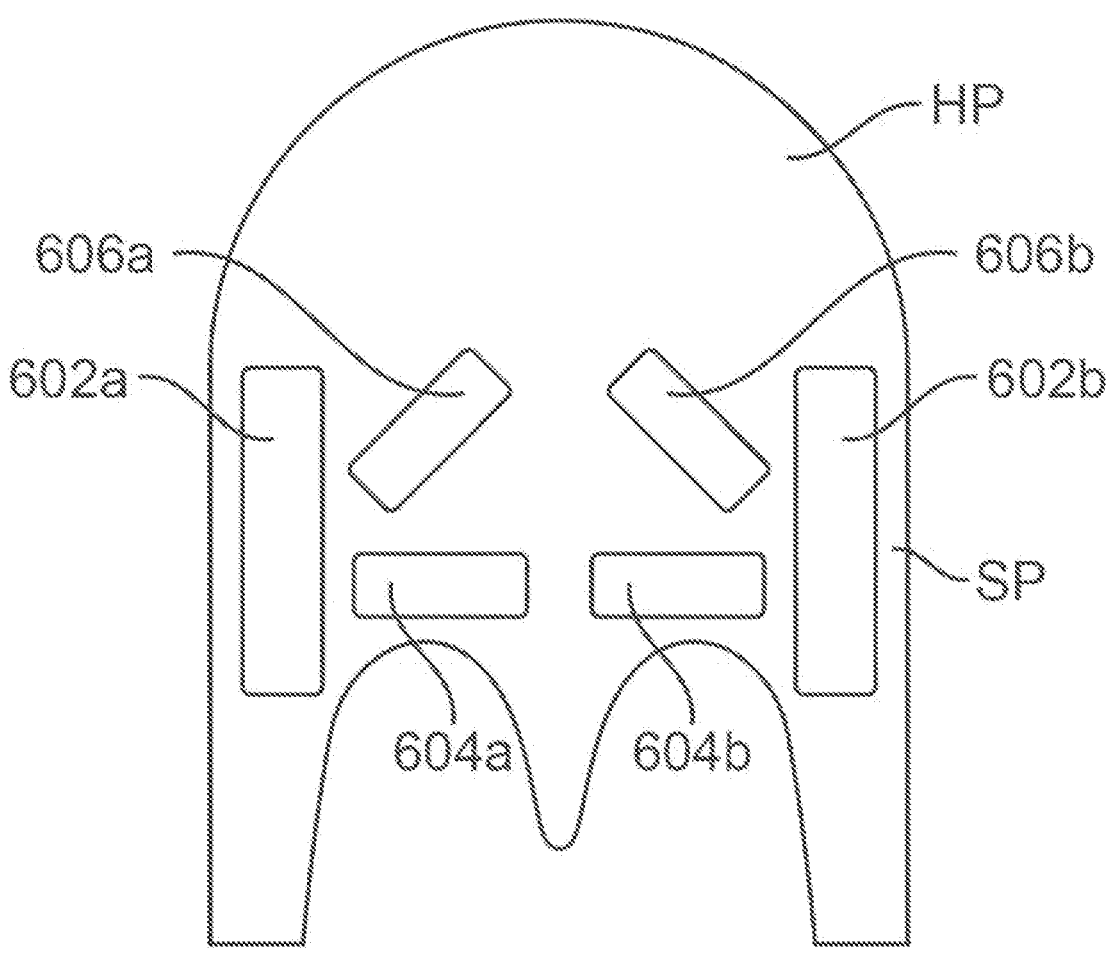
FIG. 9 is diagrammatic view looking down onto a soft palate, illustrating various locations and orientations for possible treatment of the soft palate with an energy delivery device, according to various embodiments.

FIG. 9 is diagrammatic view of the bottom facing (i.e., mouth facing) surface of a soft palate SP and hard palate HP, illustrating various locations and orientations for possible soft palate SP treatment, according to various embodiments. These are only a few examples of nearly infinite numbers of treatment locations, orientations and combinations. In any given energy delivery (or removal) treatment, using any of the embodiments described above or alternatives, therapy may be directed at any portion or portions of the soft palate SP, in any pattern, shape, size or configuration. For example, in one embodiment, treatment may be applied at or near lateral edges 602a, 602b of the soft palate SP, in a configuration of strips of tissue that are parallel to one another and in an anterior-to-posterior orientation. In another embodiment, laterally directed strips 604a, 604b near the back of the soft palate SP may be treated. In another embodiment, diagonally oriented strips 606a, 606b near the front of the soft palate SP may be treated. Alternatively, any or all of the above treatment areas may be combined in one treatment. In other embodiments, any other treatment areas, shapes, sizes and/or patterns may be used. For example, a circular treatment element may treat tissue in a circular shape. Curved treatment elements may be used in some embodiments. Treatment patterns such as X-shaped or T-shaped patterns may be used. Treatments may be overlapped in any suitable configuration. In some embodiments, treatments may be administered to shape the soft palate into a specific desired shape. For example, one part of the soft palate may be straightened, while another part may be curved. A multiple-headed treatment element may treat more than one area of tissue at a time. Again, any variation of sizes, shapes and patterns of treatment may be used, according to various alternative embodiments.

In one embodiment, during a soft palate treatment, the soft palate is tested, to see if the treatment is having a desired effect. For example, nerve stimulation may be used in some embodiments to stimulate one or more muscles of the soft palate during treatment, to observe movement of the palate. In other embodiments, air may be blown past the palate to test for vibrations or sounds emanating from the soft palate, as might happen in snoring. After testing the soft palate in one or more such ways, another area of the palate may be treated with the device (or the same area may be treated again). The palate may then be tested again. For example, another muscle of the palate may be stimulated. This process may be repeated as many times as desired, in order to treat and test the palate during the same procedure and potentially alter treatment to achieve a more desirable outcome.

Figure 10A:
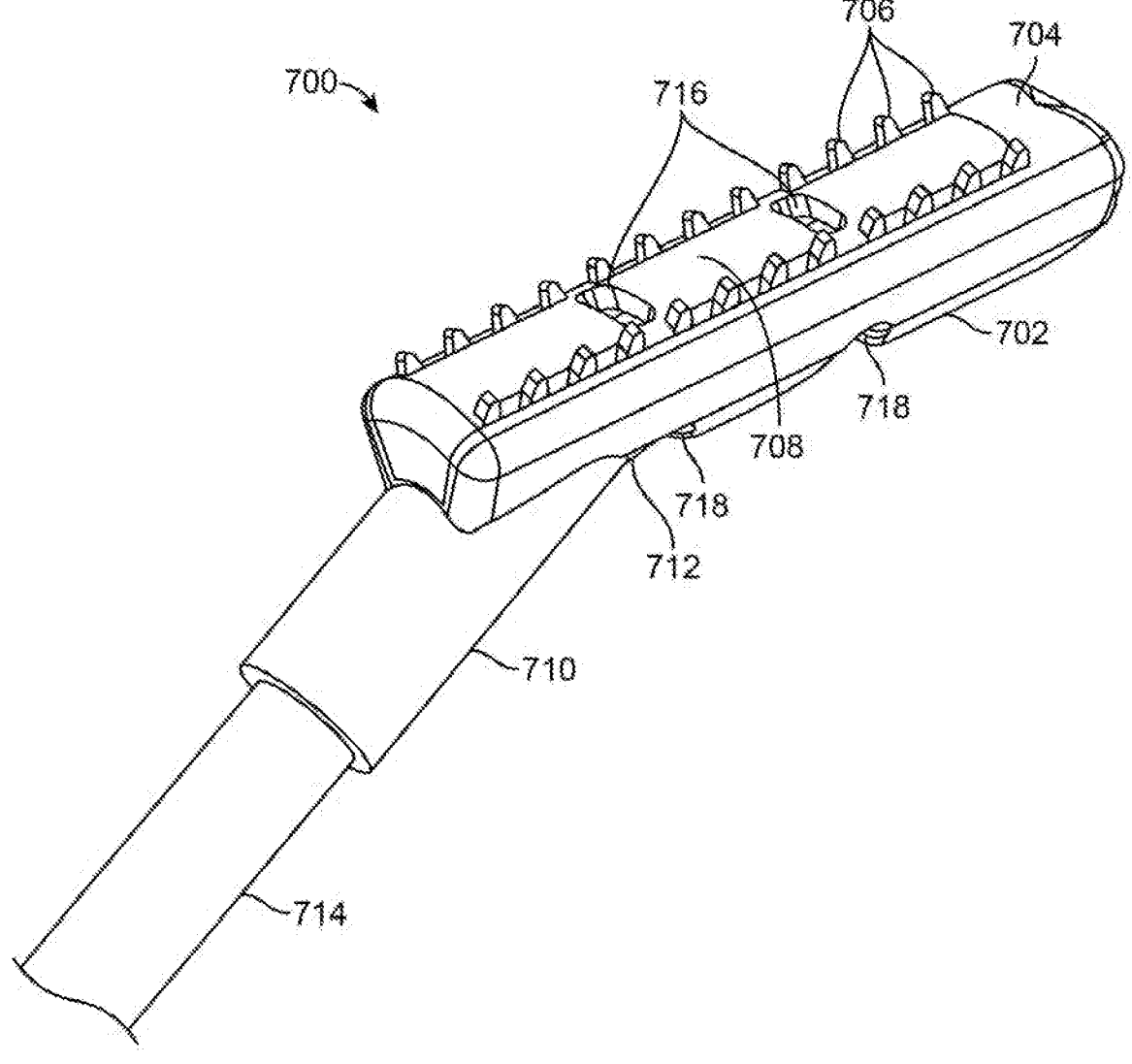
FIGS. 10A-10C are perspective, perspective and side views, respectively, of a distal portion of an energy delivery soft palate treatment device, according to one embodiment
Figure 10B:
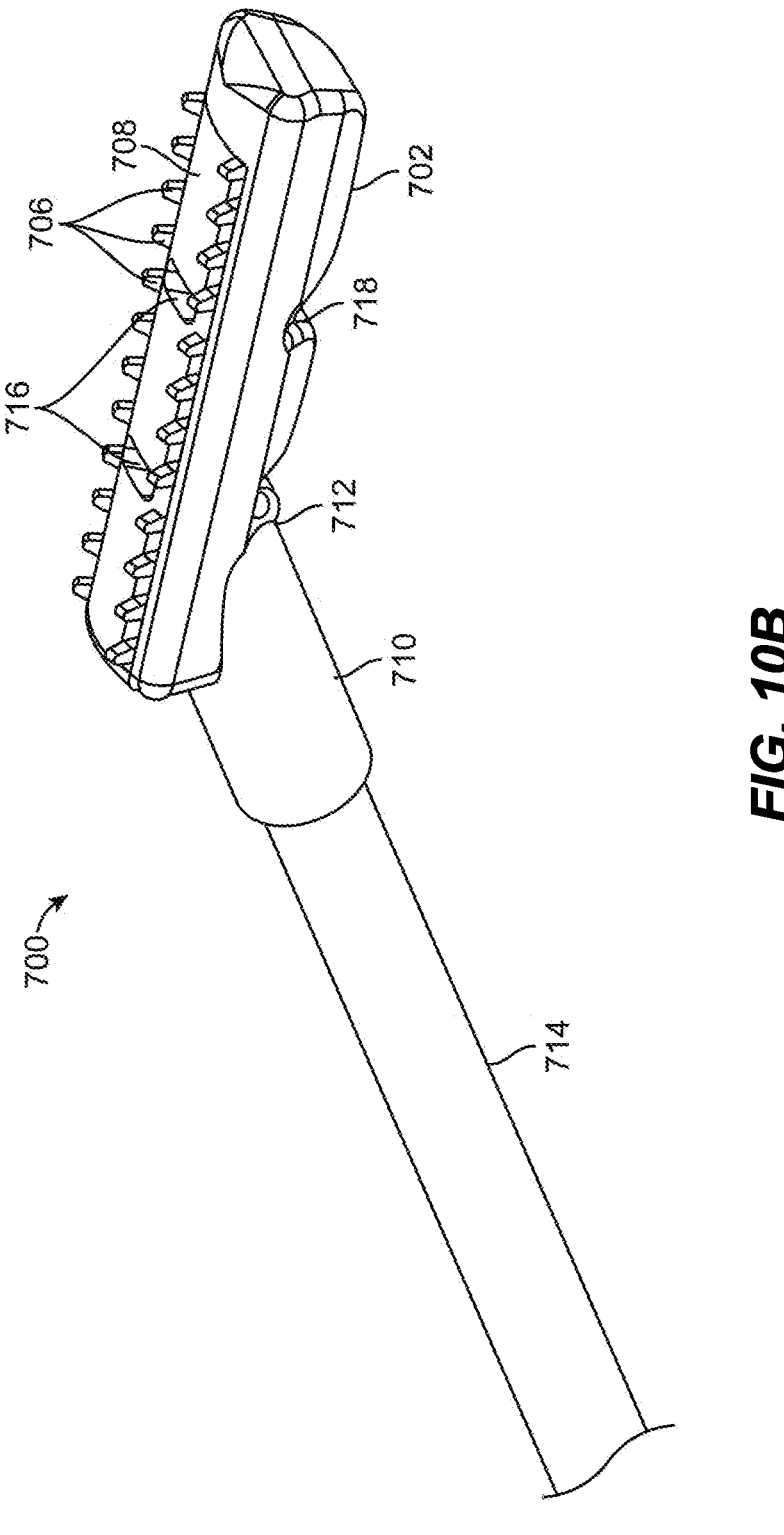
Figure 10C:
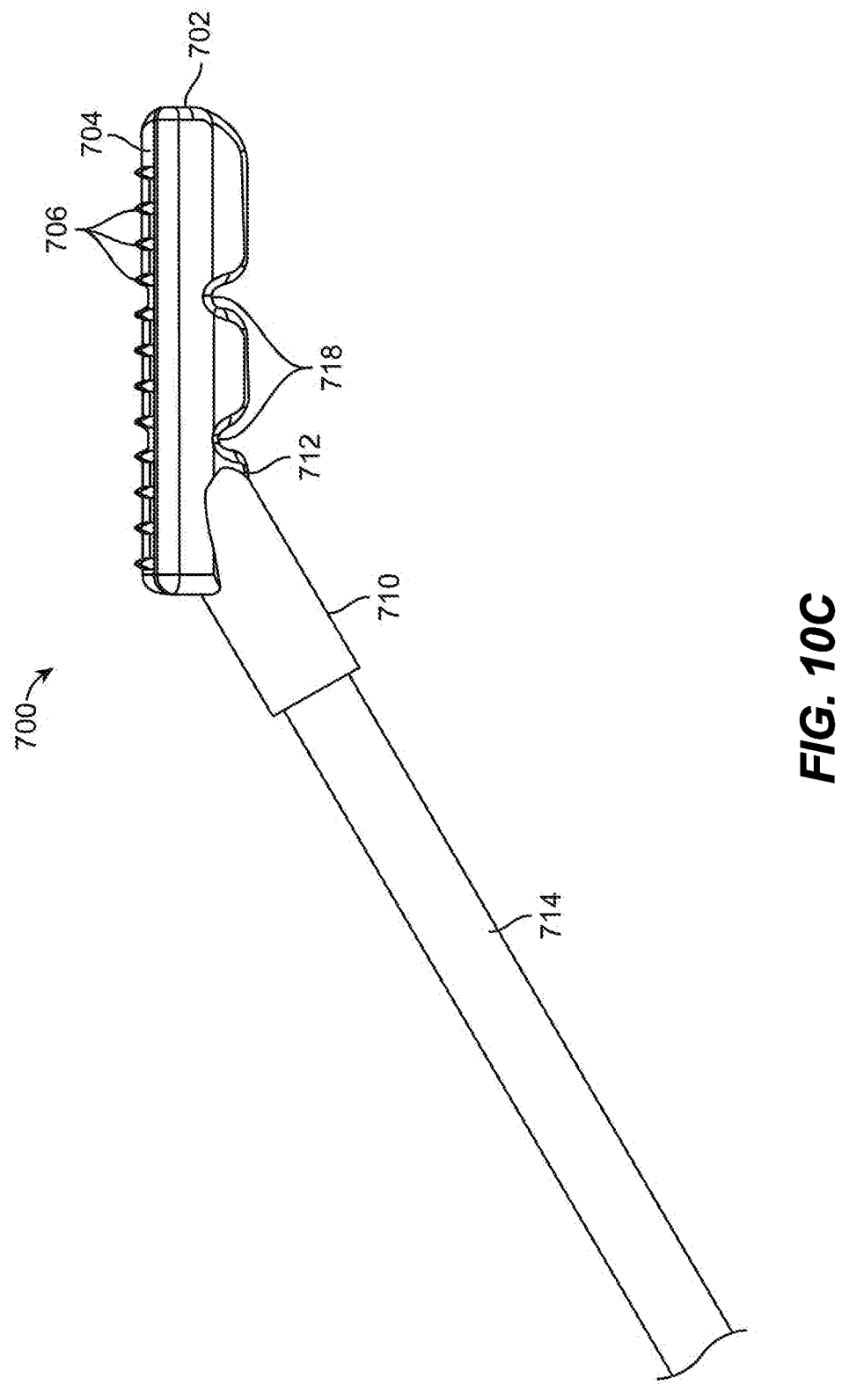

FIGS. 10A-10C are perspective views (FIGS. 10A and 10B) and a side view (FIG. 10C) of a distal portion of another embodiment of an energy delivery soft palate treatment device 700. These figures show a distal portion of a shaft 714 of device 700, attached to a distal tip 702. Distal tip 702 includes a treatment surface 704, which includes two rows of protruding, bipolar electrodes 706 and a nonconductive material 708 positioned between electrodes 706. Two optional apertures 716 are formed in nonconductive material 708, which may help distal tip 702 flex upward. The opposite (or "top") surface of distal tip 702 may include two indents 718 (or fewer or more indents in alternative embodiments), which may allow distal tip 702 to flex in the upper/top direction. Distal tip 702 may also include a bend 712 between the head (or distal portion) of distal tip 702 and a neck 710 of distal tip 702. In some embodiments, neck 710 may fit over a distal end of shaft 714 for manufacturing purposes.

As described previously, distal tip 702 may have any suitable length, width, height and shape for treating a soft palate. In some embodiments, for example and as shown, treatment surface 704 may have a slightly convex shape, with the curve of the convex surface aligned perpendicular to the longitudinal axis of distal tip 702. In alternative embodiments, treatment surface 704 may be flat, concave or otherwise shaped. Any suitable number, size and shape of electrodes 706 may also be used. Electrodes 706 may be protruding but not penetrating, as shown, or alternatively may be penetrating needle electrodes or flat electrodes.

In various embodiments, distal tip 702 (or one or more portions thereof) may be rigid or flexible. A flexible or partially flexible distal tip 702, for example, may be able to conform to the shape of the soft palate. In some embodiments, the ability of distal tip 702 to flex may be enhanced by one or more "flex points," such as bend 712, apertures 716 and indents 718. Distal tip 702 may be made of any suitable materials or combinations of rigid and/or flexible materials, such as but not limited to Nitinol, stainless steel, other metals, polymers such as urethane, silicone, low-density polyethylene (LDPE), or the like. In some embodiments, distal tip 702 may be divided into multiple segments, for example to enhance flexibility. Apertures 716, for example, may divide distal tip 702 into three segments, each segment having four pairs of electrodes 706. In some embodiments, each segment of electrodes 706 is separately controllable. As mentioned previously, indents 718 on the bottom surface may also lend flexibility to distal tip 702. Some embodiments (not shown) may also include a thermocouple or other temperature sensing device, for example on nonconductive surface 708 between electrodes 706, to sense temperature of the soft palate tissue being treated. The sensed temperature may be transmitted back to a control unit and used to regulate delivery of energy, based on the temperature.

In various embodiments, apertures 716 in treatment surface 704 may range in number from one to dozens. (Apertures 716 are also an optional feature, so some embodiments do not include any.) In addition to allowing distal tip 702 to flex upward, apertures 716 may serve one or more additional functions. For example, in some embodiments apertures 716 may connect with a fluid delivery lumen running through shaft 714 and distal tip 702, to provide irrigation fluid at the procedure site. In addition to, or instead of, providing fluid at the procedure site, apertures 716 may provide suction or vacuum force, for example to suction fluid out of the area or to allow treatment surface 704 to adhere more strongly to the tissue surface being treated. In some embodiments, apertures 716 may alternatively or additionally serve as locations for one or more temperature sensors.

To make the energy delivery device 700 easier to use, the bend 712 in the distal tip 702 may have any suitable angle. For example, some embodiments may have almost no bend 712—i.e., a straight embodiment. Other embodiments may have a bend angle of 135 degrees or more. Or any other angle may be used, as feasible, in various embodiments. Similarly, the indents 718 may have any suitable size, shape and number, to allow the distal tip 702 to flex downward in a desired configuration to conform to the soft palate.

Figures 11A, 11B, 11C, 12:
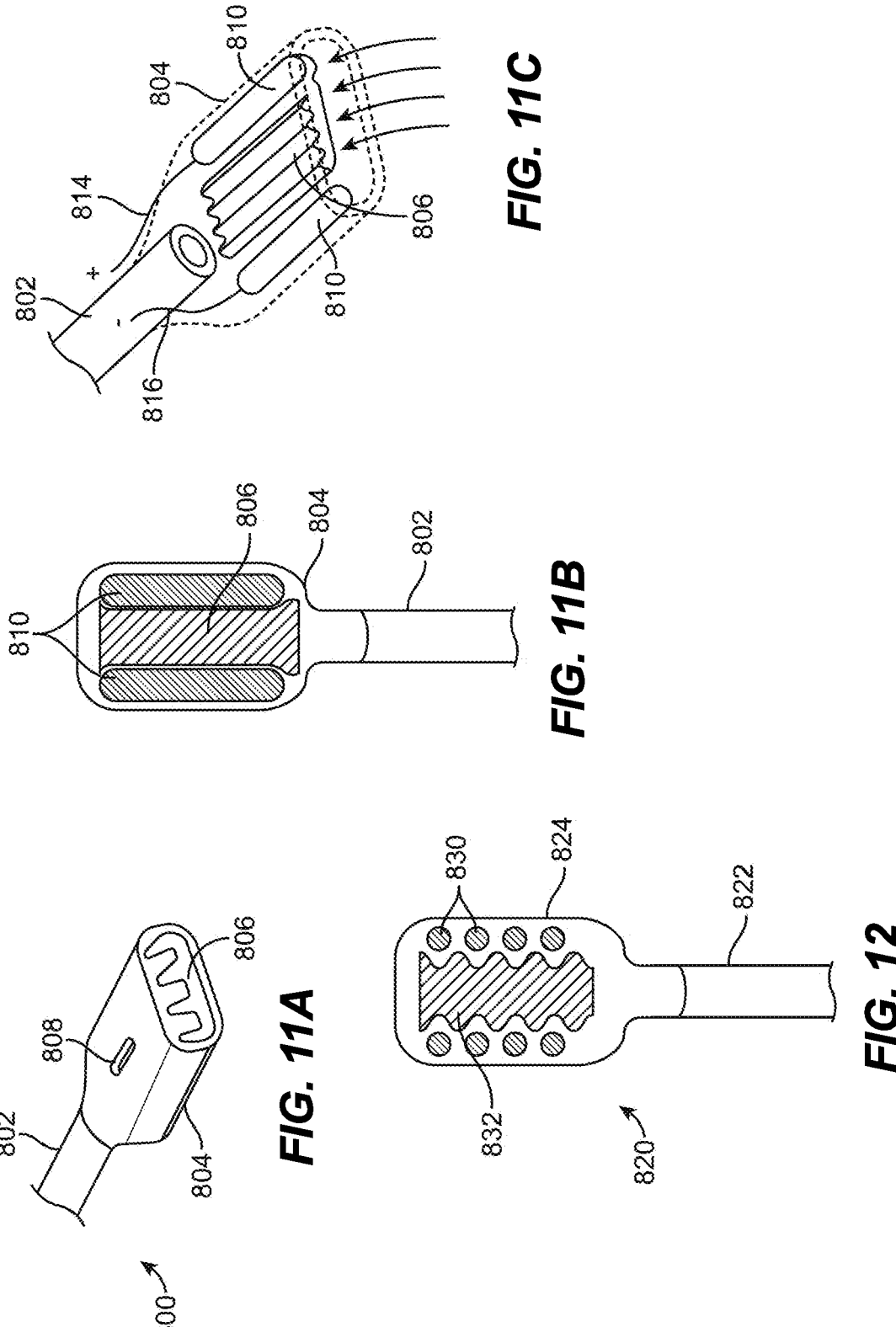
FIGS. 11A-11C are perspective, bottom and partial cross-sectional views, respectively, of a distal portion of a soft palate tissue treatment device with a cooling member, according to one embodiment.
FIG. 12 is a bottom view of a distal portion of a soft palate tissue treatment device with a cooling member, according to an alternative embodiment.

Referring now to FIGS. 11A-11C, another embodiment of a soft palate tissue treatment stylus 800 is illustrated. Using this embodiment or any of the embodiments described above, energy may be delivered to one or more target tissues at a predefined (or selected) tissue depth below the mucosal surface on which the treatment delivery portion of the device is placed. For example, if bipolar RF energy is the type of energy used for the treatment, the RF energy may be transmitted from one electrode or set of electrodes at or near one lateral side or edge of the treatment surface to a corresponding electrode or set of electrodes at or near an opposite lateral side or edge of the treatment surface. In traveling from one side to the other, the RF energy may pass through the mucosa and treat submucosal tissue at the selected tissue depth, in an arch-shaped or U-shaped energy delivery path. The target tissue may reside at any suitable depth, such as but not limited to a range of less than 1 mm to about 1 cm below the mucosal surface. By delivering energy to tissue below the mucosa, the treatment methods described herein may spare the mucosa from tissue trauma or damage ("mucosa sparing treatment"), which will likely improve patient satisfaction, reduce post-procedure pain and discomfort, and reduce recovery time. As mentioned above, any submucosal tissue (or combination of tissues) may be targeted in a given treatment, such as but not limited to muscle, cartilage, tendon, ligament, connective tissue, nerve, blood vessel and/or the like. To achieve this submucosal tissue treatment while sparing the mucosa, relatively low frequency, low power RF energy may be used. For example, this may involve delivering RF energy at a frequency of about 400 KHz to about 500 KHz and in one embodiment 460 KHz, and a power about 1 watts to about 100 watts, and in one embodiment about 10 watts to about 50 watts. Submucosal energy delivery for target tissue treatment is further described in the Incorporated References.

In some embodiments, such as stylus 800 of FIGS. 11A-11C, in addition to providing mucosa sparing treatment by directing energy delivery to target tissue(s) below the mucosa, stylus 800 also includes a mechanism for cooling the mucosal surface. FIG. 11A is a perspective view of a distal portion of stylus 800, showing a shaft 802 and a treatment portion 804 (or "distal tip"), the latter including a cooling member 806 and an air vent 808. FIG. 11B is a bottom view of the same portion of stylus 800, showing a tissue contact surface of the cooling member 806 and two longitudinal electrodes 810 disposed on opposite sides of cooling member 806. FIG. 11C is a perspective view with the outer housing of distal tip 804 removed to show cooling member 806 and electrodes 810 in more detail. One electrode 810 is coupled via wiring 814 to an RF source to act as the positive electrode, and the other electrode 810 is coupled via separate wiring 816 to act as the negative electrode. Cooling member 806 delivers suction at the extreme distal end of distal tip 804, thus sucking air into the through cooling member 806 and into shaft 802 (arrows). In addition to passing into shaft 802, some air may pass through air vent 808 on the top of distal tip 804. The passage of air through cooling member 806 causes convection cooling inside cooling member 806, which in turn applies conduction cooling to the mucosa that is in contact with cooling member 806. In various embodiments, the extreme distal end of distal tip 804 may have one or more openings leading into the cooling member, may include a filter of the opening(s), and/or the like. The tissue contact surface of cooling member 806 may be made of metal, plastic, polymer or any suitable material so as to convey the cooling to the mucosa without interfering with the RF energy delivery from electrodes 810.

As with any of the embodiments described herein, stylus may also include one or more temperature sensors (not pictured), which will typically be located on the tissue contact surface of treatment portion 804. In some embodiments, for example the temperature sensor may be a thermocouple located between two electrodes 810 or between two rows of electrodes in an alternative embodiment. Other embodiments may include multiple temperature sensors. Alternative embodiments may also include other types of temperature sensors. Whatever temperature sensor(s) are included, they may be used to automatically control delivery of energy, delivery of cooling, or both. For example if a predefined peak temperature is reached in mucosal tissue in contact with a thermocouple on stylus 800, a controller coupled with stylus 800 may receive the sensed temperature and automatically reduce the amount of RF energy being delivered to electrodes 810 and/or may increase passage of air through cooling member 806. The controller may also alert the user that the peak temperature has been reached. This type of temperature sensing capability may be included with any embodiment described herein, and thus this description will not be repeated for each embodiment.

Referring now to FIG. 12, an alternative embodiment of a soft palate tissue treatment stylus 820 is illustrated. Here, a distal portion of the stylus 820 is shown in bottom view. The stylus 820 includes a shaft 822, a distal tip 824 (or "tissue treatment portion"), two rows of bipolar RF electrodes 830, and a cooling member 832 between the electrodes 830. This embodiment is similar to the previous embodiment, other than the configuration of electrodes 830. In other embodiments, different types of cooling members may be used, such as but not limited to water circulating cooling members, cryogenic cooling members and the like. In various embodiments, the shaft 802 may include one or more working lumens to deliver suction (as in FIGS. 11A-12), cooling fluid, cryogenic fluid, or any other cooling agent to a cooling member. Any of the styluses described herein may include one or more cooling members, such as but not limited to those described in relation to FIGS. 11A-12.

Referring now to FIGS. 13A and 13B, another embodiment of a soft palate tissue treatment device 900 and method are illustrated. In this embodiment, the device 900 includes a handle 902, a shaft 904, a tissue treatment portion 906 and cable 908 for connecting to a console (not shown). In this embodiment, tissue treatment portion 906 is hook shaped or U-shaped, so that it fits around the end of the soft palate SP to contact tissue on the superior surface and the inferior surface of the soft palate SP at the same time. Radiofrequency energy may be delivered from one or more electrodes on the distal portion to one or more corresponding electrodes, so that the energy travels through the soft palate SP from top to bottom, as shown in FIG. 13B, or from bottom to top. Energy may be delivered in any pattern, for example to create and X-shaped treatment pattern in one embodiment (FIG. 13B). Shaft 904 may be straight and rigid, pre-shaped with a bend and rigid, or malleable to allow the user to form it into a desired shape. In an alternative embodiment, the treatment device may be sized and shaped to be advanced through a nostril and the nasal cavity, so that the hook-shaped tissue treatment portion 906 hooks around the soft palate SP from top to bottom.

Figure 14A:
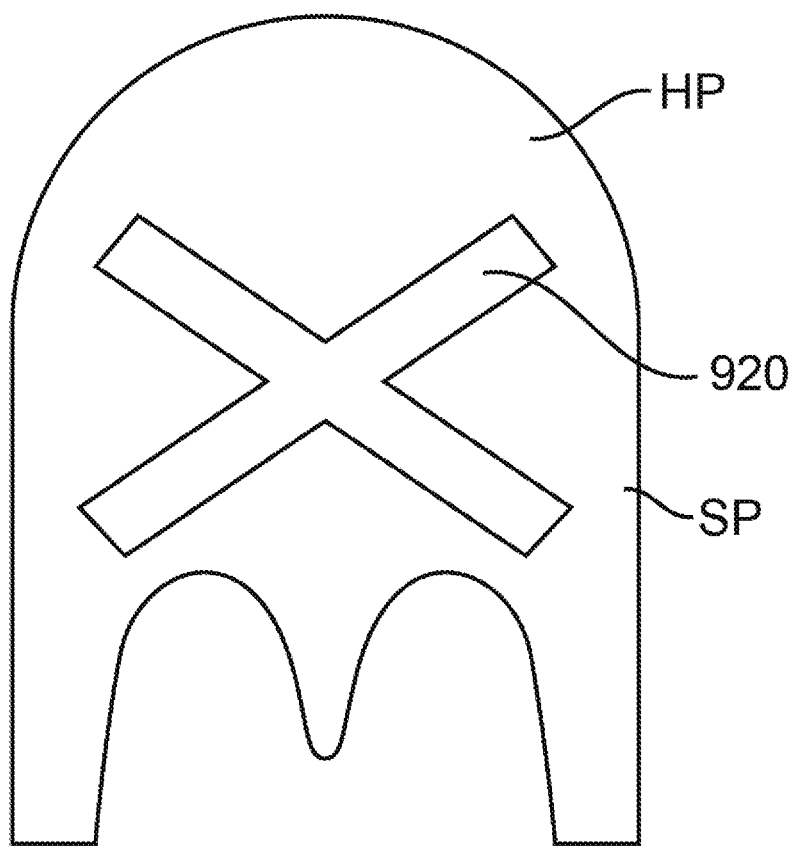
FIG. 14A is a diagrammatic view of a soft palate, illustrating a tissue treatment pattern, according to one embodiment.

FIG. 14A is a diagrammatic illustration of the bottom surface (mouth facing) of the soft palate SP and the hard palate HP, showing one example of an X-shaped treatment pattern 920 that might be achieved with tissue treatment device 900 of FIGS. 13A and 13B. This pattern may also be achieved using at least some, if not all, of the other embodiments described herein.

Figure 14B:
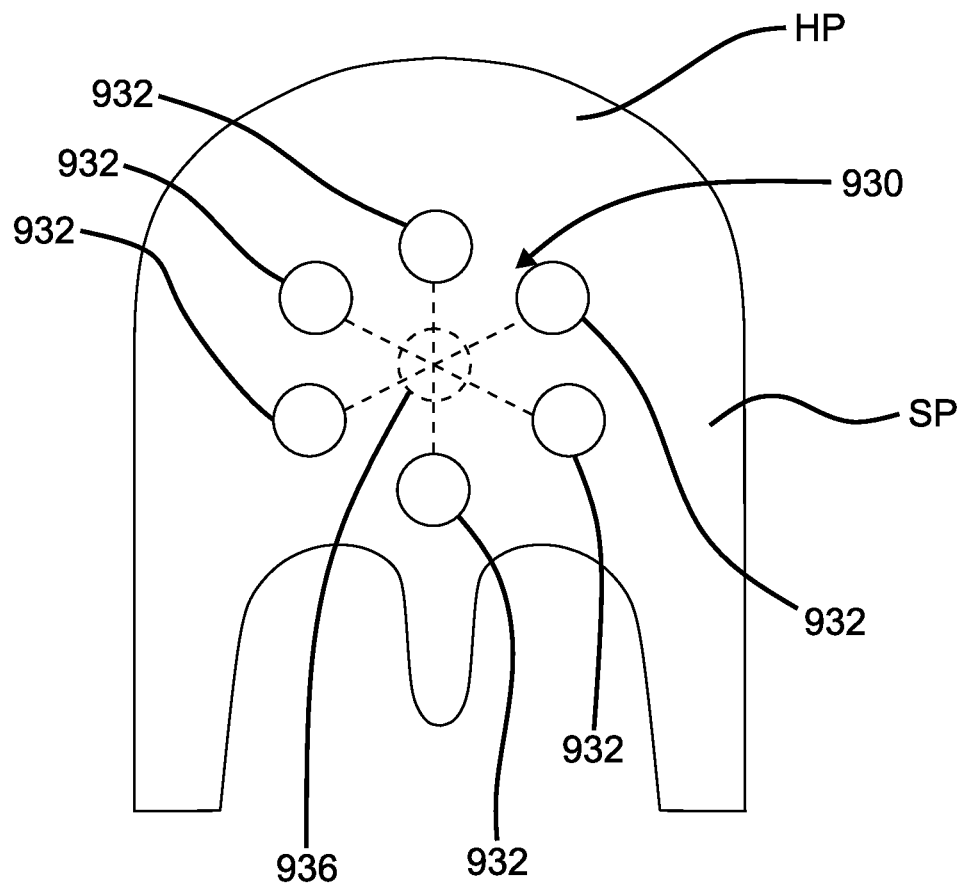
FIG. 14B is a diagrammatic view of a soft palate, illustrating a tissue treatment pattern, according to an alternative embodiment.

FIG. 14B is another diagrammatic illustration of the mouth facing surface of the soft palate, illustrating another treatment pattern 930 that may be achieved according to some embodiments. As illustrated in FIGS. 8 and 13A-13B, in some embodiments, the soft palate treatment device and method involves contacting a lower surface and an upper surface of the soft palate SP and delivering energy through the palate in one direction or both directions. In various embodiments, the two soft palate surfaces may be contacted by a device that wraps around the end of the palate (as in FIGS. 13A-13B) or that has two separate pieces or devices (as in FIG. 8). In some embodiments, for example, two pieces of a treatment device may include magnets to attract the two pieces together to hold them in place on opposite sides of the palate. In the embodiment of FIG. 14B, the treatment pattern 930 includes six energy delivery spots 932 formed using a device having six electrode pairs, where one electrode of each pair is positioned on the upper surface of the soft palate and the other electrode of each pair is positioned on the lower surface of the soft palate. Energy is delivered through the soft palate with the electrode pairs to treat tissue below the mucosa and in spots 932. The delivered energy also converges toward a middle treatment area 936. Thus, the soft palate is treated in the areas of spots 932 and also in between spots 932. In alternative embodiments, any number, size, shape and pattern of electrodes may be used.

Figure 15:
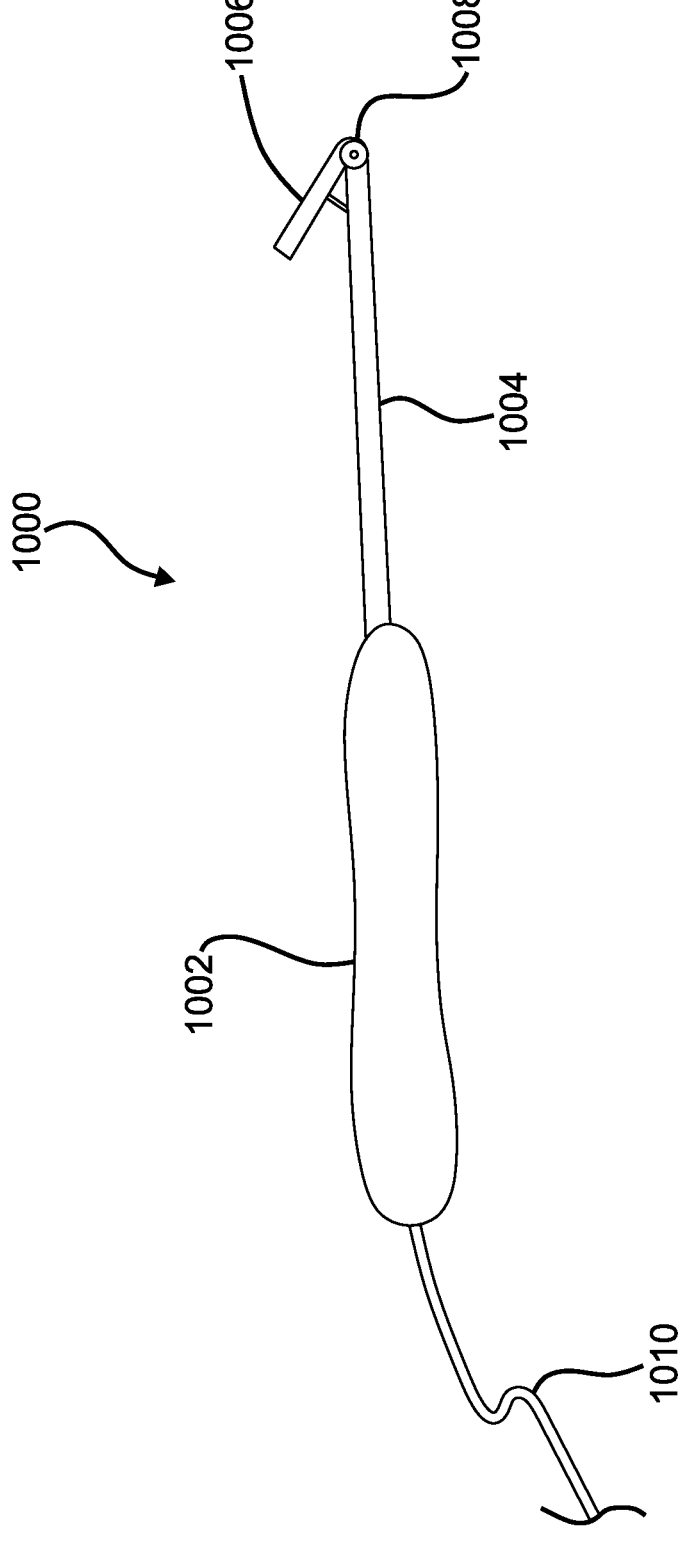
FIG. 15 is a side view of a soft palate treatment device with a moveable distal portion coupled with a shaft via a hinge, according to one embodiment.

FIG. 15 is a side view of yet another embodiment of a soft palate treatment device 1000, which is designed to access a top surface of the soft palate via access through the mouth. Treatment device 1000 includes a handle 1002, a shaft 1004, a distal treatment element 1006, a hinge 1008, and a cable 1010 for connecting to a source of energy, such as a console (not shown). In this embodiment, shaft 1004 may be advanced into the mouth with treatment element 1006 in a straight configuration relative to shaft 1004—i.e., not angled or only slightly angled. An actuator (not shown) on handle 1002, such as a slider or button, may be used to angle the treatment element 1006 relative to shaft 1004, via hinge 1008. Alternatively, the angle may be adjusted manually by the user, outside of the patient, and then shaft 1004 and treatment element 1006 may be advanced through the patient's mouth and used for treatment without further adjustment of hinge 1008. Electrodes or other energy delivery members may be located on treatment element 1006 and optionally also on shaft 1004. Energy may be delivered partway through the soft palate or all the way through the soft palate, according to various embodiments.

Figure 16:
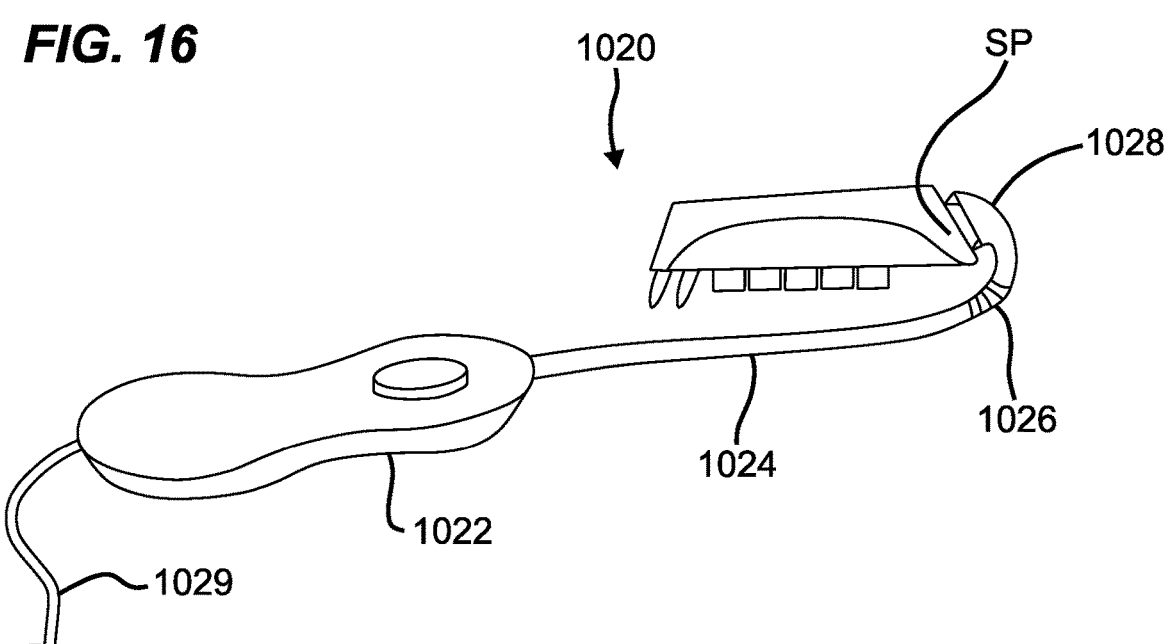
FIG. 16 is a perspective view of a soft palate treatment device with a malleable distal shaft portion, according to one embodiment.

FIG. 16 illustrates another embodiment of a soft palate treatment device 1020 that addresses the top side of the soft palate SP. In this embodiment, the treatment device 1020 includes a handle 1022, a shaft 1024 with a malleable section 1026, a treatment element 1028, and a cable 1029 for connecting with a console/energy source. In this embodiment, shaft 1024 may be bent at malleable portion 1026, before insertion into the mouth, so that treatment element 1028 is positioned at a desired angle to access the top (or "back" or "posterior") side of the soft palate SP. Treatment device 1020 may use any of the types of energy described herein and may include any of the features described in relation to any of the other embodiments described herein.

Figure 17:
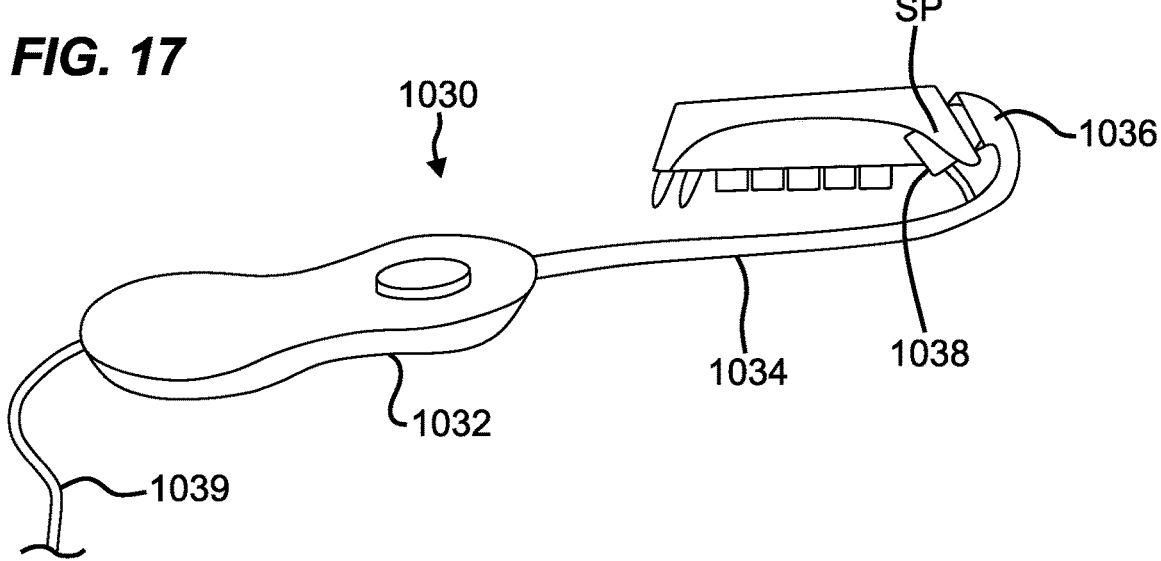
FIG. 17 is a perspective view of a soft palate treatment device with a jaw-like distal portion designed to contact two sides of the soft palate, according to one embodiment.

FIG. 17 illustrates another embodiment of a soft palate treatment device 1030 that addresses the top side of the soft palate SP. In this embodiment, the treatment device 1030 includes a handle 1032, a shaft 1034, a top-surface treatment element 1036, a bottom-surface treatment element 1038, and a cable 1039 for connecting with a console/energy source. In this embodiment, the two treatment elements 1036, 1038 sandwich the soft palate SP in between them and may deliver energy from both sides or from one side to the other. In some embodiments, handle 1032 may include an actuator (not shown) for adjusting the position of top-surface treatment element 1036, bottom-surface treatment element 1038, or both, so as to optimize their positions relative to the soft palate SP. Treatment device 1030 may use any of the types of energy described herein and may include any of the features described in relation to any of the other embodiments described herein.

Referring now to FIGS. 18A-18C, another embodiment of a soft palate treatment device 1040 may include a handle 1042, a shaft 1044, a treatment element 1046, and a cable 1054 that divides to connect to a radiofrequency energy source 1056 and a suction source 1058. Treatment element 1046 includes two electrodes 1048 on either side and a central channel 1050 (or "concavity") between the two electrodes 1048. Central channel 1050 leads into a lumen 1052 that runs through the length of shaft 1044 and handle 1042, then through cable 1054 to suction source 1058. A distal portion of treatment device 1040 is shown in FIGS. 18B and 18C, in which central channel 1050 and lumen 1052 are more easily visualized. Suction source 1058 creates a vacuum in lumen 1052, thus sucking air through central channel 1050. This suctioning of air may occur during all or a portion of a soft palate treatment with electrodes 1048, in order to cool mucosa of the soft palate during the treatment and thus prevent or reduce damage to the mucosa and reduce post-operative pain and discomfort. Electrodes 1048 may be bipolar electrodes, so that RF energy is sent through soft palate tissue from one electrode 1048 to the other electrode 1048 in a generally U-shaped trajectory. Treatment device 1040 may thus be used to treat soft palate tissue at a selected tissue depth beneath the mucosa, while maintaining a temperature of the mucosa and preventing it from being damaged.

Embodiments described further above in relation to FIGS. 11A-12 also included mucosa cooling mechanisms. The primary difference between the cooling mechanisms of those embodiments and the embodiment of FIGS. 18A-18C is that the former include a tissue contacting surface that is cooled from the inside and that cools by contacting the mucosa, while the embodiment of FIGS. 18A-18C draws air directly over the mucosa, so the air cools the tissue rather than a cooling surface of the device cooling the tissue. These represent two general types of cooling embodiments—those that contact the mucosa with a cooling portion of the device, and those that pass a substance onto or over the mucosa to cool it. In either embodiment, the substance used for cooling may be any suitable substance, such as but not limited to air, water, carbon dioxide, or any cryotherapeutic/cryogenic substance. In one embodiment, for example, treatment device 1040 may use $CO_2$ rather than air, and suction source 1058 may be replaced with a source of $CO_2$, such as a large canister that resides on the floor or a smaller $CO_2$ cartridge that may be attached to handle 1042. During use, treatment device 1040 may spray $CO_2$ gas onto the mucosa in the treatment area to keep the temperature of the mucosa at a desired level. Cooled water may similarly be used, although in such cases it may also be advantageous to apply suction, to remove the water from the patient's mouth. In various alternative embodiments, any cooling substance or combination of substances maybe used.

Figures 19, 20A, 20B:
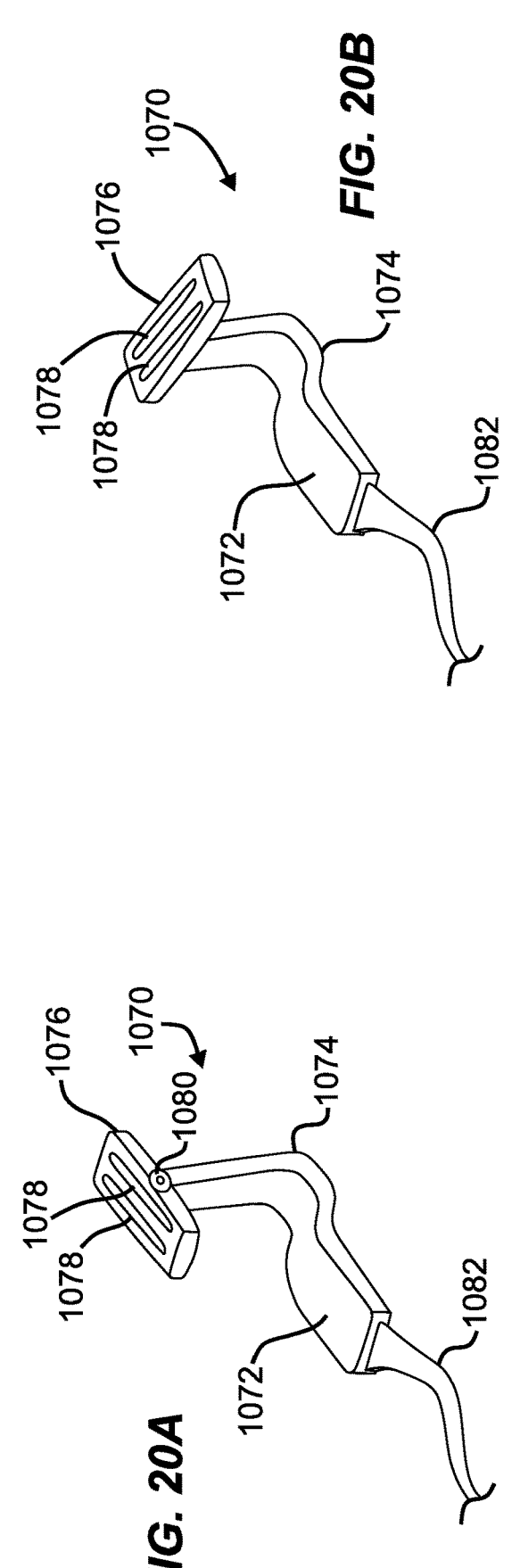
FIG. 19 is cross-sectional view of a human mouth and jaw and a side view of a soft palate treatment device that is held in place by the patient's teeth and/or lips, according to one embodiment.
FIGS. 20A and 20B are perspective views of a soft palate treatment device that is held in place by the patient's teeth and/or lips, according to an alternative embodiment.

With reference now to FIG. 19, another embodiment of a soft palate treatment device 1060 is illustrated in position within a patient's mouth, shown here as tongue TO, teeth TE and lips L. In this embodiment, treatment device 1060 is designed so that it can be held in place during all or a portion of a treatment by the patient himself or herself. This may be beneficial, for example, if a treatment time lasts several minutes, for example about three minutes or more. In this embodiment, treatment device 1060 includes a bite plate 1062 extending to a curved shaft 1064, which is coupled with a treatment element 1066 having multiple electrodes 1068 on one surface. Treatment device 1060 also includes a cable 1069 for connecting to a source of RF energy and optionally to suction, CO2 or other cooling mechanisms.

FIGS. 20A and 20B illustrate another embodiment of a patient-held soft palate treatment device 1070. This embodiment also includes a bite plate 1072, a curved shaft 1074, a treatment element 1076 with electrodes 1078 and a cable 1082. Additionally, treatment device 1070 includes a swivel 1080, which allows treatment element 1076 to rotate relative to shaft 1074. This allows treatment element 1076 to be positioned in two or more different orientations, to apply RF energy from electrodes 1078 to tissue in a pattern. In some embodiments, treatment element 1076 may lock in two positions, for example the "straight" position of FIG. 20A and the "right-angle" position of FIG. 20B. In other embodiments, treatment element 1076 may be adjusted to any position desired by the user. In one method of use, treatment element 1076 may be used for a first treatment in a first configuration, then removed from the patients mouth, adjusted to a different angle/orientation, and used for a second treatment in a second configuration. This method may be repeated as many times as desired to create a specific tissue treatment pattern.

Figures 21A, 21B:
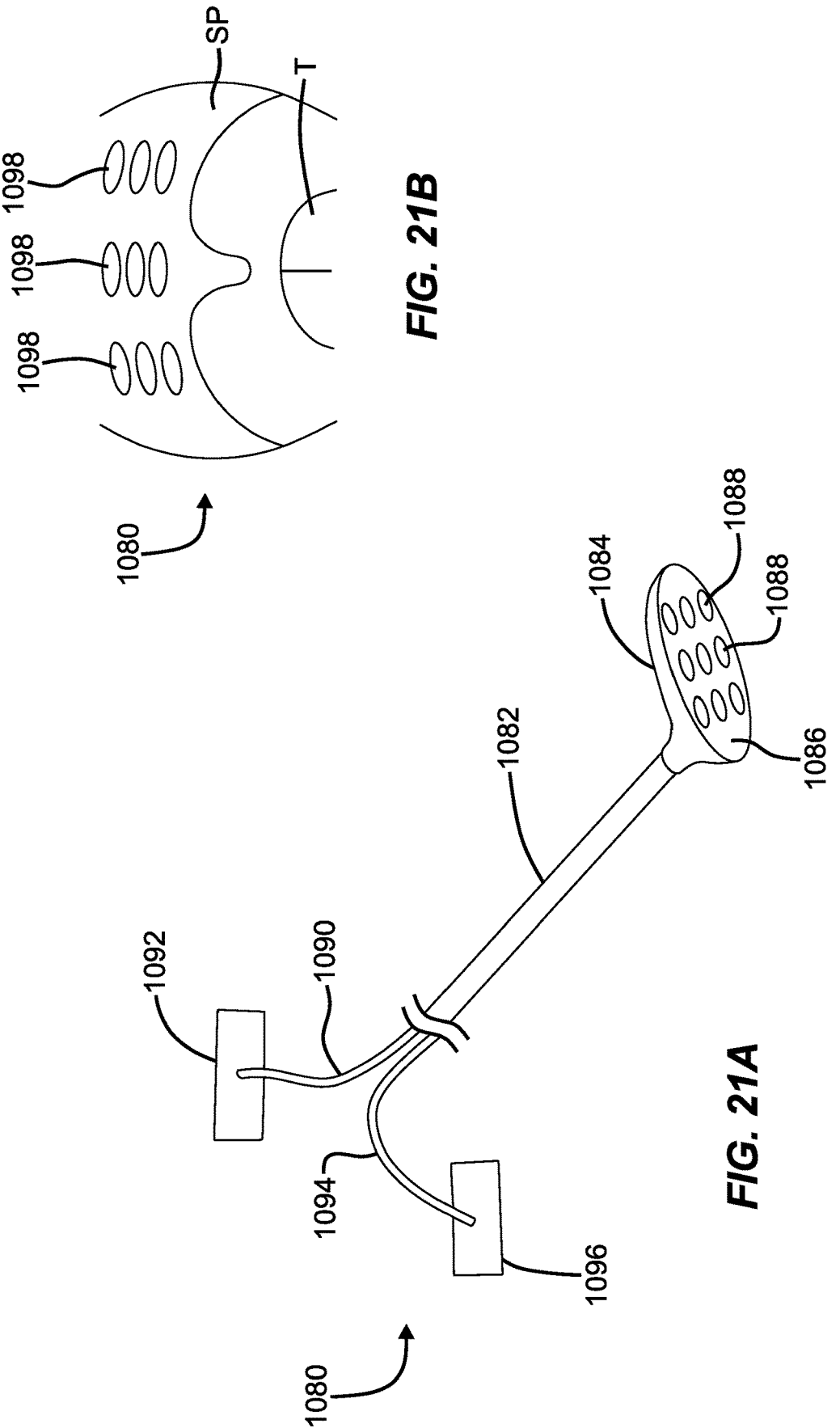
FIG. 21A is a perspective view of a soft palate treatment system, according to another embodiment.
FIG. 21B is a diagrammatic view of a soft palate, illustrating one possible treatment pattern using the device of FIG. 21A.

Referring now to FIGS. 21A and 21B, in another embodiment, a soft palate treatment device 1080 includes a shaft 1082 coupled with a handle (not pictured) at one end and a treatment element 1084 at the opposite end. Treatment element 1084 includes a treatment surface 1086 with multiple electrodes 1088 (or other energy delivery members in alternative embodiments). Attached to the proximal end of treatment device 1080 are a first cable 1090 attached to a source of radiofrequency energy 1092 (or other energy source in alternative embodiments), and a second cable 1094 attached to a suction source 1096 (or other cooling source in alternative embodiments). In this embodiment, electrodes 1088 are flat and flush with tissue treatment surface 1086, and there are three rows of three electrodes 1088 each. Alternative embodiments may include any number and configuration of electrodes 1088. As illustrated in FIG. 21B, treatment device 1080 may be used to make a treatment pattern 1098 across the soft palate SP as shown. This treatment pattern may stiffen the soft palate SP, and the location of the lesions may be advantageous, if for example the top row of lesions is positioned along the junction of the soft palate and the hard palate, and the bottom row of lesions is positioned along the junction of the soft palate and the uvula musculature.

Figure 22A:
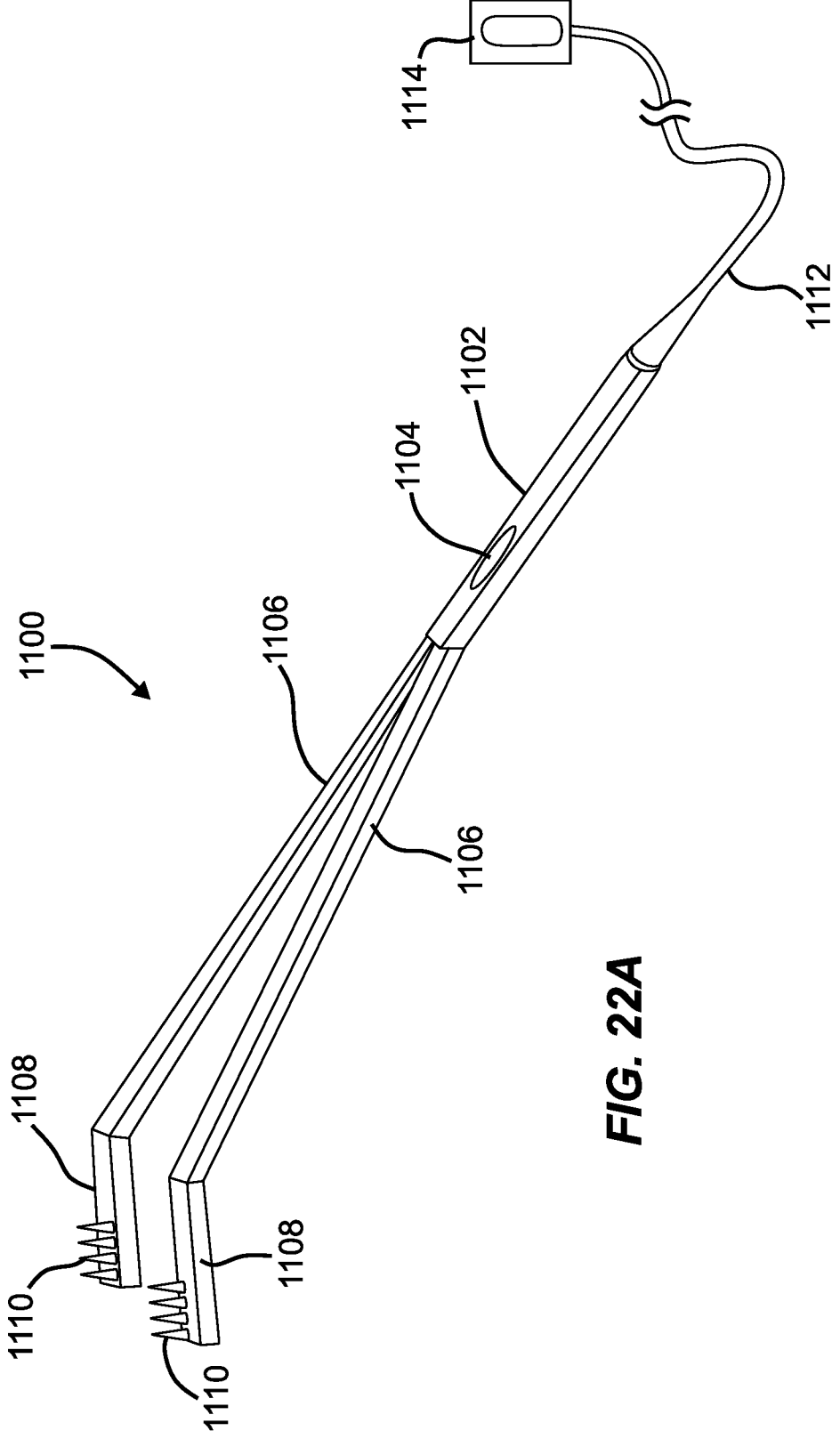
FIG. 22A is a perspective view of a soft palate treatment device with a tong-like configuration for pinching soft palate tissue between electrodes, according to one embodiment.
Figure 22B:
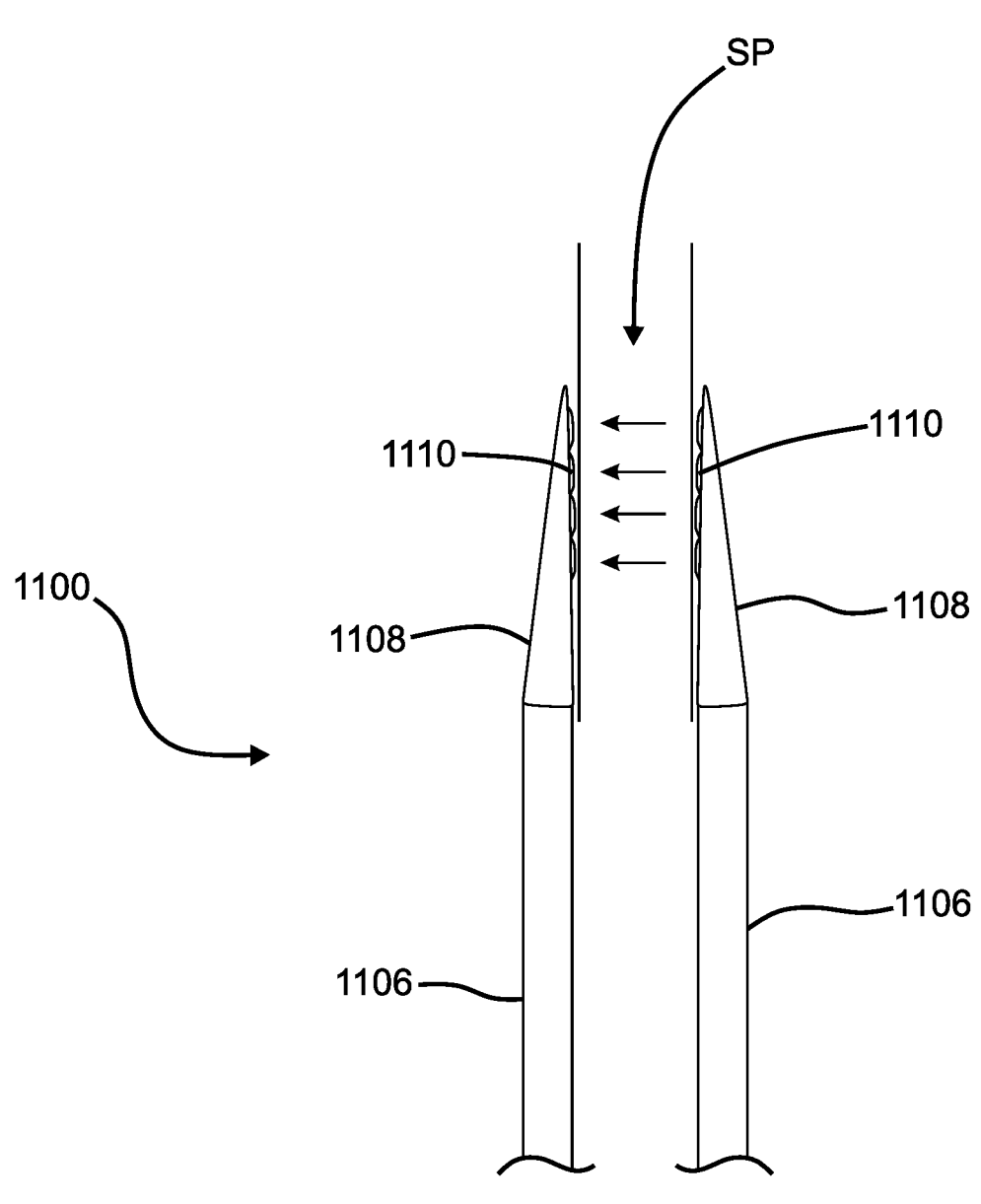
FIG. 22B is a top view of a distal portion of the device of FIG. 22A during a treatment of soft palate tissue.

FIGS. 22A and 22B show yet another embodiment of a soft palate treatment device 1100. In this embodiment, treatment device 1100 includes a handle 1102 with an actuator 1104, two shafts 1106 forming a tong-like, V-shaped structure, and two treatment elements 1108 at the end of shafts 1106, each having multiple electrodes 1110. The proximal end of handle 1102 is coupled with a cable 1112 that is attached to a foot pedal 1114. Generally, foot pedal 1114 is used for controlling (turning on and off) the delivery of RF energy to the treatment tissue via the electrodes 1110. In some embodiments, actuator 1104 may also be used to turn on and off the delivery of RF energy. Actuator 1104 may also (or alternatively) be configured to manipulate treatment elements 1108 relative to one another, to trap/pinch the treatment tissue between them. In some embodiments, handle 1102 may include a mechanism (such as but not limited to actuator 1104) for moving shafts 1106 closer to one another and farther apart from one another to control positioning of treatment elements 1108.

FIG. 22B shows a distal portion of treatment device 1100 with a figurative depiction of soft palate SP tissue pinched between the two treatment elements 1108. The pointed shape of electrodes 1110, in this embodiment, may facilitate grasping mucosal tissue with treatment elements 1108 and pinching the tissue slightly. Radiofrequency energy may then be delivered across/through the tissue, as depicted by the solid-tipped arrows in FIG. 22B. Pinching or grasping the tissue in this manner may help isolate tissue to be treated and/or enhance energy delivery to a desired treatment depth.

In an alternative embodiment, one tong or clamshell of the treatment device may include one or more needle electrodes, and the opposite tong or clamshell may include one or more magnets. The magnet(s) may have a set depth of magnetic field to the needle electrode(s) on the other tong/clamshell into soft palate, while preventing the needle(s) from accidentally poking through nasal side of the soft palate.

Figure 23:
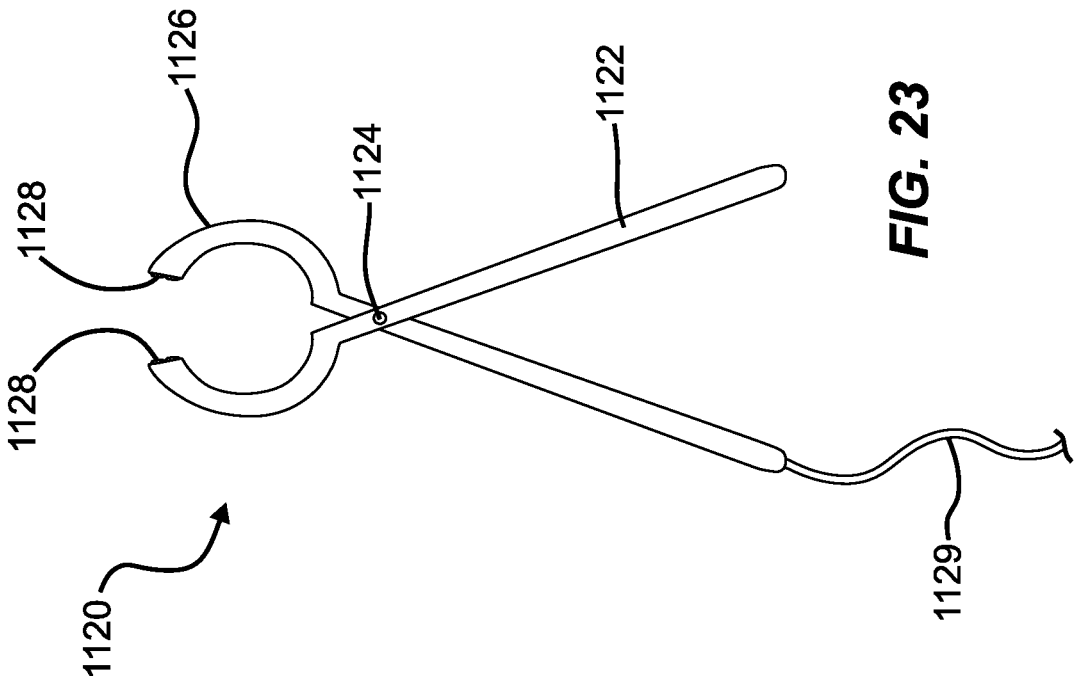
FIG. 23 is a top view of a soft palate treatment device with a scissor-like configuration for pinching soft palate tissue between electrodes, according to an alternative embodiment.

Referring now to FIG. 23, in another embodiment, a soft palate treatment device 1120 includes a scissor-like handle 1122 with two pieces coupled together at a hinge 1124, extending to two curved distal portions 1126 ending in tissue treatment surfaces with electrodes 1128 on them. One of the two portions of handle 1122 is coupled with a cable 1129 for transmitting RF energy (or other forms of energy in alternative embodiments) to electrodes 1128. This embodiment of treatment device 1120 may be used similarly to that depicted in FIGS. 22A and 22B, in that it may be used to pinch tissue between electrodes 1128.

Figure 24:
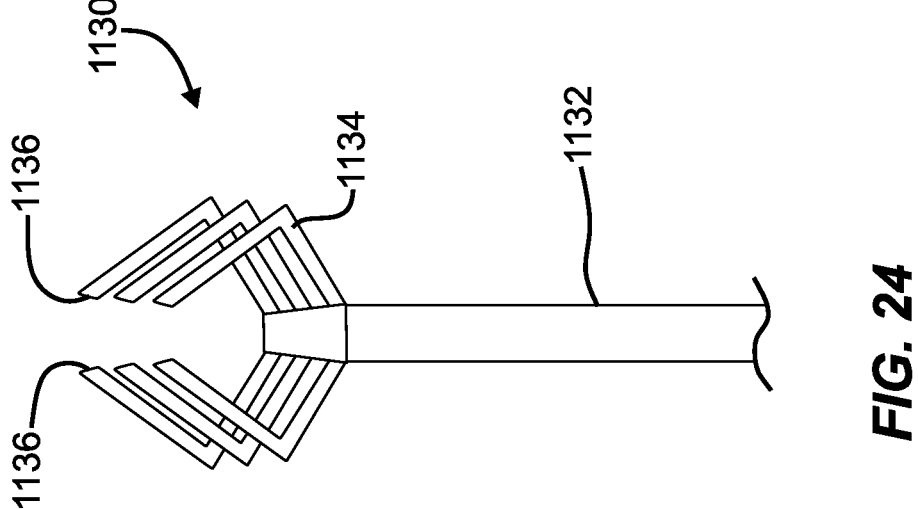
FIG. 24 is a perspective view of a distal portion of a soft palate treatment device with multiple moveable arms for pinching soft palate tissue between electrodes, according to yet another embodiment.

FIG. 24 illustrates a distal end of yet another embodiment of a soft palate treatment device 1130, including a shaft 1132 (handle not shown) and multiple movable arms 1134 attached to the distal end of the shaft 1132. Each arm 1134 has a treatment surface with at least one electrode 1136 attached to it. An actuator on the handle may be used to open and close arms 1134 to pinch soft palate tissue for performing an energy delivery treatment. This embodiment may include any of the features described above.

Figure 25:
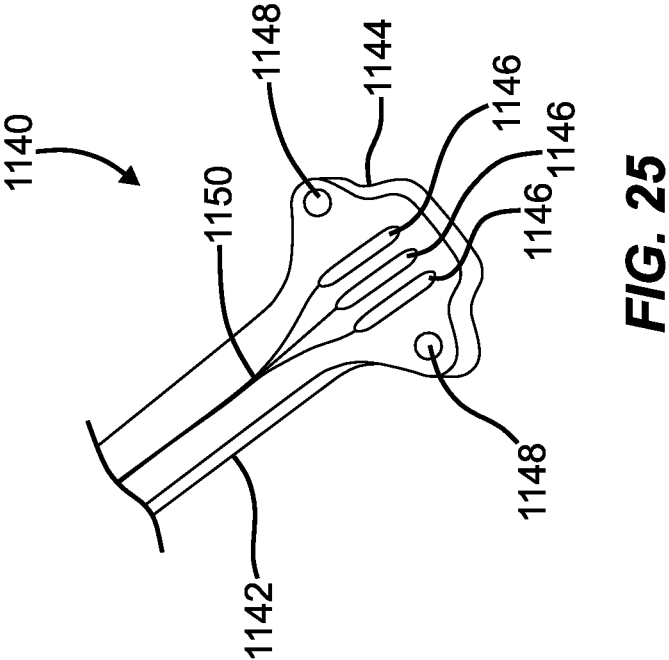
FIG. 25 is a perspective view of a distal portion of a soft palate treatment device with magnets for attracting a second portion of the device across the soft palate, according to one embodiment.

FIG. 25 is a perspective view of a distal portion of a soft palate treatment device 1140, according to another embodiment. In this embodiment, treatment device 1140 includes a shaft 1142 connected proximally to a handle (not illustrated), a treatment element 1144, multiple bipolar RF electrodes 1146, two magnets 1148 and wiring 1150 connecting RF electrodes 1146 to the handle and thus to a source of RF energy. The portion of treatment device 1140 shown in FIG. 25 is one part of the distal portion of device 1140, which is used on the mouth facing side of the soft palate. Another portion, which may have the same shape and configuration as the portion shown, may be used on the nasal cavity facing surface of the soft palate, and the two portions may be attracted to one another via magnets 1148. In this embodiment, magnets 1148 are located to either side of RF electrodes 1146 on tab-like protrusions on treatment element 1144. In various embodiments, the number, size, shape and positions of RF electrodes 1146 and magnets 1148 may be changed in any suitable manner.

Figure 26:
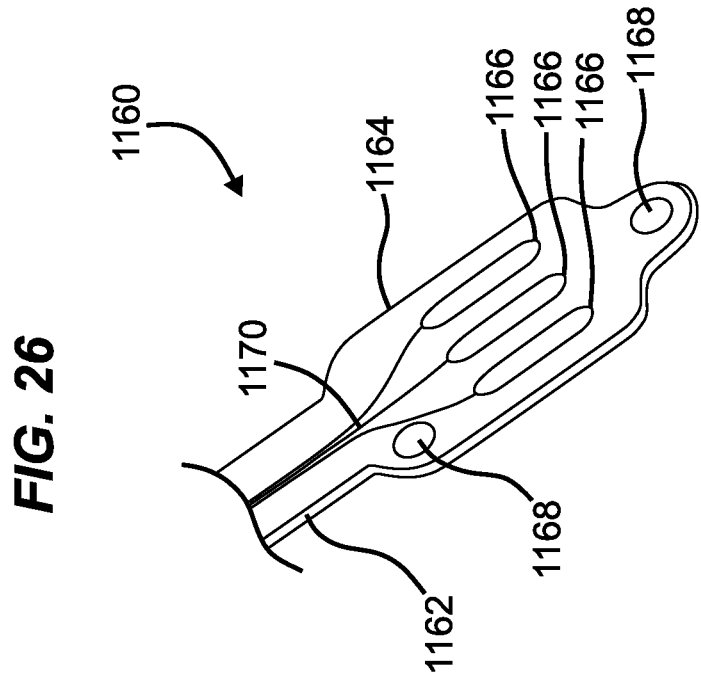
FIG. 26 is a perspective view of a distal portion of a soft palate treatment device with magnets for attracting a second portion of the device across the soft palate, according to an alternative embodiment.

FIG. 26 is a perspective view of a distal portion of a soft palate treatment device 1160, according to another embodiment. Similar to FIG. 25, only the mouth facing portion of treatment device 1160 is shown. In this embodiment, treatment device 1160 includes a shaft 1162 connected proximally to a handle (not illustrated), a treatment element 1164, multiple bipolar RF electrodes 1166, two magnets 1168 and wiring 1170 connecting RF electrodes 1166 to the handle and thus to a source of RF energy. In this embodiment, magnets 1168 are located in front of and behind RF electrodes 1166, thus allowing for a longer, thinner treatment element 1164 than the embodiment of FIG. 25. In various embodiments, the number, size, shape and positions of electrodes 1166 and magnets 1168 may be changed in any suitable manner.

Figure 27:
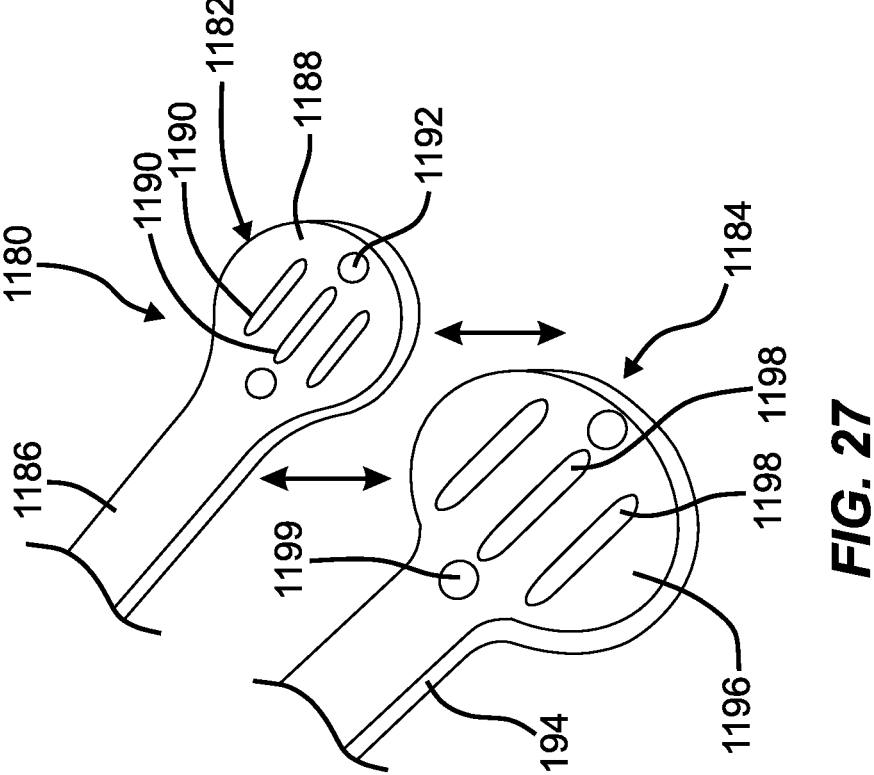
FIG. 27 is a perspective view of two distal portions of a soft palate treatment device with magnets for attracting each other across the soft palate, according to one embodiment.

FIG. 27 is a perspective view of another alternative embodiment of a soft palate treatment device 1180. In this embodiment, treatment device 1180 includes a top portion 1182 (or "nasal facing portion") and a bottom portion 1184 (or "mouth facing portion"). Top portion 1182 includes a shaft 1186, a handle (not shown), a treatment element 1188, multiple bipolar RF electrodes 1190 and two magnets 1192. Similarly, bottom portion 1184 includes a shaft 1194, a handle (not shown), a treatment element 1196, multiple bipolar RF electrodes 1198 and two magnets 1199. In use, top portion 1182 may be advanced through the patient's nose, and bottom portion 1184 may be advanced through the patient's mouth. When in position, the two portions 1182, 1184 are attracted to each other via magnets 1192, 1199, to sandwich the soft palate between the two portions 1182, 1184. Radiofrequency energy may then be transmitted across/through the soft palate tissue from one set of electrodes 1190 to the other set 1198 (in either direction). In various embodiments, the number, size, shape and positions of electrodes 1190, 1198 and magnets 1192, 1199 may be changed in any suitable manner. Using magnetic soft palate treatment device 1180 and variations thereof, many different treatment patterns may be generated, one example of which is illustrated in FIG. 14B.

Figure 28:
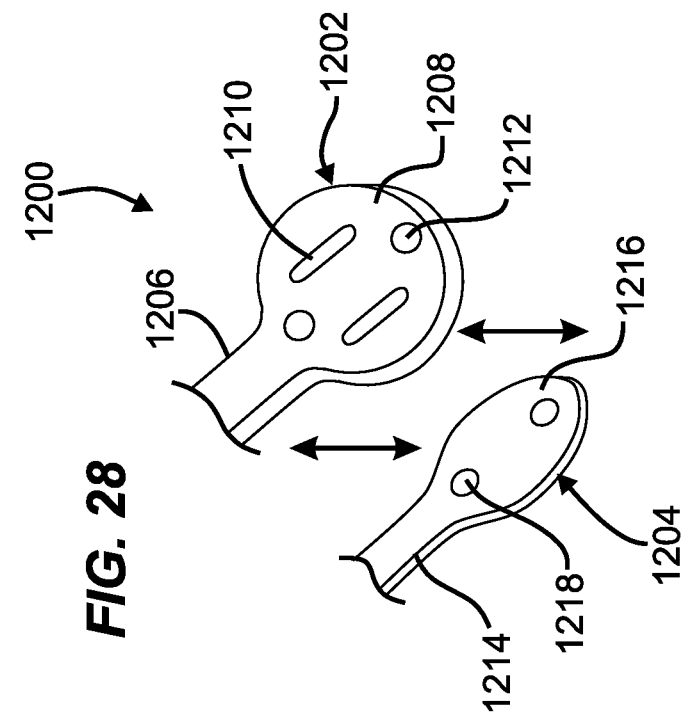
FIG. 28 is a perspective view of two distal portions of a soft palate treatment device with magnets for attracting each other across the soft palate, according to an alternative embodiment.

FIG. 28 is a perspective view of another alternative embodiment of a soft palate treatment device 1200. In this embodiment, treatment device 1200 includes a top portion 1202 (or "nasal facing portion") and a bottom portion 1204 (or "mouth facing portion"). Top portion 1202 includes a shaft 1206, a handle (not shown), a treatment element 1208, multiple bipolar RF electrodes 1210 and two magnets 1212. Similarly, bottom portion 1204 includes a shaft 1214, a handle (not shown), a treatment element 1216 and two magnets 1218. In this embodiment, only top portion 1202, and not bottom portion 1204, includes electrodes 1210. In an alternative embodiment, only the bottom portion 1204 may include electrodes. In use, top portion 1202 may be advanced through the patient's nose, and bottom portion 1204 may be advanced through the patient's mouth. When in position, the two portions 1202, 1204 are attracted to each other via magnets 1212, 1218, to sandwich the soft palate between the two portions 1202, 1204. Radiofrequency energy may then be transmitted from one of electrodes 1210 through soft palate tissue to the other of electrodes 1210, to treat tissue at a desired tissue treatment depth below the mucosa. In various embodiments, the number, size, shape and positions of electrodes 1210 and magnets 1212, 1218 may be changed in any suitable manner. Using magnetic soft palate treatment device 1200 and variations thereof, many different treatment patterns may be generated, one example of which is illustrated in FIG. 14B.

Figure 29A:
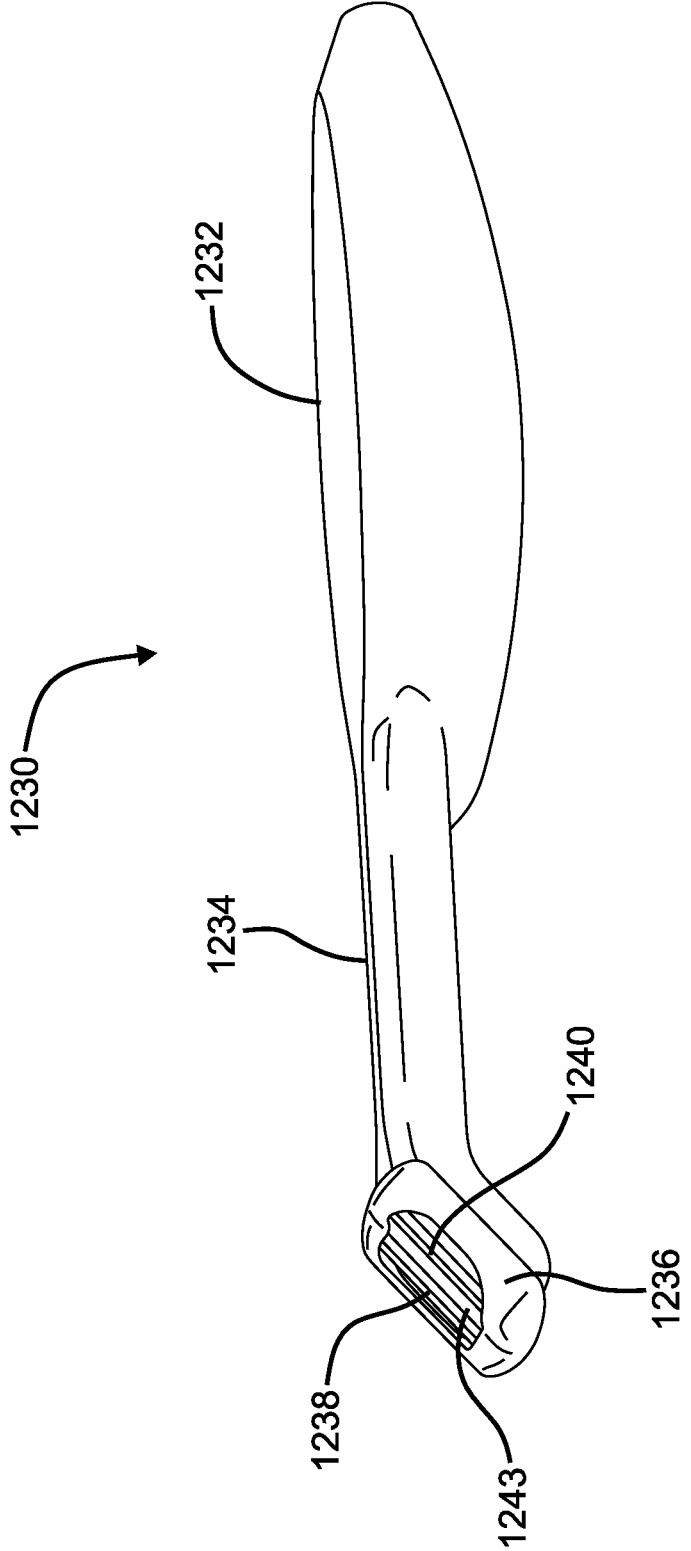
FIGS. 29A and 29B are perspective and cross-sectional views, respectively, of a soft palate treatment device with a heat sink and thermoelectric cooler, according to one embodiment.
Figure 29B:
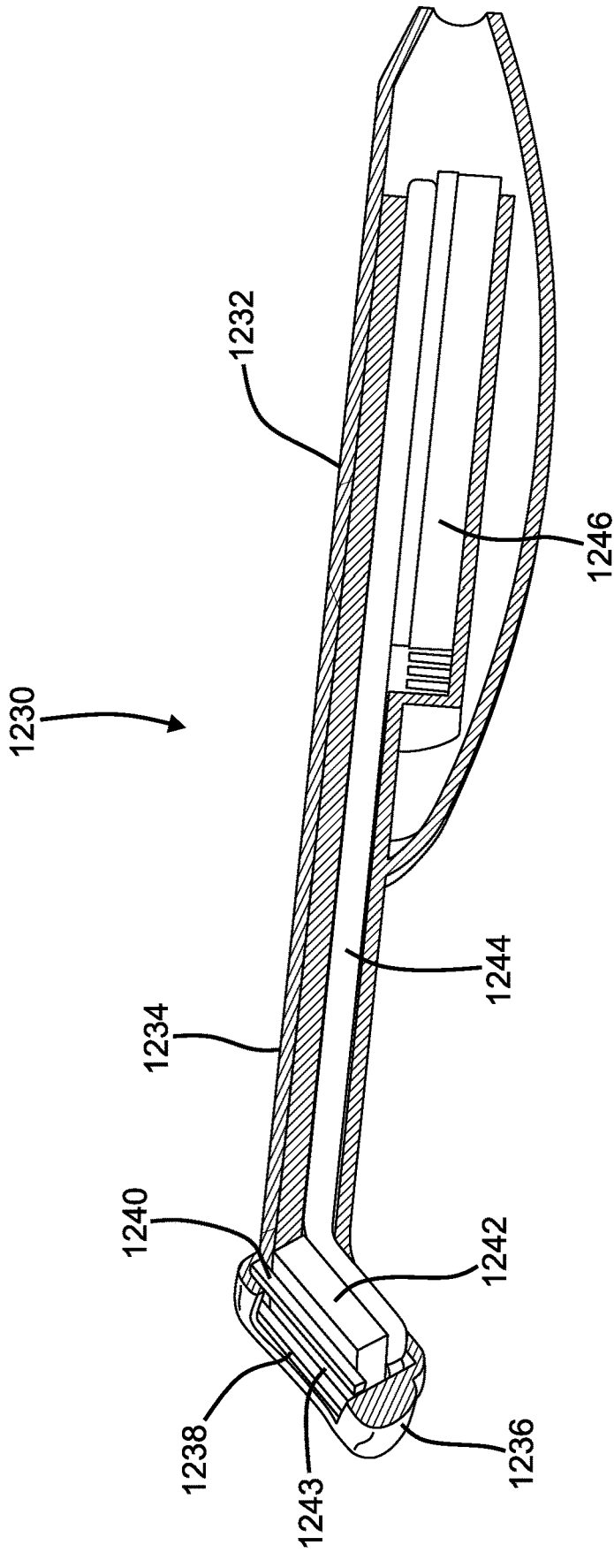

FIGS. 29A and 29B are perspective and cross-sectional drawings, respectively, of another embodiment of a soft palate treatment device 1230. As visible in FIG. 29A, treatment device 1230 includes a handle 1232, a shaft 1234, and a treatment element 1236 (or "treatment head"), which includes a first bipolar electrode 1238, a second bipolar electrode 1240, and a heat dissipating member 1243. Handle 1232 is typically connected at its proximal end to a cable (not shown), for connecting with a source of RF energy. In this embodiment, the tissue contacted by electrodes 1238, 1240 is cooled via a heat sink, as described further in reference to FIG. 29B. Heat dissipating member 1243 is positioned between electrodes 1238, 1240 and is thermally conductive and electrically insulating. In some embodiments, heat dissipating member 1243 may have a surface shape, such as concave, to allow tissue to contact a cooling member disposed below it (described further below).

FIG. 29B shows soft palate treatment device 1230 in longitudinal cross section. Inside, treatment device 1230 includes a thermoelectric cooler 1242 (or "Peltier" cooler) inside treatment element 1236, a heat pipe 1244 extending down shaft 1234, and a heat sink 1246 inside handle 1232. During a treatment, RF energy is transmitted from first bipolar RF electrode 1238 to second bipolar RF electrode 1240 (or vice versa). Heat from mucosal tissue in the area of treatment is transferred through thermoelectric cooler 1242 to heat pipe 1244 and thus to heat sink 1246. In some embodiments, one or more heat sensors, such as but not limited to a thermocouple (not visible) may be positioned on the surface of thermoelectric cooler 1242 or at some other location (or locations) on treatment element 1236, to sense a temperature of tissue in the area of treatment. Sensed temperatures may then be used to activate thermoelectric cooler 1242, as needed, to maintain the local tissue temperature within a desired range. Thermoelectric cooler 1242 is also configured and positioned to cool electrodes 1238, 1240. Electrodes 1238, 1240 may be long, thin electrodes and in some embodiments may be made of a tape or foil. In some alternative embodiments, handle 1232 may include one or more ports or vents for helping cool treatment element 1236, for example via suction or introduction of a cooling gas. Such ports or vents may be in addition to, or as an alternative to, heat sink 1246.

For many or all of the above-described embodiments, various device dimensions and treatment parameters may be used, in an effort to optimize the ease of use for the treating physician and the treatment results for the patient. The following dimensions and parameters may be applied to any of the embodiments described above. For example, in embodiments of a soft palate treatment device that include two bipolar RF electrodes, each electrode may have a width of between about 0.5 mm and about 10 mm, or more preferably between about 1 mm and about 5 mm, and a length of between about 10 mm and 30 mm, or more preferably between about 15 mm and about 20 mm. The width of the tip (or "treatment element") of the soft palate treatment device may be between about 10 mm and about 30 mm, or preferably between about 10 mm and about 20 mm. The length of the tip may also be between about 10 mm and about 30 mm, or preferably between about 10 mm and about 20 mm. In many embodiments, although not necessarily all embodiments, the length of the tip is greater than the width.

In various embodiments, each tissue treatment may have a duration of about 12 seconds to about 5 minutes, or preferably about 30 seconds to about 3 minutes. One tissue treatment is defined for this purpose as one treatment at one specific location on the soft palate or other structure. A complete treatment of a patient may include one tissue treatment or multiple tissue treatments—any number is possible. In some embodiments, the tissue treatment device may be programmed to provide only a certain number of tissue treatments per patient and may automatically and permanently shut down after that number has been reached. Other possible treatment parameters include: power, which may be controlled to between about 1 W and about 20 W, or preferably between about 3 W and about 10 W; treatment temperature, which may be maintained in a range of about 46 degrees Celsius to about 85 degrees Celsius; and cooling threshold temperature, which may be between about 40 degrees Celsius and about 60 degrees Celsius. In some embodiments, treatment of the soft palate starts at the level of the mucosa and penetrates beneath it, for example to a tissue depth of between about 1 mm and about 15 mm, or preferably between about 4 mm and about 6 mm. In other embodiments, for example those in which mucosal tissue is cooled by the device during treatment, the depth of treated tissue might be different, and the mucosa might be preserved, in other words not treated at all or barely treated. In some embodiments, for example, the mucosal tissue might be preserved to a depth of between about 0.5 mm and about 1 mm—in other words, tissue treatment starts at least about 0.5 mm below the tissue surface. These dimensions and parameter amounts are only examples, and in some embodiments any or all of the dimensions and parameters may be outside of these ranges.

Although various embodiments are described herein, the present invention extends beyond the specifically disclosed embodiments to other alternative embodiments and/or uses of the invention and modifications and equivalents thereof. Thus, the scope of the present invention should not be limited by the disclosed embodiments, but should be determined only by a fair reading of the claims that follow.

What is claimed is:

1. A method of treating a soft palate in a patient, the method comprising:

advancing a tissue treatment portion of a soft palate treatment device through a mouth of the patient, the tissue treatment portion having an elongate portion and a hook-shaped distal end configured to fit around an end of the soft palate, and having a treatment surface, the treatment surface comprising:

a first longitudinal electrode positioned on a first lateral side of the tissue treatment portion and extending along a length of the tissue treatment portion from a proximal end of the tissue treatment portion to a distal end of the tissue treatment portion, a second longitudinal electrode positioned on a second lateral side of the tissue treatment portion and extending along the length of the tissue treatment portion from the proximal end of the tissue treatment portion to the distal end of the tissue treatment portion; and a cooling member positioned between the first and second longitudinal electrodes and extending along the length of the tissue treatment portion from the proximal end of the tissue treatment portion to the distal end of the tissue treatment portion;

contacting mucosal tissue with the tissue treatment portion, wherein an inferior surface of the soft palate is contacted with the elongate portion of the tissue treatment portion and a superior surface of the soft palate is contacted with the hook-shaped distal end of the tissue treatment portion;

delivering energy from the first longitudinal electrode of the tissue treatment portion through the mucosal tissue to a target tissue in the soft palate beneath the mucosal tissue, to change at least one property of the target tissue, receiving, with the second longitudinal electrode, the energy delivered from the first longitudinal electrode, cooling the mucosal tissue between the first and second longitudinal electrodes with the cooling member on the tissue treatment portion during delivery of energy such that the target tissue is treated at a selected tissue depth in a U-shaped energy delivery path from the first longitudinal electrode and through the target tissue to the second longitudinal electrode; and removing the tissue treatment portion from the mouth.

2. The method of claim 1, wherein the change in the at least one property of the target tissue results in a reduction of at least one of snoring or sleep apnea in the patient.

3. The method of claim 1, further comprising applying force against the soft palate with the treatment surface while delivering the energy, to deform tissue of the soft palate, wherein changing the at least one property of the target tissue comprises reshaping the target tissue.

4. The method of claim 1, wherein changing the at least one property of the target tissue comprises at least one of reshaping, remodeling, stiffening, strengthening, tightening, shortening, thickening or ablating the target tissue.

5. The method of claim 1, wherein the energy is selected from the group consisting of radiofrequency, microwave, ultrasound, heat and cryogenic energy.

6. The method of claim 1, further comprising:

repositioning the tissue treatment portion to a new location on the soft palate; and delivering the energy to the target tissue again, to form a treatment pattern in the target tissue.

7. The method of claim 1, wherein cooling the mucosal tissue comprises applying a suction force with the cooling member to suction air through the cooling member.

8. The method of claim 1, wherein cooling the mucosal tissue comprises circulating a cooling fluid through the cooling member.

9. The method of claim 1, wherein the cooling member comprises a thermoelectric cooler on the treatment surface, coupled with a heat pipe in a shaft of the soft palate treatment device, which is coupled with a heat sink in a handle of the soft palate treatment device.

10. The method of claim 1, further comprising:

measuring a temperature of the mucosal tissue with a temperature sensing member on the treatment surface of the tissue treatment portion; and automatically controlling, with a controller coupled with the soft palate treatment device, at least one of energy delivery or cooling, based on the temperature.

11. The method of claim 1, wherein the target tissue is selected from the group consisting of muscle, cartilage, tendon, ligament, connective tissue, nerve and blood vessel.

12. The method of claim 1, further comprising bending a malleable shaft of the soft palate treatment device before advancing the tissue treatment portion.

13. The method of claim 1, further comprising applying force to the mucosal tissue with the tissue treatment portion to cause the tissue treatment portion to flex at at least one flex point along the tissue treatment portion.

14. The method of claim 1, wherein the cooling member includes an air vent.

15. A device for treating a soft palate in a patient, the device comprising:

a handle;

a shaft having a proximal end attached to the handle and a distal end;

a treatment element extending from the distal end of the shaft, the treatment element having an elongate portion and a hook-shaped distal end configured to fit around an end of the soft palate, the treatment element comprising:

a treatment surface;

a first longitudinal electrode on the treatment surface; and a second longitudinal electrode on the treatment surface;

a cooling mechanism positioned between the first longitudinal electrode and the second longitudinal electrode, the cooling mechanism configured to couple to a suction source for suctioning cooling fluid through the cooling mechanism, wherein the first longitudinal electrode is configured to deliver radiofrequency energy to tissue, the second longitudinal electrode is configured to receive the energy delivered from the first longitudinal electrode, and the cooling mechanism is configured to cool the tissue between the first longitudinal electrode and the second longitudinal electrode such that the energy is delivered to the tissue in a U-shaped energy delivery path from the first longitudinal electrode to the second longitudinal electrode;

wherein the elongate portion of the treatment element is configured to contact an inferior surface of the soft palate and the hook-shaped distal end of the treatment element is configured to contact a superior surface of the soft palate; and a connector for connecting the handle with a power source and a cooling source.

16. The device of claim 15, wherein the distal end of the shaft comprises a neck that is angled relative to a longitudinal axis of the shaft, and wherein the treatment element is attached to the neck.

17. The device of claim 15, wherein the first longitudinal electrode and the second longitudinal electrode comprise elongate bipolar radiofrequency electrodes.

18. The device of claim 15, wherein each of the first longitudinal electrode and the second longitudinal electrode comprises a protruding, non-penetrating electrode.

19. The device of claim 15, wherein the treatment surface has a convex shape for creating a concave deformity in the soft palate.

20. The device of claim 15, wherein the shaft is malleable.

21. The device of claim 15, further comprising at least one flex member on a top surface of the treatment element.

22. The device of claim 15, further comprising a temperature sensing member on the elongate-treatment element, for sensing a temperature of mucosal tissue in contact with the treatment surface.

23. The device of claim 15, wherein the cooling mechanism comprises a central channel extending from a proximal end of the treatment surface to a distal end of the treatment surface to couple to a lumen extending through the shaft and the handle to the suction source.

24. A device for treating a soft palate in a patient, the device comprising:

a handle;

a shaft having a proximal end attached to the handle and a distal end;

a treatment element extending from the distal end of the shaft and having an elongate portion and a hook-shaped distal end configured to fit around an end of the soft palate, the treatment element comprising:

a treatment surface;

a first longitudinal electrode positioned on a first lateral side of the treatment surface and extending along a length of the treatment surface from a proximal end of the treatment surface to a distal end of the treatment surface;

a second longitudinal electrode positioned on a second lateral side of the treatment surface and extending along the length of the treatment surface from the proximal end of the treatment surface to the distal end of the treatment surface;

a cooling mechanism positioned between the first longitudinal electrode and the second longitudinal electrode, wherein the first longitudinal electrode is configured to deliver radiofrequency energy to tissue, the second longitudinal electrode is configured to receive the energy delivered from the first longitudinal electrode, and the cooling mechanism is configured to cool the tissue between the first longitudinal electrode and the second longitudinal electrode such that the energy is delivered to the tissue in a U-shaped energy delivery path;

wherein the elongate portion of the treatment element is configured to contact an inferior surface of the soft palate and the hook-shaped distal end of the treatment element is configured to contact a superior surface of the soft palate; and a connector for connecting the handle with a power source and a cooling source.

25. The device of claim 24, wherein the cooling mechanism includes an air vent.

* * * * *